US012370169B2

(12) United States Patent
Kolluri et al.

(10) Patent No.: US 12,370,169 B2
(45) Date of Patent: Jul. 29, 2025

(54) SMALL MOLECULE Bcl-2 FUNCTIONAL CONVERTERS AS CANCER THERAPEUTICS

(71) Applicant: Oregon State University, Corvallis, OR (US)

(72) Inventors: Siva K. Kolluri, Corvallis, OR (US); Prasad R. Kopparapu, Houston, TX (US); Martin Pearce, Independence, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 17/821,146

(22) Filed: Aug. 19, 2022

(65) Prior Publication Data

US 2023/0129487 A1 Apr. 27, 2023

Related U.S. Application Data

(63) Continuation of application No. 16/465,971, filed as application No. PCT/US2017/064335 on Dec. 1, 2017, now Pat. No. 11,419,843.

(60) Provisional application No. 62/428,864, filed on Dec. 1, 2016.

(51) Int. Cl.
| | | |
|---|---|---|
| *A61K 31/341* | (2006.01) | |
| *A61K 31/167* | (2006.01) | |
| *A61K 38/16* | (2006.01) | |
| *A61K 45/06* | (2006.01) | |

(52) U.S. Cl.
CPC .......... *A61K 31/341* (2013.01); *A61K 31/167* (2013.01); *A61K 38/16* (2013.01); *A61K 45/06* (2013.01)

(58) Field of Classification Search
CPC .... A61K 31/09; A61K 31/167; A61K 31/341; A61K 31/519; A61K 38/16; A61P 35/00
See application file for complete search history.

(56) References Cited

U.S. PATENT DOCUMENTS

| | | |
|---|---|---|
| 8,481,505 B2 | 7/2013 | Croce et al. |
| 2005/0038248 A1 | 2/2005 | Henderson et al. |
| 2007/0054863 A1 | 3/2007 | Satterthwait et al. |
| 2008/0138847 A1 | 6/2008 | Shi |
| 2009/0082424 A1 | 3/2009 | Wang et al. |
| 2009/0118135 A1 | 5/2009 | Reed et al. |
| 2010/0286057 A1 | 11/2010 | Walensky et al. |
| 2013/0157260 A1 | 6/2013 | Satterthwait et al. |
| 2015/0018285 A1 | 1/2015 | Larisch |

FOREIGN PATENT DOCUMENTS

| | | | |
|---|---|---|---|
| CN | 103130696 A | 6/2013 | |
| WO | 2005085188 A2 | 9/2005 | |
| WO | WO-2011127192 A2 * | 10/2011 | ........... A61K 31/167 |

OTHER PUBLICATIONS

Kirkin et al., Biochimica et Biophysica Acta, vol. 1644, pp. 229-249, publ. 2004 (Year: 2004).*
Bhatia, S., et al., "The Challenges Posed By Cancer Heterogeneity," Nature Biotechnology, 30(7): 604-610, 2012.
ChemBridge Corp, CAS STN abstract, RN 692771-06-5 & RN 709011-06-3, publ. 2004, 2 pages.
Chen J., et al., "Enhanced Mitochondrial Gene Transcript, ATP, Bcl-2 Protein Levels, and Altered Glutathione Distribution on Ethinyl Estradiol-Treated Cultured Female Rat Hepatocytes," Toxicological Sciences, 75, pp. 271-278, 2003.
Kaiser, J., "Cancer Genetics With an Edge," Science, 337(6092): 282-284, 2012.
Rodriguez, D., "Know the Most Common Types of Cancer," Everyday Health, <https://www.everydayhealth.com/cancer/know-the-most-common-types-of-cancer.aspx> [retrieved Feb. 5, 2021], Feb. 8, 2010, 13 pages.
Wistuba, I.I., et al., "Methodological and Practical Challenges for Personal Cancer Therapies," Nature Reviews Clinical Oncology, vol. 8, Mar. 2011, pp. 135-141.
International Preliminary Report on Patentability mailed Jun. 13, 2019, issued in corresponding International Application No. PCT/US2017/064335, filed Dec. 1, 2017, 10 pages.
International Search Report and Written Opinion mailed Jul. 30, 2018, issued in corresponding International Application No. PCT/US2017/064335, filed Dec. 1, 2017, 14 pages.
Kolluri, S. K., et al., "A Short Nur77-Derived Peptide Converts Bcl-2 From a Protector to a Killer," Cancer Cell 14(4):285-298, Oct. 2008.
Yan H., et al., "Methotrexate Induces Apoptosis of Postpartum Placental Cytotrophoblasts," Cells Tissues Organs 203(4):231-242, 2017.

* cited by examiner

*Primary Examiner* — Sarah Pihonak
(74) *Attorney, Agent, or Firm* — Christensen O'Connor Johnson Kindness PLLC

(57) ABSTRACT

Methods for inducing growth inhibition or apoptosis of Bcl-2-expressing cells and treatments of Bcl-2 expressing cancers are provided. Additionally, assays for agents that can induce apoptosis of Bcl-2 expressing cells are disclosed.

3 Claims, 52 Drawing Sheets

Specification includes a Sequence Listing.

SMALL MOLECULE Bcl-2 FUNCTIONAL CONVERTERS AS CANCER THERAPEUTICS

CROSS-REFERENCE TO RELATED APPLICATION

This application is a continuation of application Ser. No. 16/465,971, which is the U.S. national phase of PCT/US2017/064335 filed on Dec. 1, 2017, which claims the benefit of Provisional Application No. 62/428,864, filed Dec. 1, 2016, each of which is expressly incorporated herein by reference in its entirety.

STATEMENT OF GOVERNMENT LICENSE RIGHTS

This invention was made with government support under W81XWH-12-1-0069 awarded by the U.S. ARMY Medical Research and Materiel Command and under W81XWH-08-1-0600 awarded by the U.S. ARMY Medical Research and Materiel Command. The government has certain rights in this invention.

STATEMENT REGARDING SEQUENCE LISTING

The Sequence Listing XML associated with this application is provided in XML format and is hereby incorporated by reference into the specification. The name of the XML file containing the sequence listing is 3014-P5USCON_Seq_List_20221121.XML. The XML file is 3 KB; was created on Nov. 21, 2022; and is being submitted electronically via Patent Center with the filing of the specification.

BACKGROUND OF THE INVENTION

The Bcl-2 family of proteins plays a major role in tumorogenesis. Bcl-2 proteins are characterized based on the presence of Bcl-2 homology (BH) domains. The anti-apoptotic proteins contain all the BH1-4 domains; the pro-apoptotic proteins contain either the BH3 domain only or multiple BH domains. The BH3 domain is necessary in executing the pro apoptotic function of these proteins. In anti-apoptotic proteins, the BH3 domain remains hidden or buried inside other BH domains and hence they exclusively function as protectors of cell survival. The Bcl-2 proteins use BH domains to interact with each other. The anti-apoptotic Bcl-2 proteins interact with pro-apoptotic members and inhibit their function to maintain cellular homeostasis. It is the shift in balance between anti-apoptotic and pro-apoptotic Bcl-2 proteins that may decide the fate of cancer cells.

Cancer therapeutics targeting the Bcl-2 family mainly have focused on neutralizing one or more anti-apoptotic members by inhibiting their function using small molecule inhibitors or by suppressing their expression utilizing antisense oligonucleotides. The concept was to inhibit the anti-apoptotic Bcl-2 members' function and thus allowing pro-apoptotic members to induce cell death in cancer cells. However, cancer cells treated with Bcl-2 inhibitors were found to upregulate other anti-apoptotic Bcl-2 or non-Bcl-2 family proteins involved in cell survival, resulting in therapeutic resistance.

There is a need for therapeutic agents that can selectively induce cell death in tumors with increased expression of Bcl-2, such as breast cancers, lung cancers, and lymphoma. This invention is intended to fill this unmet need by identifying small molecules that can selectively convert an anti-apoptotic Bcl-2 into its pro-apoptotic version thus providing methods of inducing apoptosis in Bcl-2 overexpressing tumors and inhibiting the growth of cancers and the progression of metastasis.

SUMMARY OF THE INVENTION

In one aspect, provided herein is a method for inducing growth inhibition or apoptosis of a Bcl-2-expressing cell, comprising contacting a Bcl-2-expressing cell with an agent that exposes the BH3 domain of Bcl-2 thereby inhibiting Bcl-2 survival function, converting Bcl-2 into a pro-apoptotic protein, and activating the intrinsic apoptosis pathway.

In some embodiments, the agent is a small molecule mimic of NuBCP-9 peptide. In certain embodiments, the agent is a methotrexate or a methotrexate analog of Formula (IV):

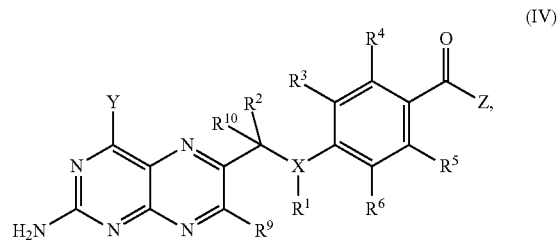

its isomer, tautomer, hydrate, or salt, wherein:
- $R^1$ is H, C1-C8 alkyl, C1-C8 alkenyl, or C1-C8 alkynyl;
- $R^2$ is H, C1-C8 alkyl, C1-C8 alkenyl, or C1-C8 alkynyl;
- $R^{10}$ is H or $R^{10}$ and $R^2$, taken together, form an oxo group (=O);
- $R^3$, $R^4$, $R^5$, and $R^6$ are independently H, halogen, C1-C8 alkyl, C1-C8 alkenyl, C1-C8 alkynyl, or $R^5$ and $R^6$, together with the carbon atoms to which each is attached, form a 5 or 6-membered aromatic or heteroaromatic ring;
- $R^9$ is H or $R^9$ and $R^1$ form a C1-C3 alkylene;
- Y is $NH_2$ or OH;
- X is N or C; and Z is OH, $NH_2$, $OR^8$, or

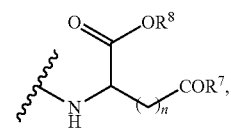

wherein $R^8$ is H or C1-C8 alkyl, n is 1 or 2, and R7 is H, OH, $NH_2$, or C1-C8 alkyl.

In some embodiments, the methotrexate analog is a compound having a structure of any one of Formulae 1-12 (e.g., compounds of Table 6). In other embodiments, the agent is a compound of Table 1, Table 2, Table 3, Table 4, or Table 5 or a compound of Formulae (I), (II), or (III):

Formula (I)

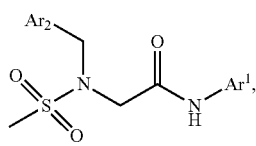

its isomer, tautomer, hydrate, or salt,
wherein:
Ar¹ is optionally substituted C6-C10 aryl or optionally substituted C5-C10 heteroaryl; and
Ar² is H, optionally substituted C6-C10 aryl, or optionally substituted C5-C10 heteroaryl, Formula (II)

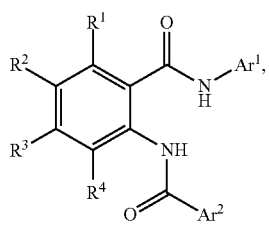

its isomer, tautomer, hydrate, or salt,
wherein:
Ar¹ is optionally substituted C6-C10 aryl or optionally substituted C5-C10 heteroaryl;
Ar² is optionally substituted C6-C10 aryl, or optionally substituted C5-C10 heteroaryl; and
$R^1$, $R^2$, $R^3$, and $R^4$ are independently H, halogen, optionally substituted C1-C8 alkyl, optionally substituted C1-C8 alkenyl, optionally substituted C1-C8 alkynyl, O(C1-C8 alkyl), or C(O)NHR, wherein R is optionally substituted C1-C8 alkyl, optionally substituted C6-C10 aryl, or optionally substituted C5-C10 heteroaryl
or Formula (III):

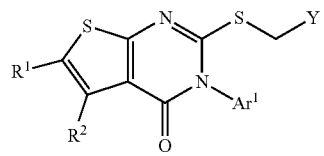

its isomer, tautomer, hydrate, or salt,
wherein:
Ar¹ is optionally substituted C6-C10 aryl or optionally substituted C5-C10 heteroaryl;
$R^1$ and $R^2$ are independently H, halogen, optionally substituted C1-C8 alkyl, optionally substituted C1-C8 alkenyl, optionally substituted C1-C8 alkynyl, O(C1-C8 alkyl), or C(O)NHR, wherein R is optionally substituted C1-C8 alkyl, optionally substituted C6-C10 aryl, or optionally substituted C5-C10 heteroaryl; or together with the carbon atoms to which each is attached, $R^1$ and $R^2$ form an optionally substituted 6-membered cycle;

Y is COOH, CONH₂, optionally substituted C6-C10 aryl, optionally substituted C5-C10 heteroaryl, or C(O)X; and X is optionally substituted C6-C10 aryl, optionally substituted C5-C10 heteroaryl, or optionally substituted C3-C10 heteroaryl.

In a second aspect, provided herein is a method of treating Bcl-2-expressing cancer in a subject, comprising administering to a subject in need of cancer treatment, a therapeutically effective amount of an agent that exposes the BH3 domain of Bcl-2 thereby converting Bcl-2 into a pro-apoptotic protein.

In some embodiments, the agent is a small molecule mimic of NuBCP-9 peptide. In certain embodiments, the agent is a methotrexate or a methotrexate analog of Formula (IV):

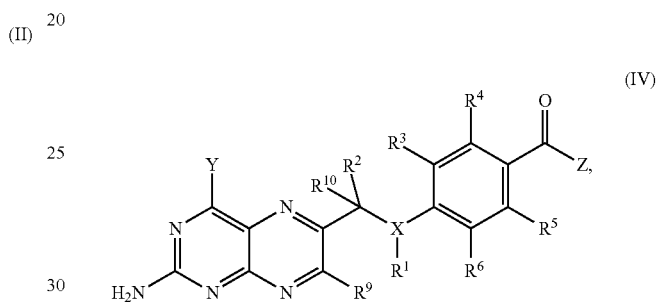

its isomer, tautomer, hydrate, or salt,
wherein:
$R^1$ is H, C1-C8 alkyl, C1-C8 alkenyl, or C1-C8 alkynyl;
$R^2$ is H, C1-C8 alkyl, C1-C8 alkenyl, or C1-C8 alkynyl;
$R^{10}$ is H or $R^{10}$ and $R^2$, taken together, form an oxo group (=O);
$R^3$, $R^4$, $R^5$, and $R^6$ are independently H, halogen, C1-C8 alkyl, C1-C8 alkenyl, C1-C8 alkynyl, or $R^5$ and $R^6$, together with the carbon atoms to which each is attached, form a 5 or 6-membered aromatic or heteroaromatic ring;
$R^9$ is H or $R^9$ and $R^1$ form a C1-C3 alkylene;
Y is NH₂ or OH;
X is N or C; and Z is OH, NH₂, $OR^8$, or

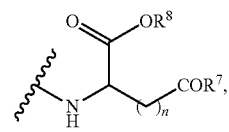

wherein $R^8$ is H or C1-C8 alkyl, n is 1 or 2, and R7 is H, OH, NH₂, or C1-C8 alkyl.

In some embodiments, the methotrexate analog is a compound having a structure of any one of Formulae 1-12. In other embodiments, the agent is a compound of Table 1, Table 2, Table 3, Table 4, or Table 5 or a compound of Formulae (I), (II), or (III):

Formula (II)

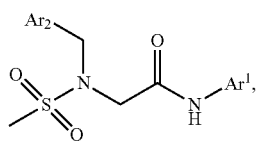
(I)

its isomer, tautomer, hydrate, or salt,
wherein:
  $Ar^1$ is optionally substituted C6-C10 aryl or optionally substituted C5-C10 heteroaryl; and
  $Ar^2$ is H, optionally substituted C6-C10 aryl, or optionally substituted C5-C10 heteroaryl, Formula (II)

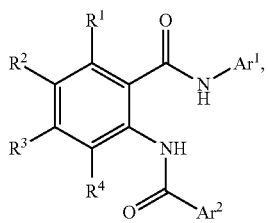
(II)

its isomer, tautomer, hydrate, or salt,
wherein:
  $Ar^1$ is optionally substituted C6-C10 aryl or optionally substituted C5-C10 heteroaryl;
  $Ar^2$ is optionally substituted C6-C10 aryl, or optionally substituted C5-C10 heteroaryl; and
  $R^1$, $R^2$, $R^3$, and $R^4$ are independently H, halogen, optionally substituted C1-C8 alkyl, optionally substituted C1-C8 alkenyl, optionally substituted C1-C8 alkynyl, O(C1-C8 alkyl), or C(O)NHR, wherein R is optionally substituted C1-C8 alkyl, optionally substituted C6-C10 aryl, or optionally substituted C5-C10 heteroaryl
or Formula (III):

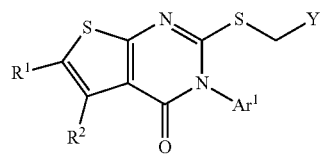
(III)

its isomer, tautomer, hydrate, or salt,
wherein:
  $Ar^1$ is optionally substituted C6-C10 aryl or optionally substituted C5-C10 heteroaryl;
  $R^1$ and $R^2$ are independently H, halogen, optionally substituted C1-C8 alkyl, optionally substituted C1-C8 alkenyl, optionally substituted C1-C8 alkynyl, O(C1-C8 alkyl), or C(O)NHR, wherein R is optionally substituted C1-C8 alkyl, optionally substituted C6-C10 aryl, or optionally substituted C5-C10 heteroaryl; or together with the carbon atoms to which each is attached, $R^1$ and $R^2$ form an optionally substituted 6-membered cycle;

Y is COOH, $CONH_2$, optionally substituted C6-C10 aryl, optionally substituted C5-C10 heteroaryl, or C(O)X; and X is optionally substituted C6-C10 aryl, optionally substituted C5-C10 heteroaryl, or optionally substituted C3-C10 heteroaryl.

In some embodiments, the cancer is breast cancer, blood cancer, lymphoma, or lung cancer. In certain embodiments, the cancer is non-small cell lung cancer or triple negative breast cancer.

In certain embodiments, the methods of cancer treatment disclosed herein comprise administering, e.g., co-administering or sequentially administering, an effective amount of an agent that increases Bcl-2 expression. In other embodiments, the methods of cancer treatment disclosed herein are used in combination with radiation therapy. In yet other embodiments, the methods of cancer treatment disclosed herein further comprising administering a folate or leucovorin.

In some embodiments of the methods of cancer treatment disclosed herein, the cancer is chemotherapy-resistant cancer.

In a third aspect, provided herein is a method of screening for an agent that converts Bcl-2 from an anti-apoptotic protein into a pro-apoptotic protein, comprising:
  (a) contacting a first population of cells with an agent, wherein the first population of cells expresses or over-expresses Bcl-2;
  (b) determining the cell viability of the first population of cells;
  (c) contacting a second population cells with the agent, wherein the second population of cells has no expression of Bcl-2 or expression of Bcl-2 lower than the Bcl-2 or expression of first cell population; and
  (d) determining the cell viability of the second population of cells;
  (e) comparing the cell viability of the first and second populations of cells to determine whether the agent converts Bcl-2 from an anti-apoptotic protein into a pro-apoptotic protein.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

Figure 13A:
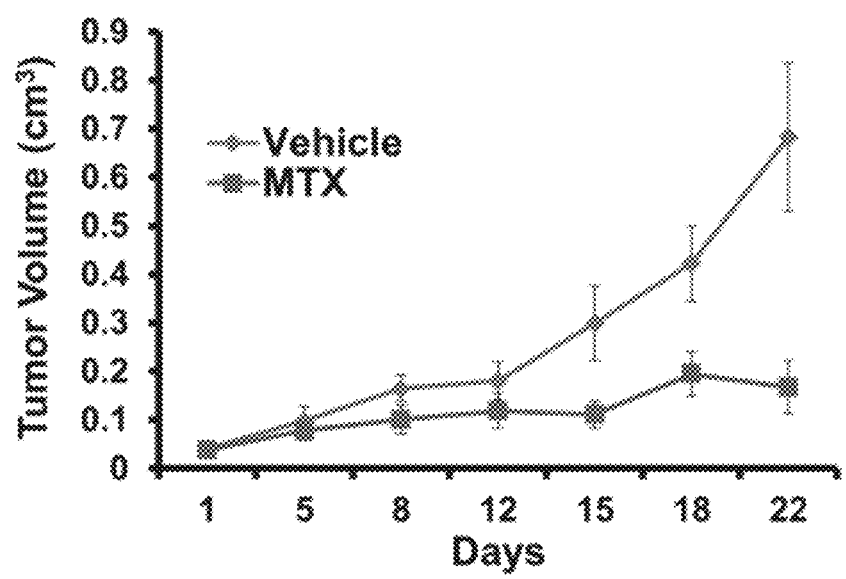
FIG. 13A demonstrates anti-tumor effects of methotrexate in vivo. About MDA-MB231/Bcl-2 cells were implanted in the mammary fat pad of NOD SCID mice (N=10). Once palpable tumors were formed MTX was treated at 100 mg/kg twice a week by intraperitoneal injections. Tumor measurements were made with digital calipers twice a week.
Figure 13B:
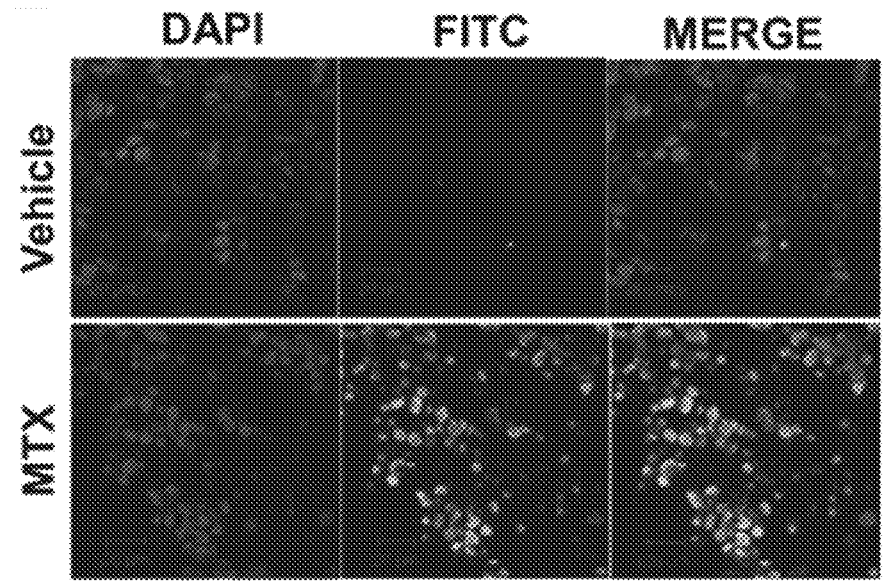

FIG. 13B shows IHC performed on frozen sections. TUNEL assay was performed as per manufacturer's protocol.

Figure 13C:
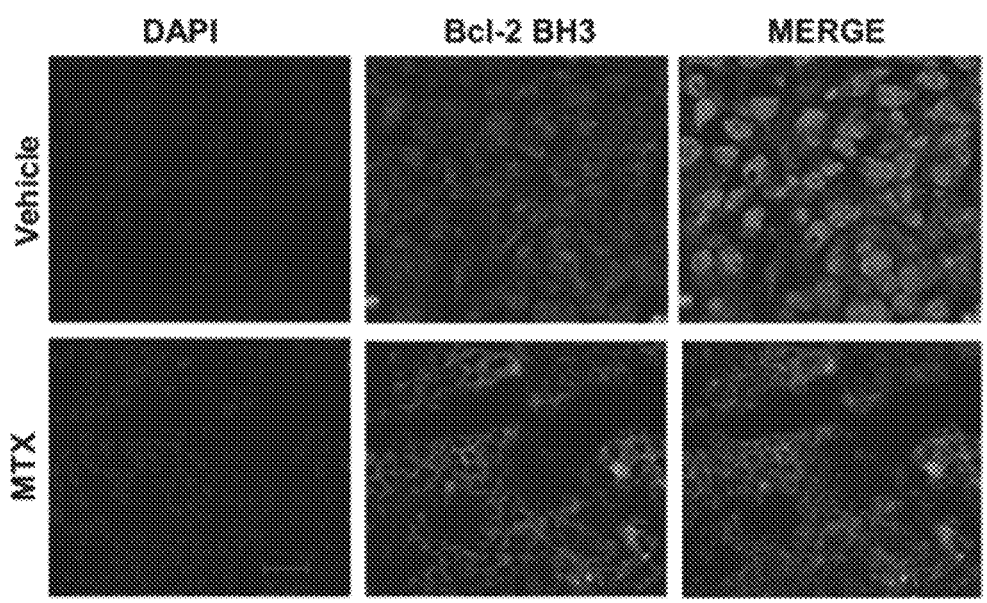

FIG. 13C shows that Bcl-2 conformational change was detected using a validated antibody for detecting Bcl-2 BH3 domain.

Figure 13D:
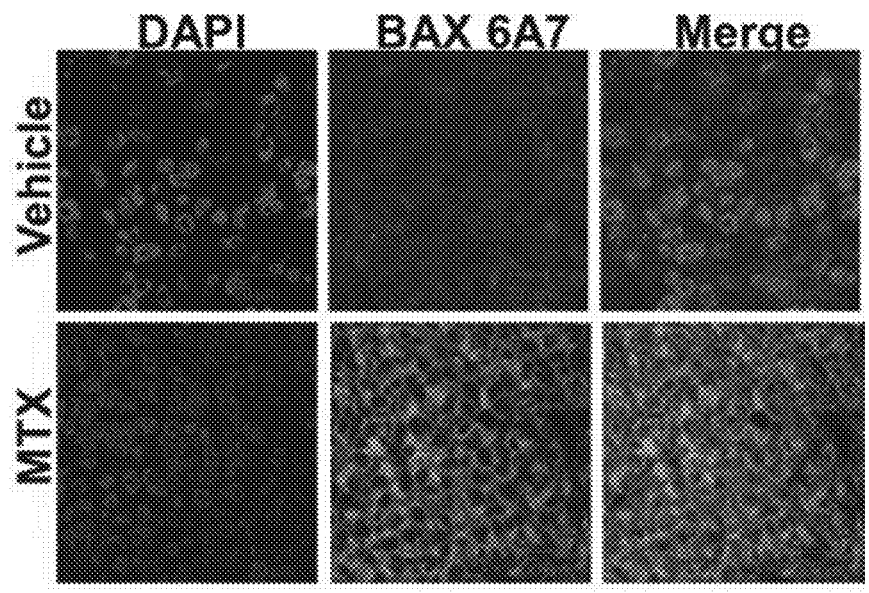

FIG. 13D shows that activated Bax was detected using the BAX 6A7 antibody.

Figure 13E:
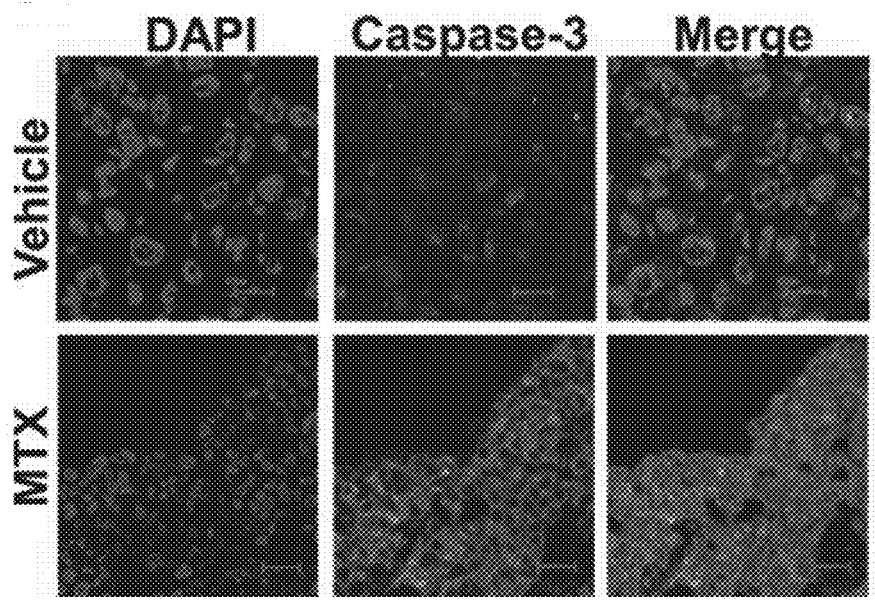

FIG. 13E shows that activated Caspase-3 was detected using Cleaved caspase-3 antibody.

Figure 14:
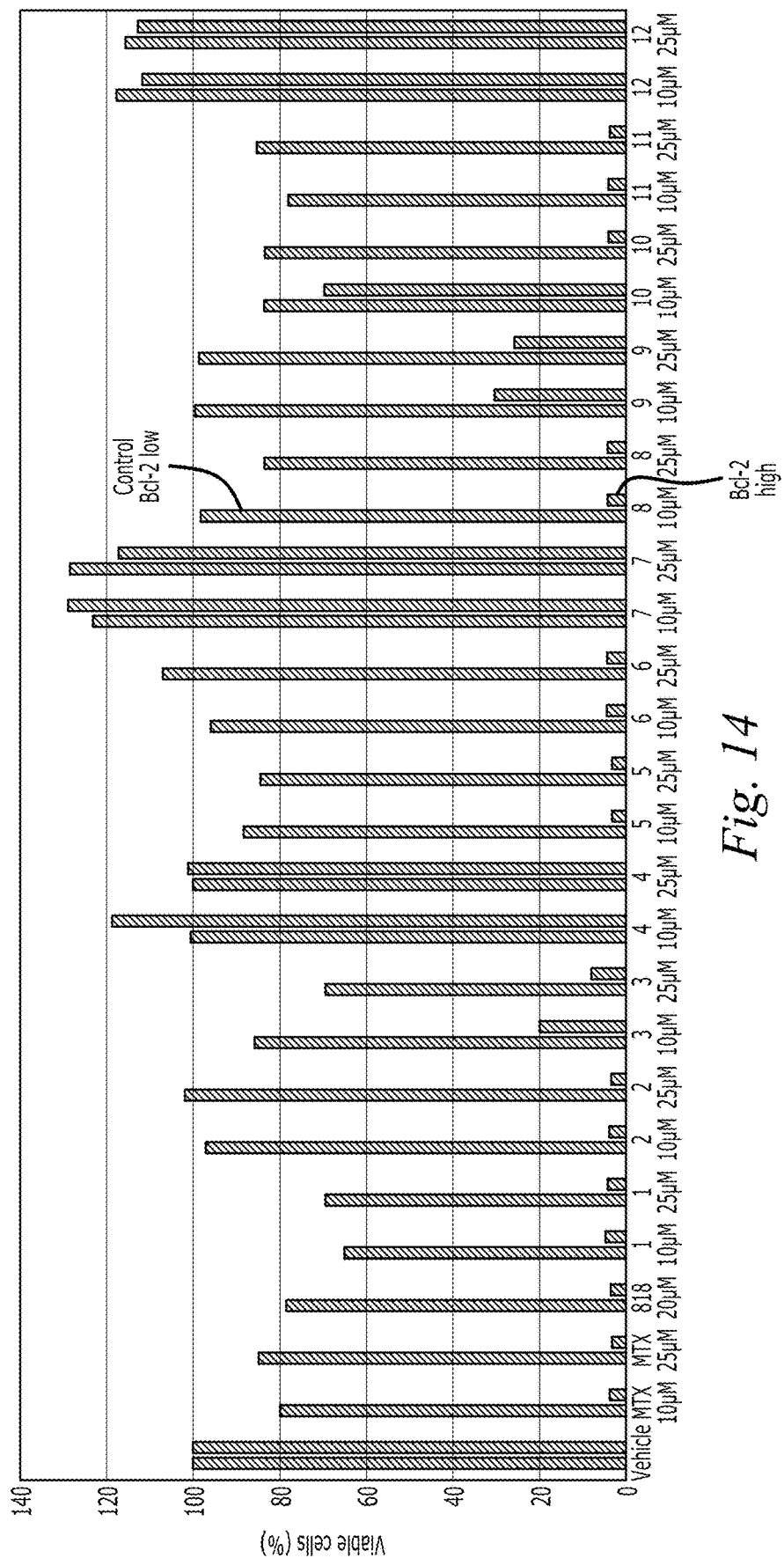

FIG. 14 demonstrates effects of methotrexate analogs in Jukat lymphoma cells: Bcl-2 low (left bars for each compound) and high expressing (right bars for each compound) Jurkat lymphoma cells were plated and treated with the indicated methotrexate analogs for 48 or 72 hours and cell viability was determined. Representative data from independent experiments is shown.

Figure 15A:
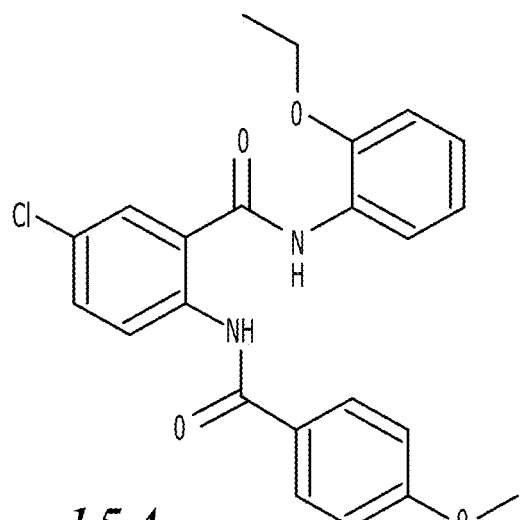

FIG. 15A shows the structure of BFC1108.

Figure 15B:
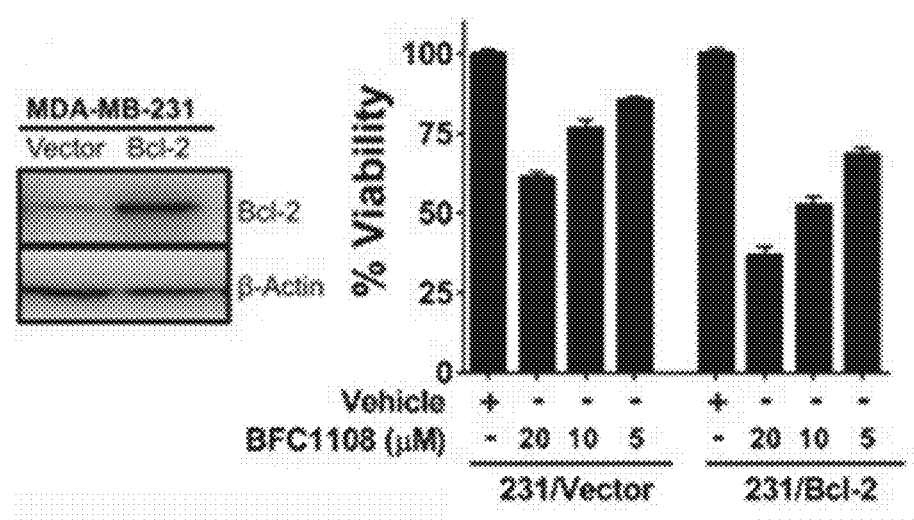

FIG. 15B demonstrates Bcl-2 dependent effects of BFC1108. Left panel: Bcl-2 expression in MDA-MB-231 cells transfected with pcDNA control vector (MDA-MB-231/Vector) or Bcl-2 expression vector (MDA-MB-231/Bcl-2) was determined by immunoblotting. Right panel: cells were exposed to BFC1108 in a medium containing 10% FBS for 48 h and viability was determined.

Figure 15C:
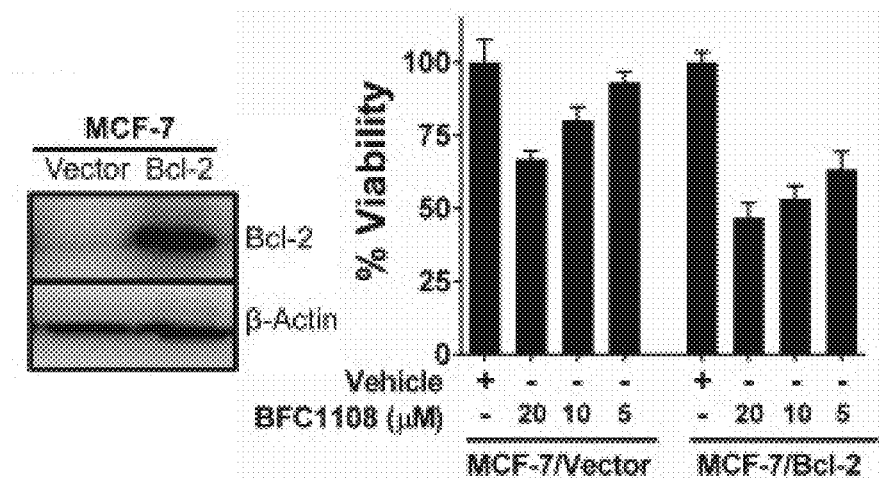

FIG. 15C demonstrates Bcl-2 dependent effects of BFC1108. Left Panel: Bcl-2 expression in MCF-7 cells transfected with pcDNA control vector (MCF-7/Vector) or BCl-2 expression vector (MCF-7/Bcl-2) was determined by immunoblotting. Right panel: cells were exposed to BFC1108 in a medium containing 10% FBS for 48 h and viability was determined.

Figure 15D:
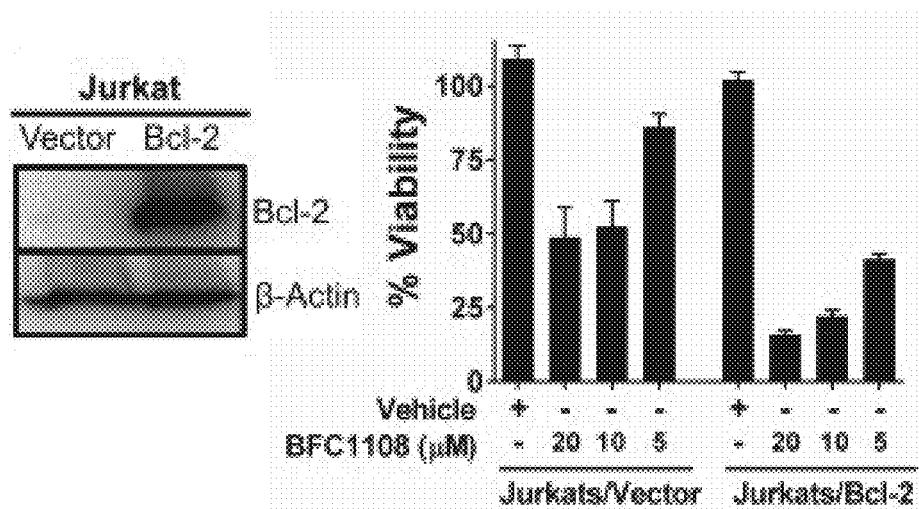

FIG. 15D demonstrates Bcl-2 dependent effects of BFC1108. Left panel: Bcl-2 expression in Jurkat cells transfected with control vector (Jurkat/Vector) or Bcl-2 expression vector (Jurkat/Bcl-2) was determined by immunoblotting. Right panel: cells were exposed to BFC1108 in a medium containing 10% FBS for 48 h and viability was determined.

Figure 15E:
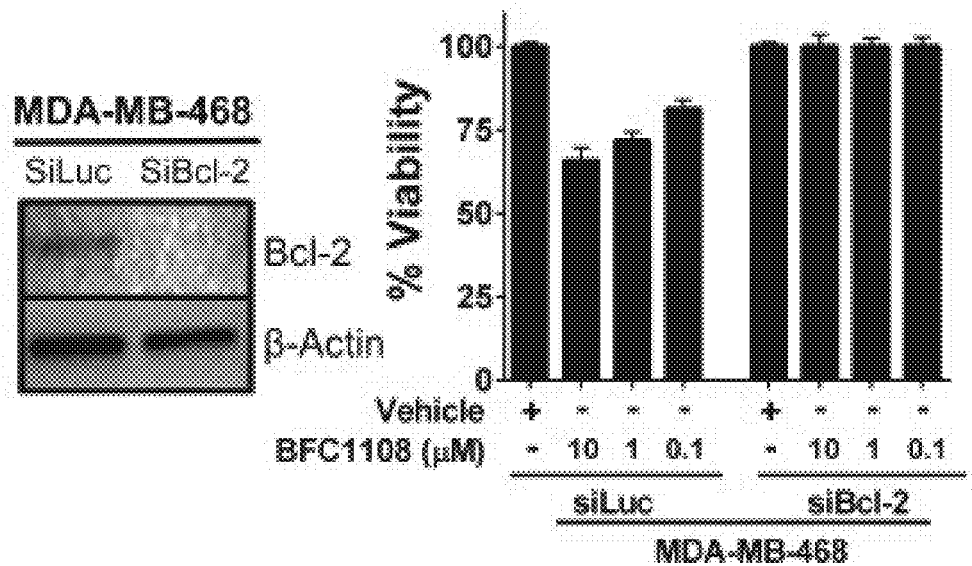

FIG. 15E demonstrates Bcl-2 dependent effects of BFC1108. Left panel: Knockdown of Bcl-2 in MDA-MB-468 cells was determined by immunoblotting. Right panel: BFC1108 was treated in a medium containing 10% FBS for 48 h in MDA-MB-468 cells with or without Bcl-2 expression.

Figure 15F:
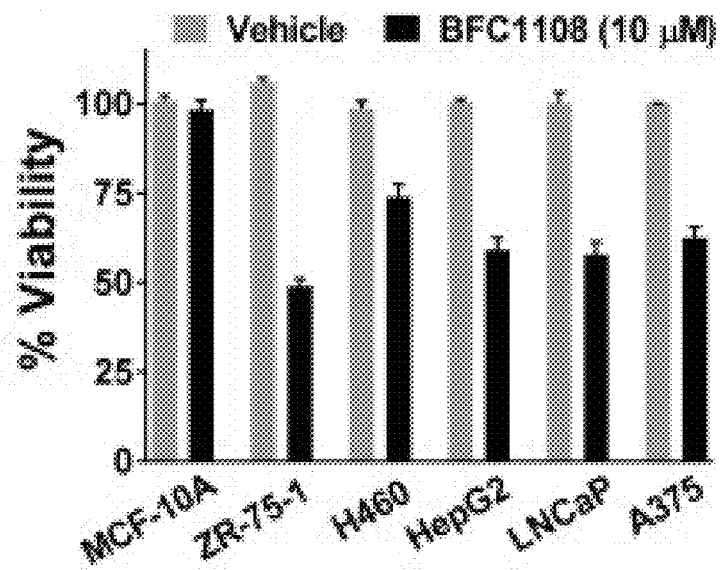

FIG. 15F demonstrates effects of BFC1108 on viability of normal mammary epithelial cells (MCF-10A) along with a range of cancer cell types when treated for 48 h at 10% serum conditions using cell titer glo assay.

Figure 16A:
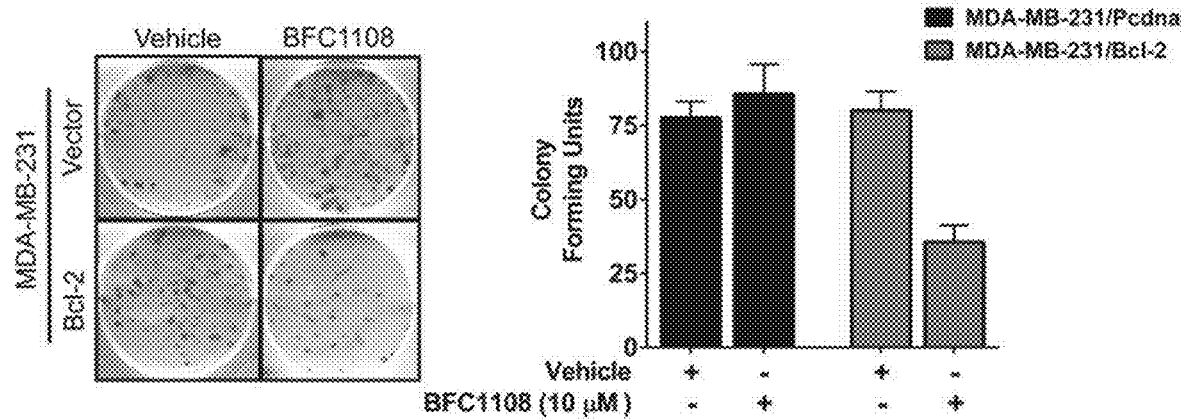

FIG. 16A shows effect of BFC1108 on clonogenic survival of MDA-MB-231/Vector and MDA-MB-231/Bcl-2 cells at 10 μM concentration in medium containing 10% FBS for 48 h and continuing the colony formation for 2 weeks.

Figure 16B:
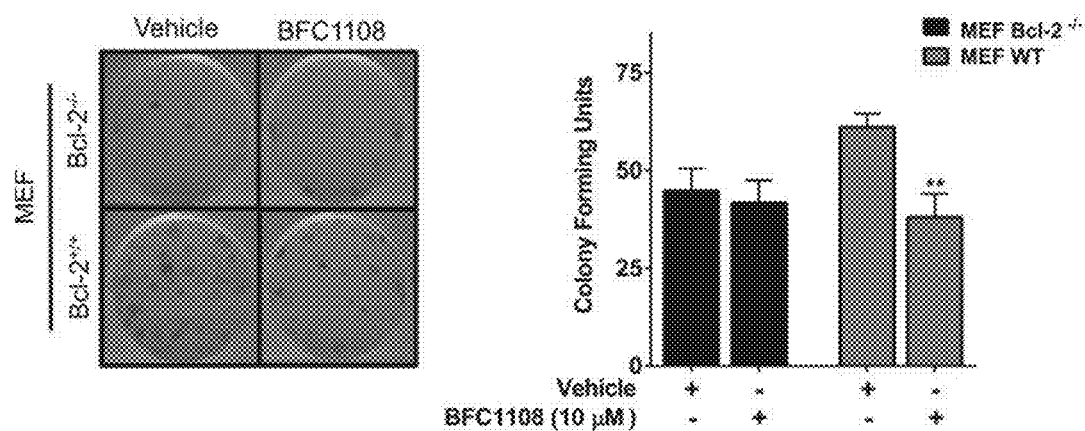

FIG. 16B shows the effect of BFC1108 on the colony forming ability of MEF Bcl-2-/- and WT MEF cells which was determined in a medium containing 10% FBS for 48 h.

Figure 16C:
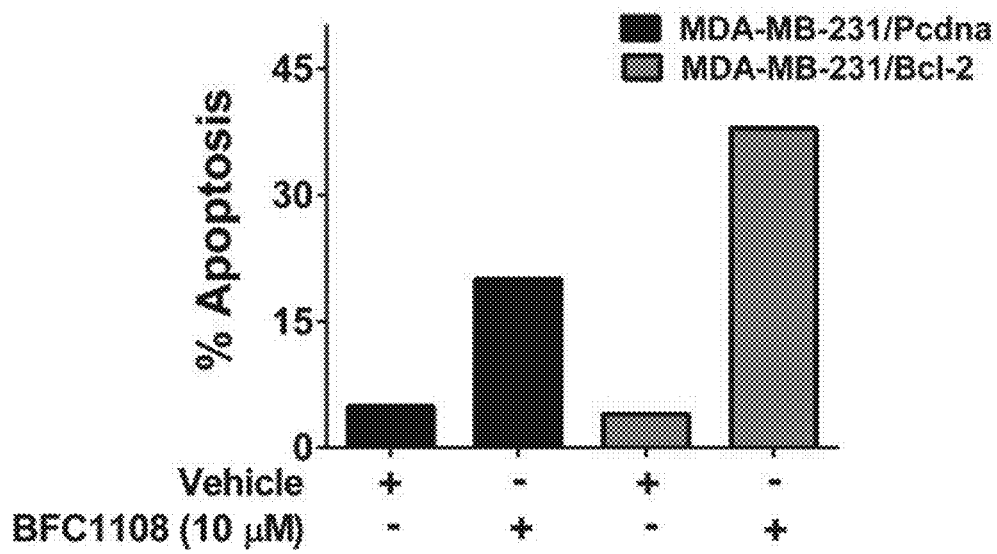

FIG. 16C are MDA-MB-231 cells with or without BCl-2 expression was treated with 10 μM BFC1108 in a medium containing 10% FBS for 48 h and apoptosis was determined by annexin v staining.

Figure 17A:
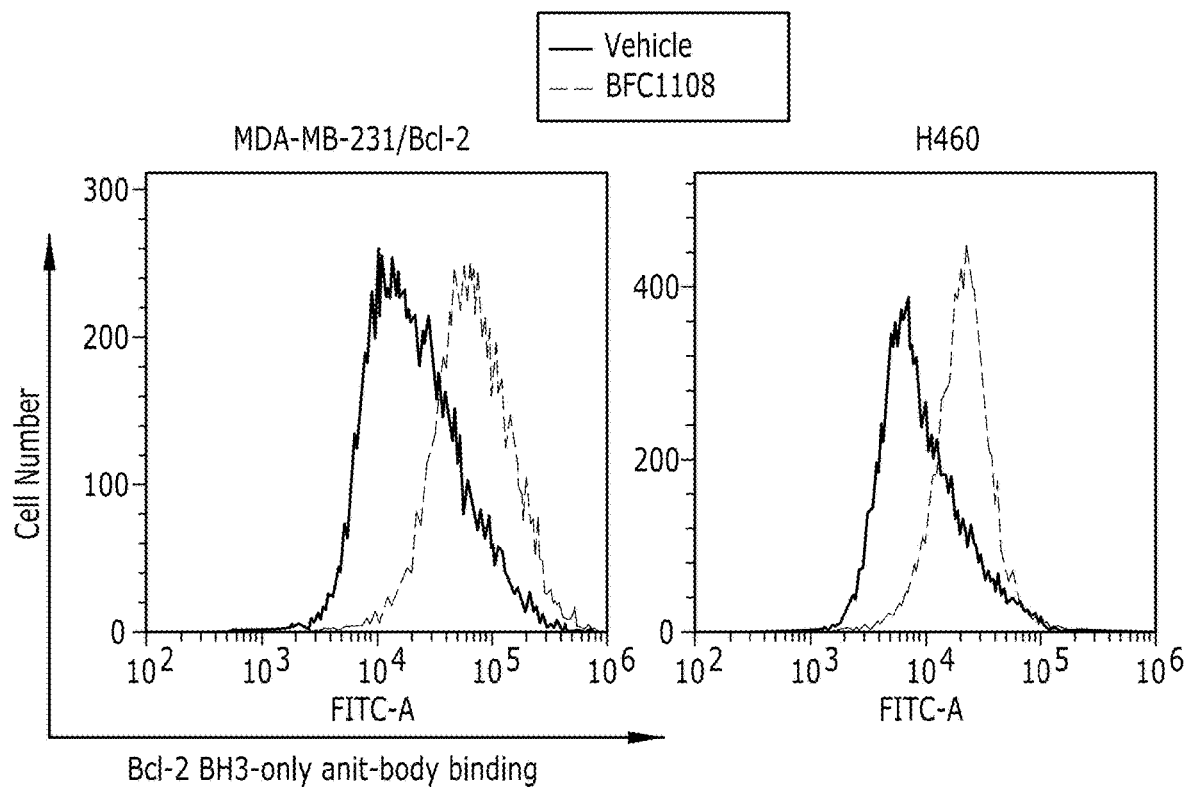

FIG. 17A demonstrates mechanism of action of BFC1108. MDA-MB-231/Bcl-2 cells were exposed to BFC1108 at 10 μM concentration for 48 h in a medium containing 10% serum. Change in conformation of Bcl-2 was determined by using Bcl-2 BH3 antibody followed by flow cytometric analysis.

Figure 17B:
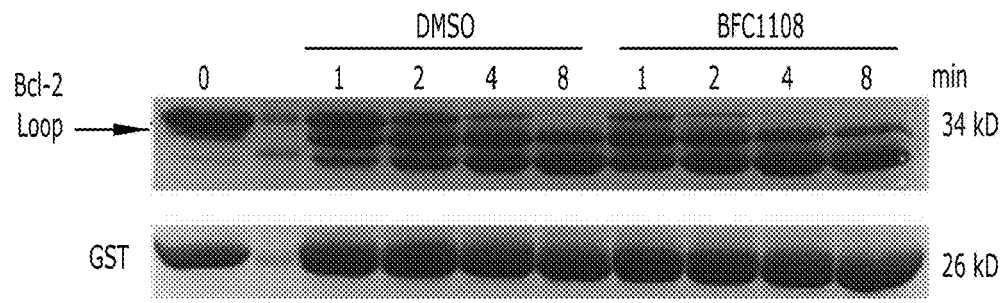

FIG. 17B shows limited proteolysis of BCl-2 loop domain in the presence of BFC1108. Purified GST tagged Bcl-2 loop domain was incubated with 50 μM BFC1108 at the indicated times to determine if BFC1108 interaction with loop domain has an effect on the proteolysis pattern upon co-incubation with trypsin.

Figure 17C:
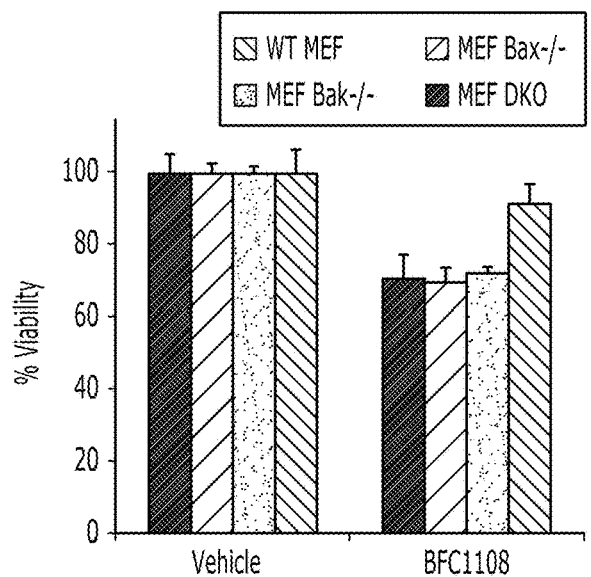

FIG. 17C WT MEF, Bax-/- MEF, Bak-/- MEF and Bax-/- Bak-/- MEF cells were treated with 1 μM BFC1108 for 24 h in 10% FBS medium and viability was assessed using cell titer glo assay.

Figure 17D:
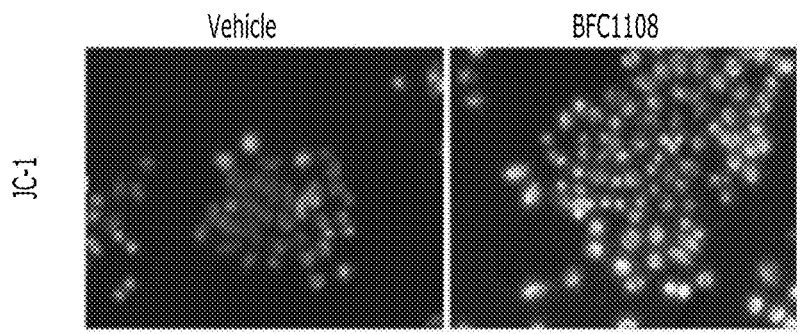

FIG. 17D JC-1 stain was used to stain live H460 cells that were treated with 10 μM BFC1108 for 16 h in 10% FBS containing medium and images taken with FITC and rhodamine filters were overlaid. Cells stained orange have intact mitochondrial outer membrane and the ones turning green have compromised outer membrane indicating loss of membrane potential.

Figure 18A:
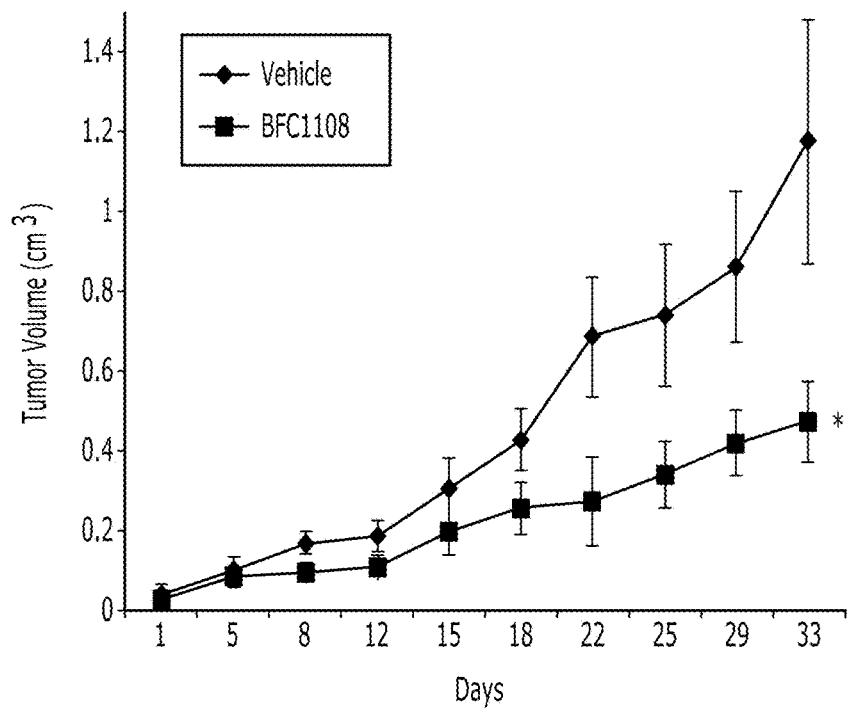

FIG. 18A shows anti-tumor effects of BFC1108 an orthotopic breast cancer model. 106 MDA-MB-231/Bcl-2 cells were implanted in the mammary fat pad of NOD.SCID mice (n=8 per group). Once palpable tumors formed, mice were treated with 100 mg/kg BFC1108 twice a week by i.p. route. Tumor measurements were made with digital calipers twice a week.

Figure 18B:
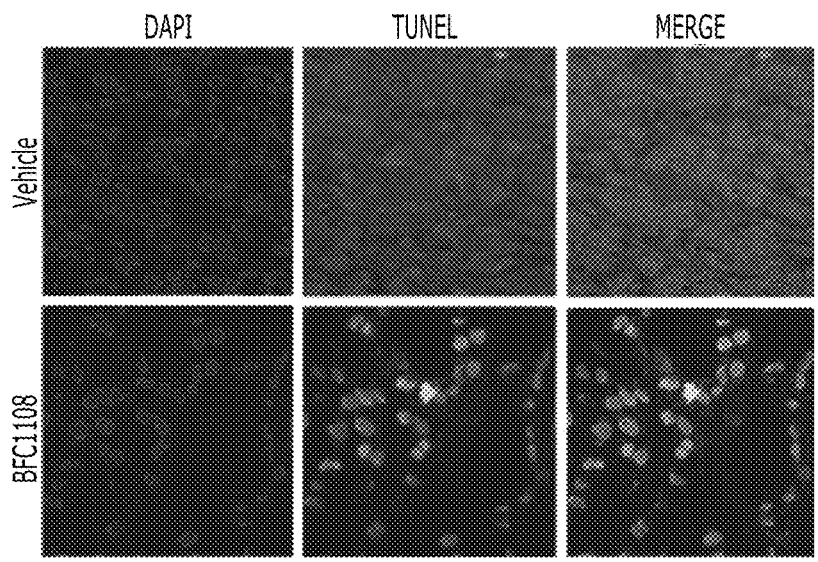

FIG. 18B shows IHC that was performed on frozen sections to determine apoptosis using TUNEL stain.

Figure 18C:
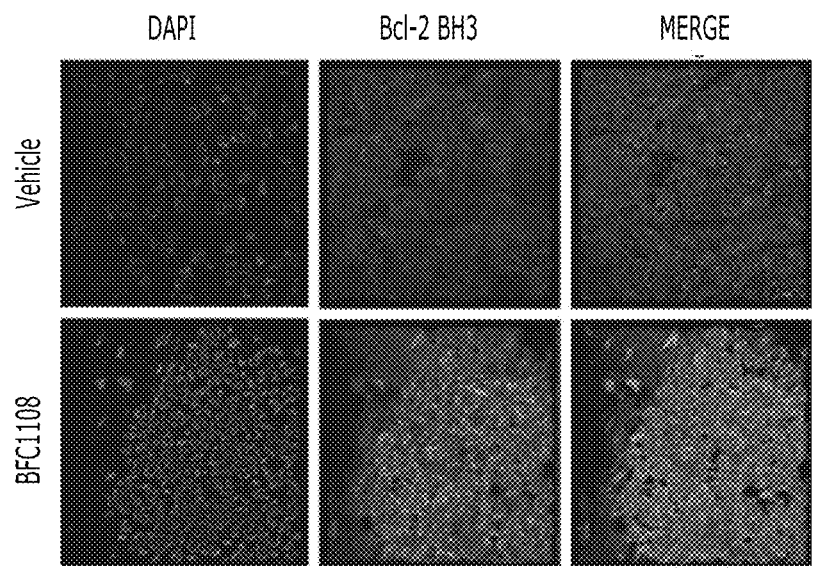

FIG. 18C demonstrates Bcl-2 conformation change was detected by staining with Bcl-2 BH3 only antibody.

Figure 18D:
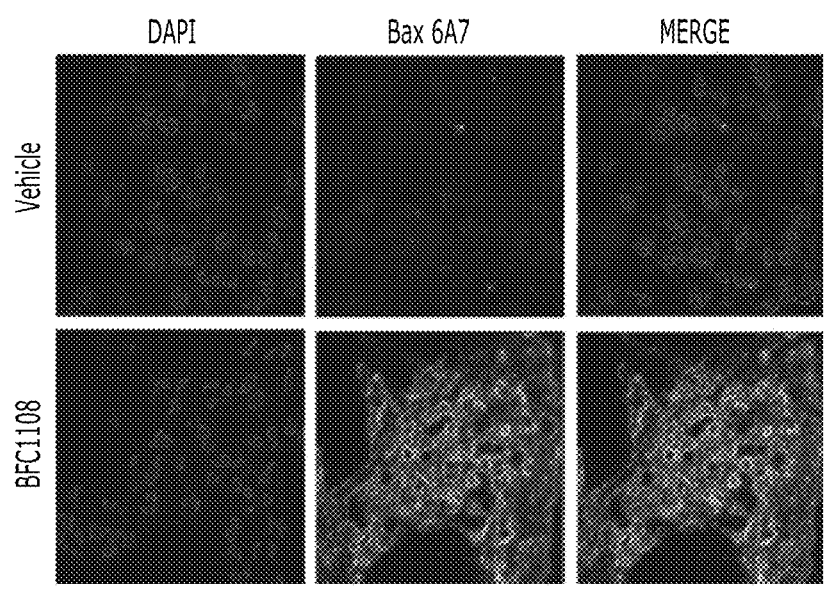

FIG. 18D demonstrates that activated Bax was detected using Bax 6A7 antibody.

Figure 18E:
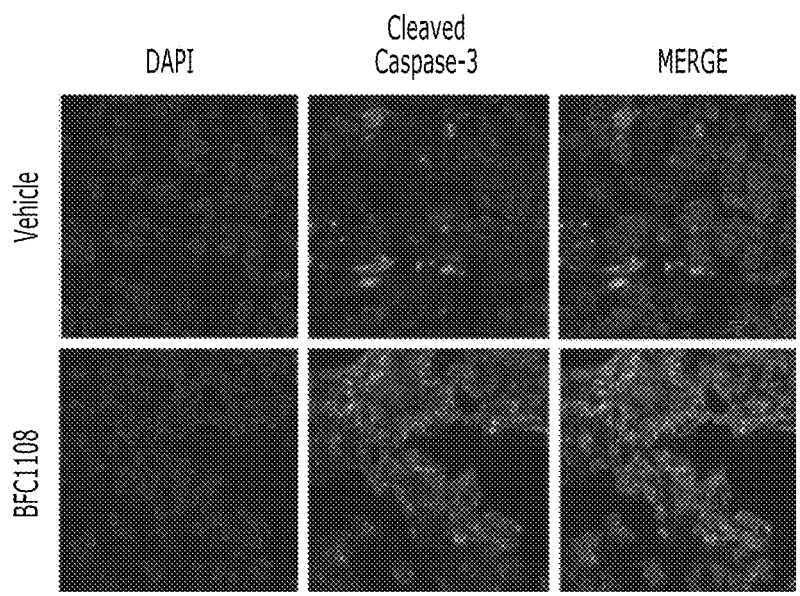

FIG. 18E demonstrates that activated caspase-3 was detected using cleaved caspase-3 antibody.

Figure 19A:
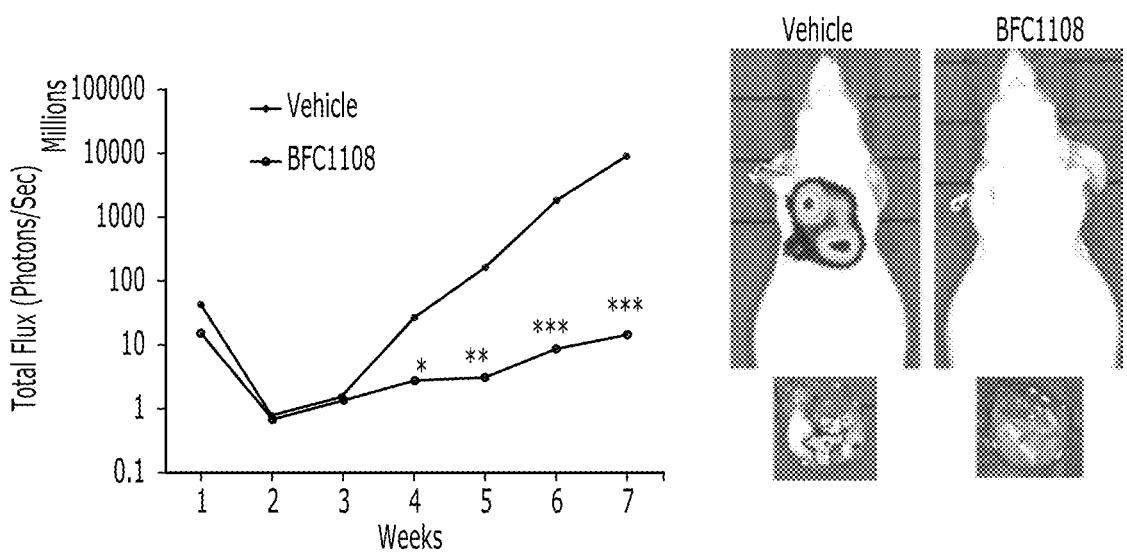

FIG. 19A About 200,000 LMD-231 cells stably expressing luciferase was injected into the tail vein of 6 week old nude mice. Lung metastasis was formed in 2 weeks. Mice were treated with 100 mg/kg BFC1108 4 times a week by intraperitoneal route. Bioluminescent imaging was performed once a week and quantified.

Figure 19B:
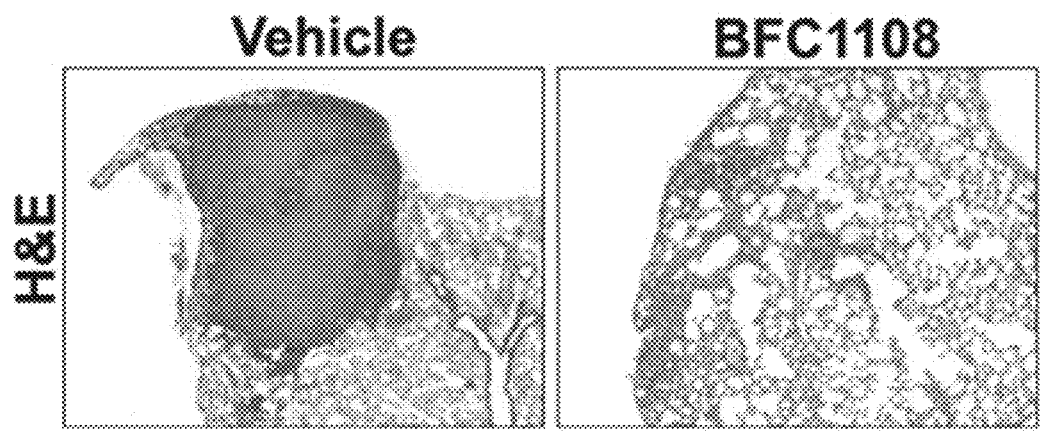

FIG. 19B demonstrates that H&E staining showing increased number of tumor cells in lung tissue of nude mice with vehicle treatment, compared to BFC1108 treatment, at the end of the study.

Figure 19C:
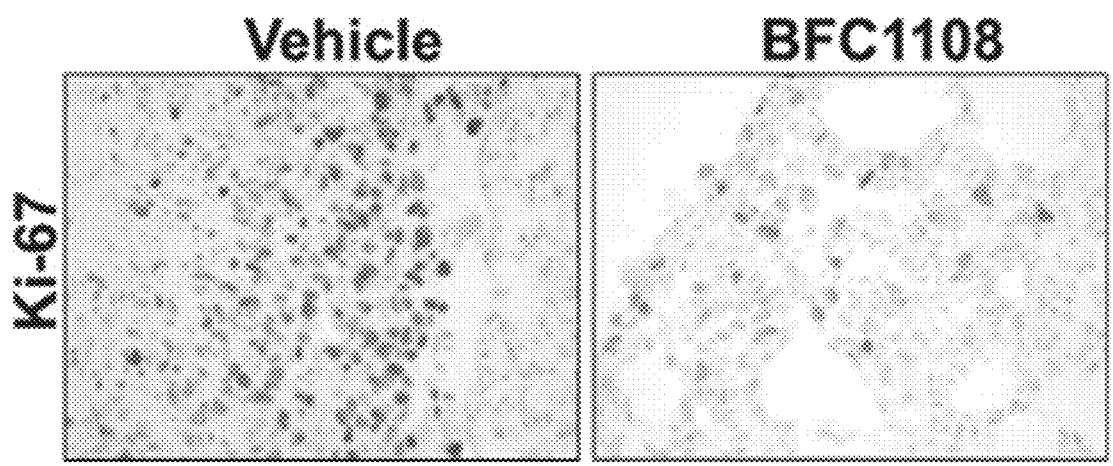

FIG. 19C depicts Ki-67 stain detecting presence of tumor cells with high proliferation in lung tissue from vehicle-treated mice, compared to lung tissue from BFC1108-treated mice.

Figure 20A:
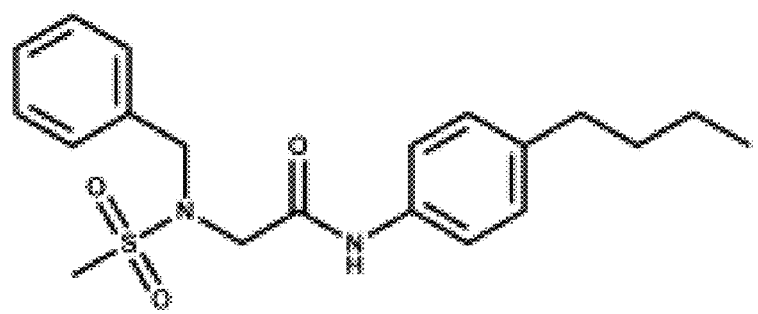 [SMILES: CCCCc1ccc(NC(=O)CN(Cc2ccccc2)S(C)(=O)=O)cc1]

FIG. 20A shows the structure of BFC1103.

Figure 20B:
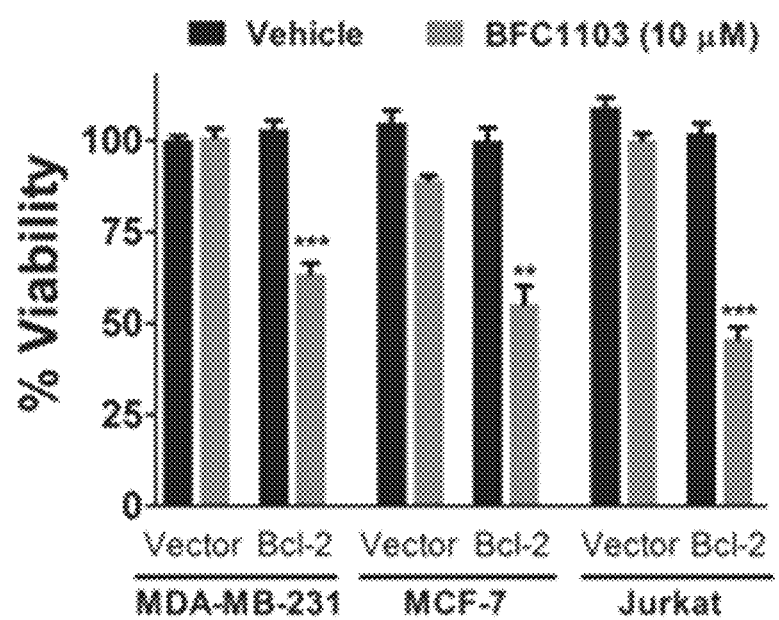

FIG. 20B Indicated cells were exposed to BFC1103 at 10 μM for 24 h at 10% serum conditions and viability was assessed by cell titer glo assay.

Figure 20C:
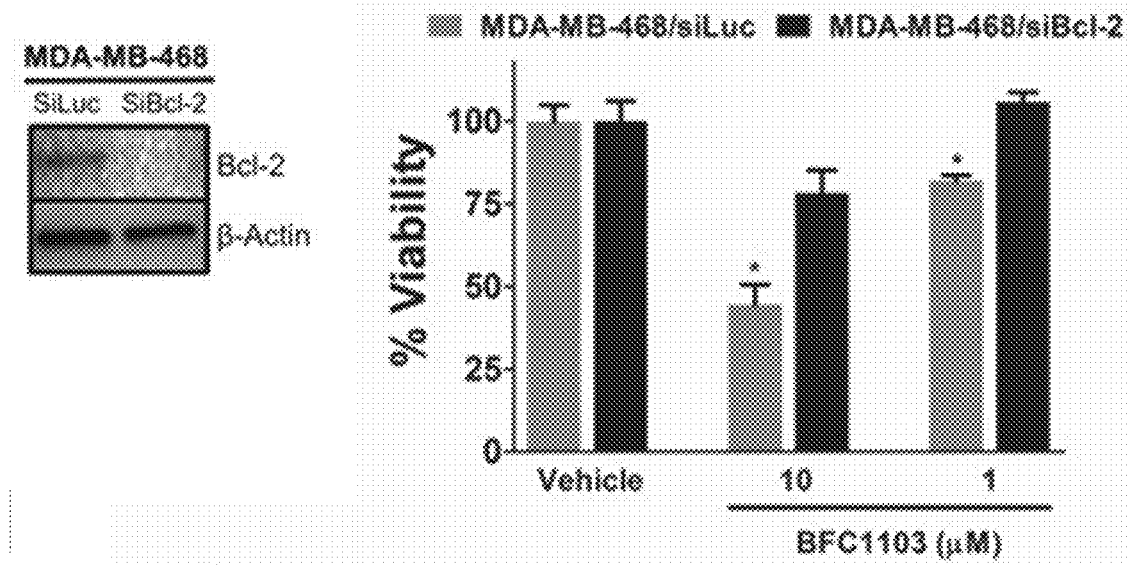

FIG. 20C demonstrates Bcl-2 dependent effects of BFC1103. Left Panel: Knockdown of Bcl-2 in MDA-MB-468 cells was determined by immunoblotting. Right Panel: Cells were exposed to BFC1103 at the indicated concentrations for 48 h at 10% FBS and viability was determined.

Figure 20D:
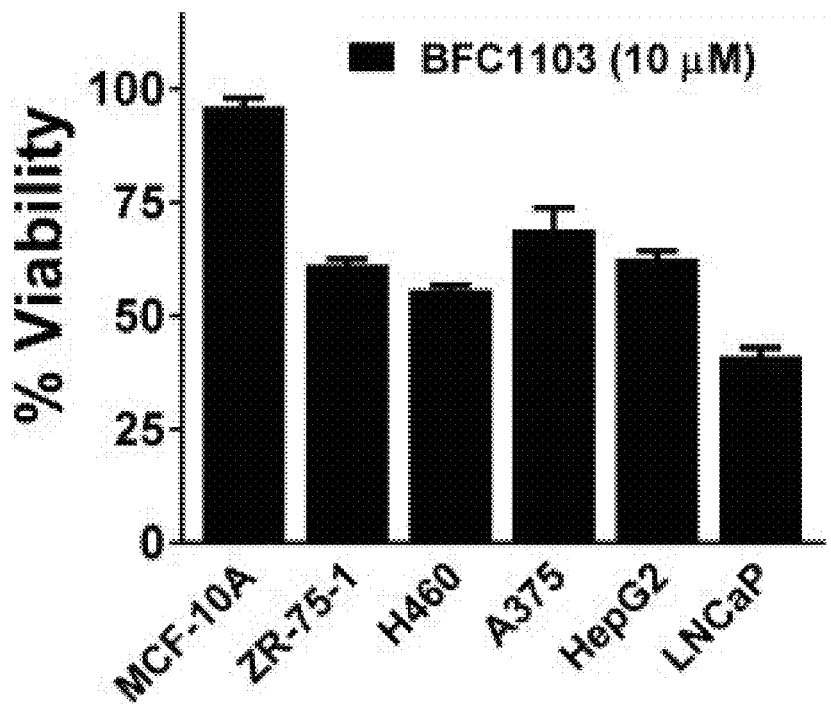

FIG. 20D demonstrates comparison of viability of various cancer cells lines with normal mammary epithelial cells, MCF-10A after treatment with BFC1103 for 24 h in medium containing 10% FBS.

Figure 21A:
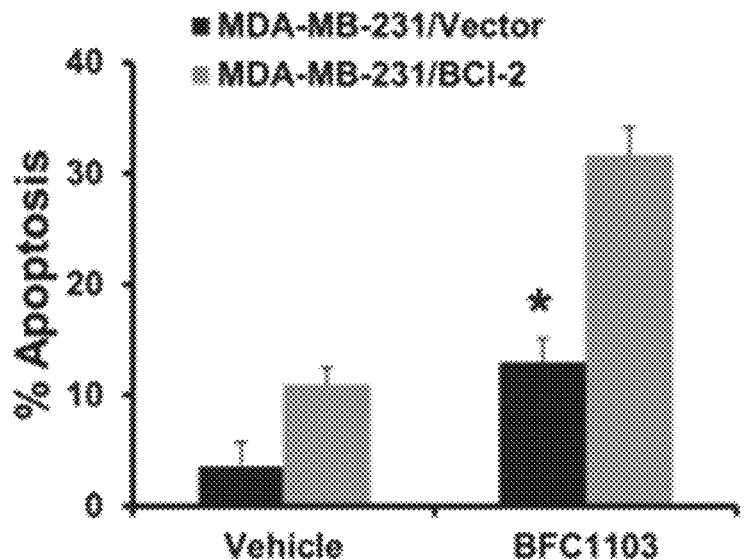

FIG. 21A demonstrates Bcl-2 dependent anti-tumorigenic effects of BFC1103. Apoptosis was determined by using nuclear fragmentation and condensation by using DAPI stain in the indicated cells. Cells were treated with BFC1103 at 10 μM for 24 h at 10% FBS-containing medium, and number of fragmented and condensed nucleus was counted under fluorescent microscope.

Figure 21B:
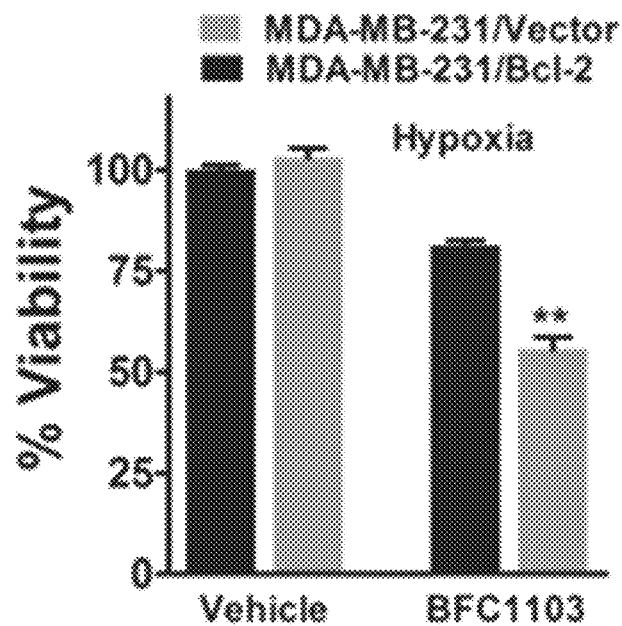

FIG. 21B demonstrates Bcl-2 dependent anti-tumorigenic effects of BFC1103. Viability was assessed using cell titer glo assay while the cells were treated under hypoxic conditions.

Figure 21C:
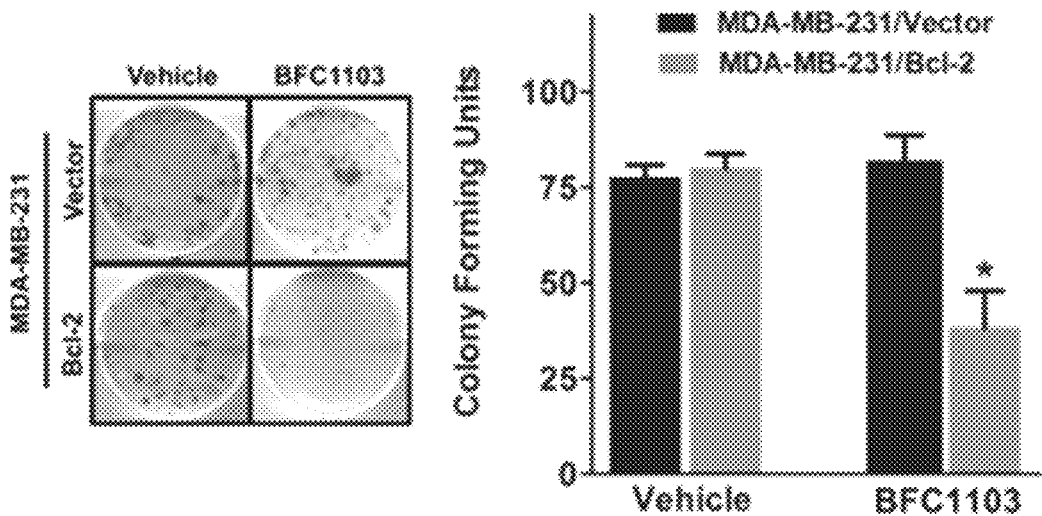

FIG. 21C shows effect of BFC1103 on clonogenic survival of MDA-MB-231/Vector and MDA-MB-231/Bcl-2 cells that were treated with 10 μM of the compound in medium containing 10% FBS for 48 h and continuing the colony formation for 2 weeks.

Figure 22A:
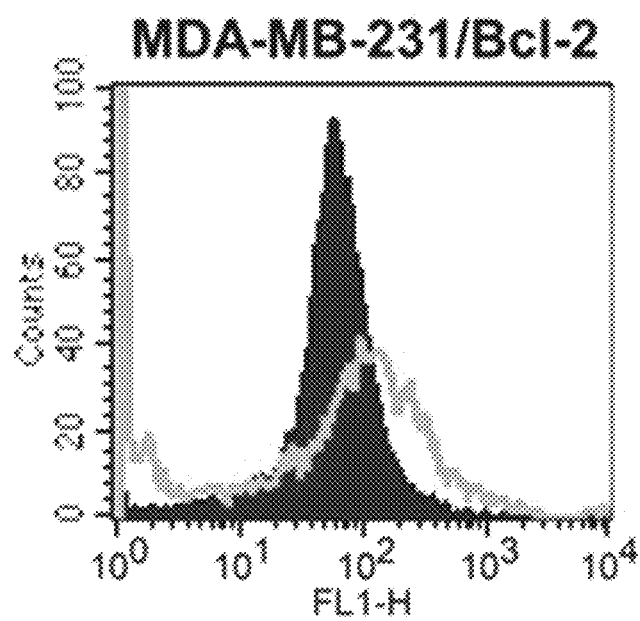

FIG. 22A shows that BFC1103 interacts with Bcl-2 and induces conformational changes in Bcl-2. MDA-MB-231/Bcl-2 cells were exposed to BFC1103 at 10 μM concentration for 48 h in a medium containing 10% serum. Change in conformation of Bcl-2 was determined by using Bcl-2 BH3 only antibody followed by flow cytometric analysis.

Figure 22B:
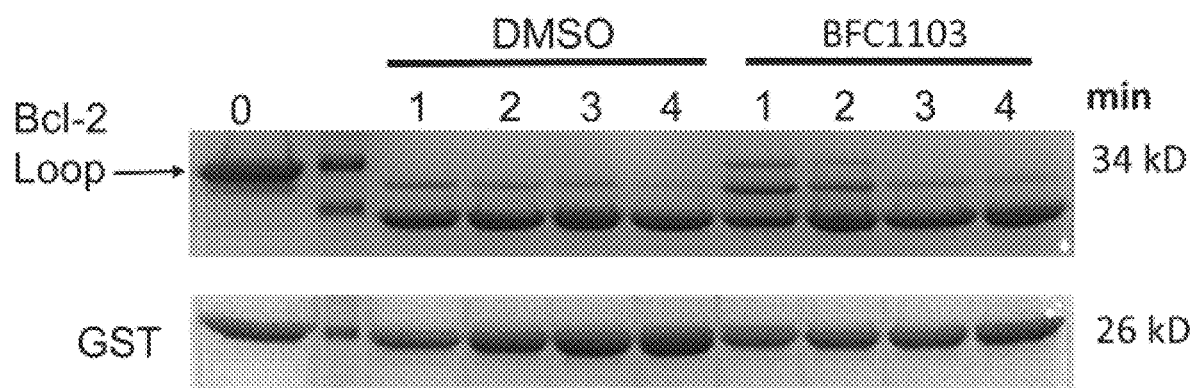

FIG. 22B depicts limited proteolysis of Bcl-2 loop domain in the presence of BFC1103. Purified GST tagged Bcl-2 loop domain was incubated with 50 μM BFC1103 at the indicated times to determine if BFC1103 interaction with loop domain had an effect on the proteolysis pattern upon co-incubation with trypsin.

Figure 23A:
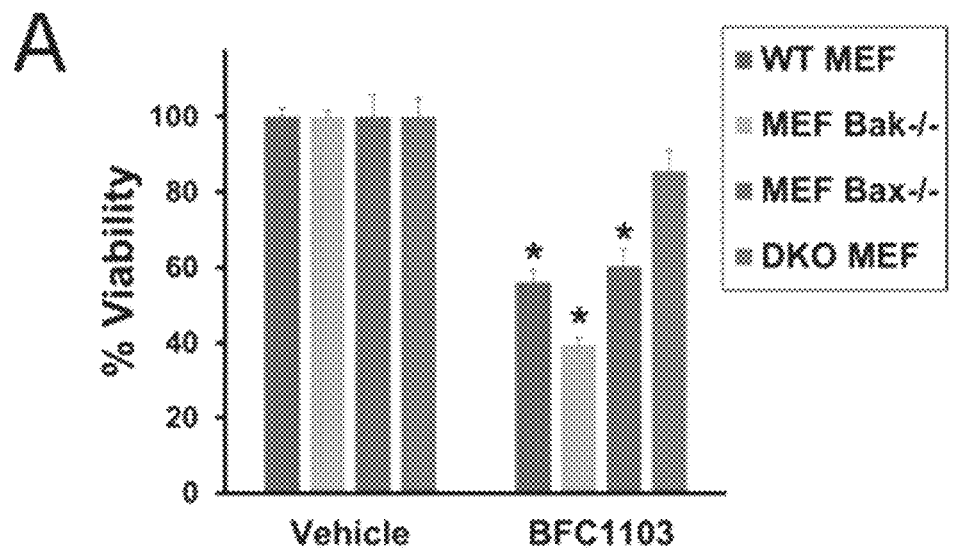

FIG. 23A shows that BFC1103 requires Bax/Bak for apoptosis induction. WT MEF, Bax$^{-/-}$ MEF, Bak$^{-/-}$ MEF and Bax$^{-/-}$ Bak$^{-/-}$ MEF cells were treated with 1 μM BFC1103 for 24 h in 10% FBS medium and viability was assessed using cell titer glo assay.

Figure 23B:
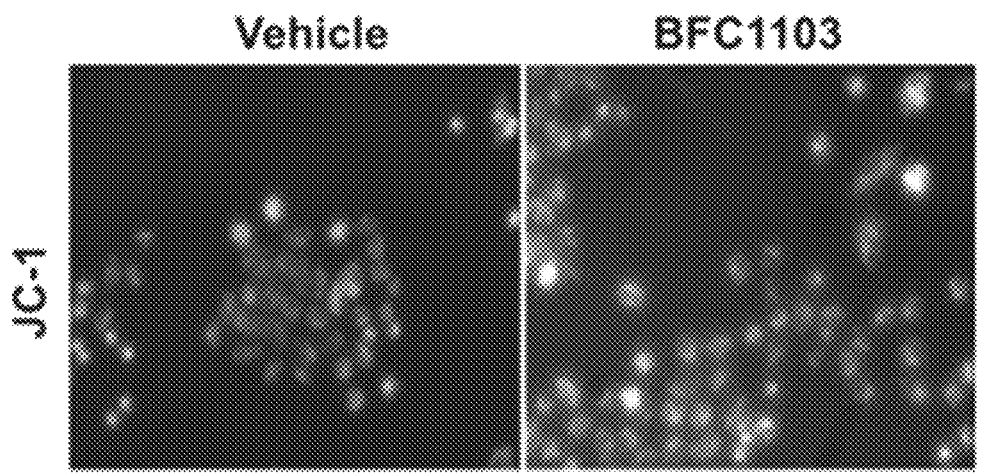

FIG. 23B shows that BFC1103 requires Bax/Bak for apoptosis induction. JC-1 stain was used to stain live H460 cells treated with 10 μM BFC1103 for 16 h in 10% FBS containing medium and images taken with FITC and rhodamine filters were overlaid. Cells stained orange have intact mitochondrial outer membrane and the ones turning green have compromised outer membrane indicating loss of membrane potential.

Figure 24A:
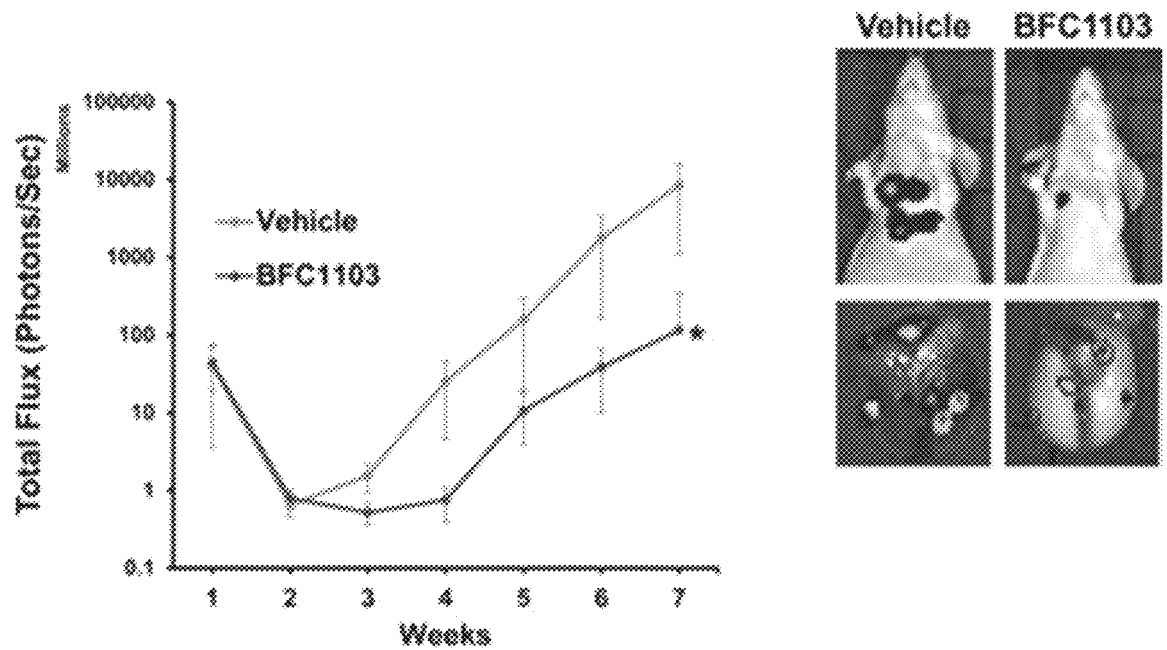

FIG. 24A shows that BFC1103 suppresses lung metastasis in vivo. About 200,000 LMD-231 cells stably expressing luciferase was injected into the tail vein of 6 week old nude mice. Lung metastasis was detectable in 2 weeks after injection of tumor cells. Mice were treated with 50 mg/kg of BFC1103 6 times a week by intraperitoneal injections. Bioluminescent imaging was performed once a week and quantified. *$P<0.05$.

Figure 24B:
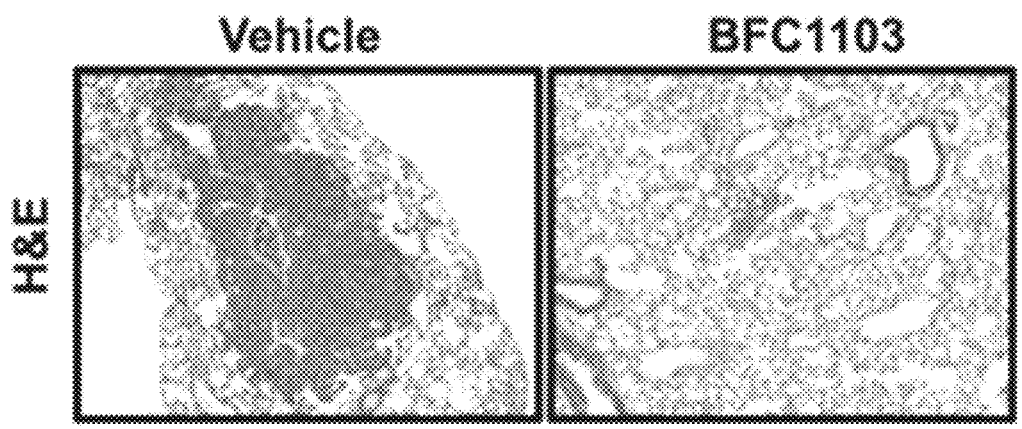

FIG. 24B H&E staining showed potent suppression of tumor cells in lung tissue of nude mice treated with BFC1103 compared to lung tissues from vehicle-treated mice.

Figure 24C:
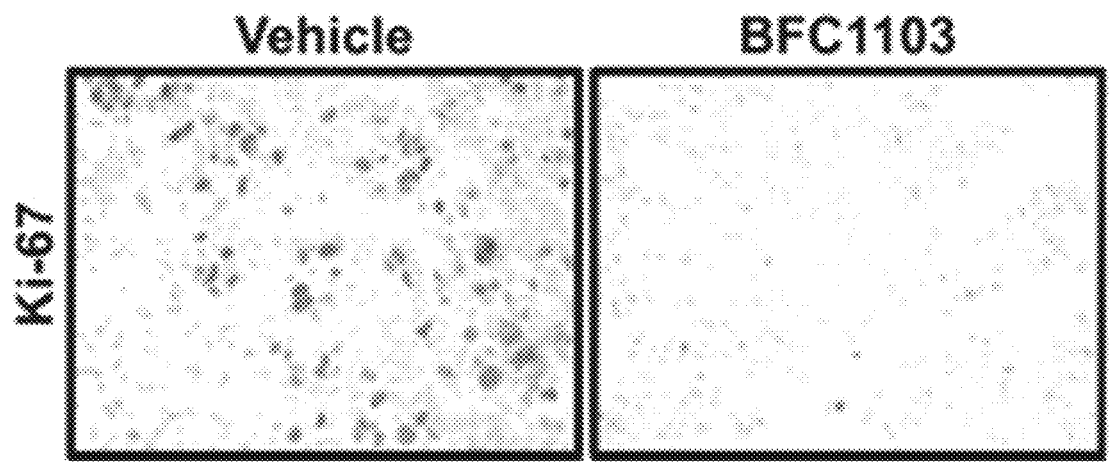

FIG. 24C shows that Ki-67 stain detects presence of tumor cells with high proliferation in lung tissue from vehicle-treated mice, compared to lung tissue from BFC1103-treated mice.

Figure 25A:
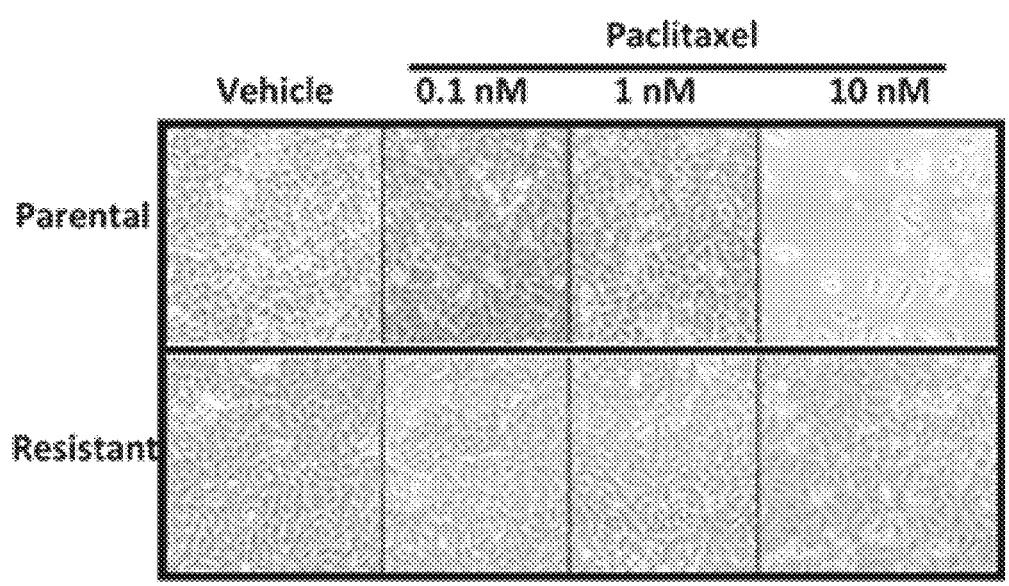

FIG. 25A shows H460 parental and paclitaxel resistant cells that were plated and treated with indicated paclitaxel concentration. Microscope images were captured after 48 hours.

Figure 25B:
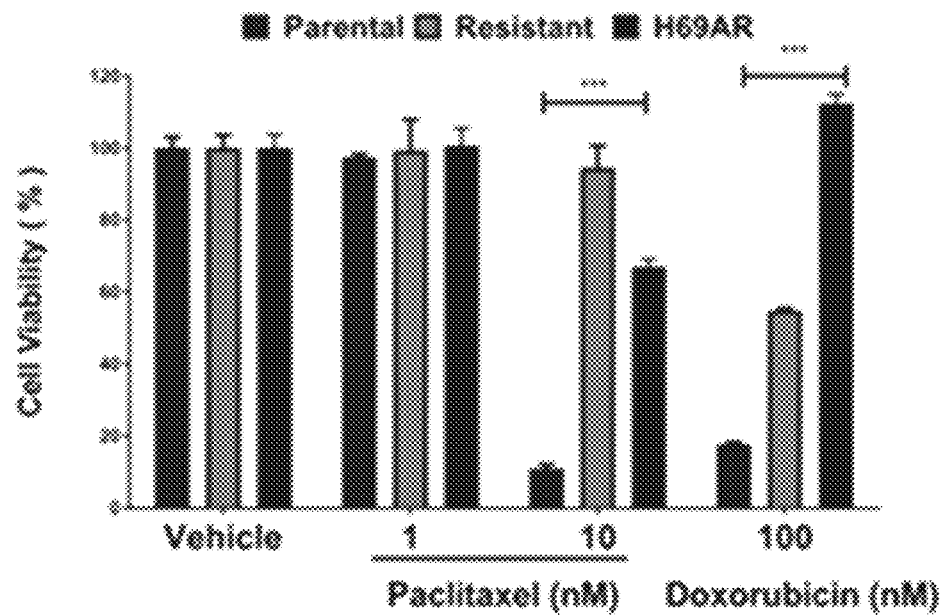

FIG. 25B shows results of viability assay of H460 parental and derived resistant cells and H69AR multidrug resistant cells treated for 72 hours. Percentage viability relative to vehicle treatment was calculated. Representative of three independent assays conducted in triplicate.

Figure 25C:
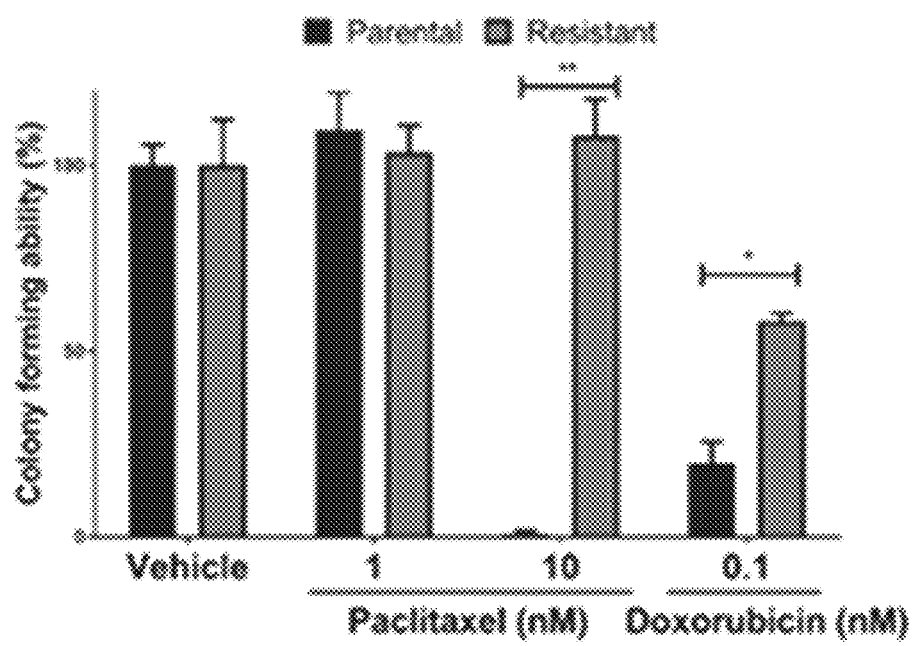

FIG. 25C shows results of clonogenic survival assays in H460 parental and resistant cells treated continuously for 14 days with vehicle, or indicated concentration of paclitaxel and doxorubicin (colony forming ability (%) relative to vehicle treatment; representative of three independent assays conducted in triplicate).

Figure 25D:
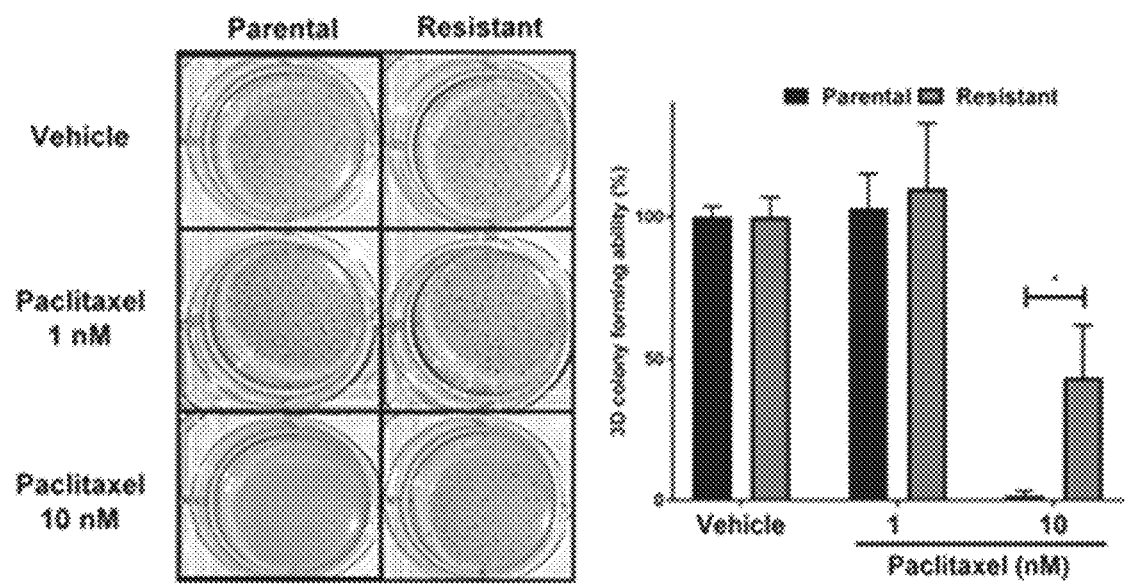

FIG. 25D shows results of 3D soft agar tumorigenicity assay in H460 parental and resistant cells treated continuously for 14 days with vehicle, or indicated concentration of paclitaxel (3D colony forming ability (%) relative to vehicle treatment).

Figure 25E:
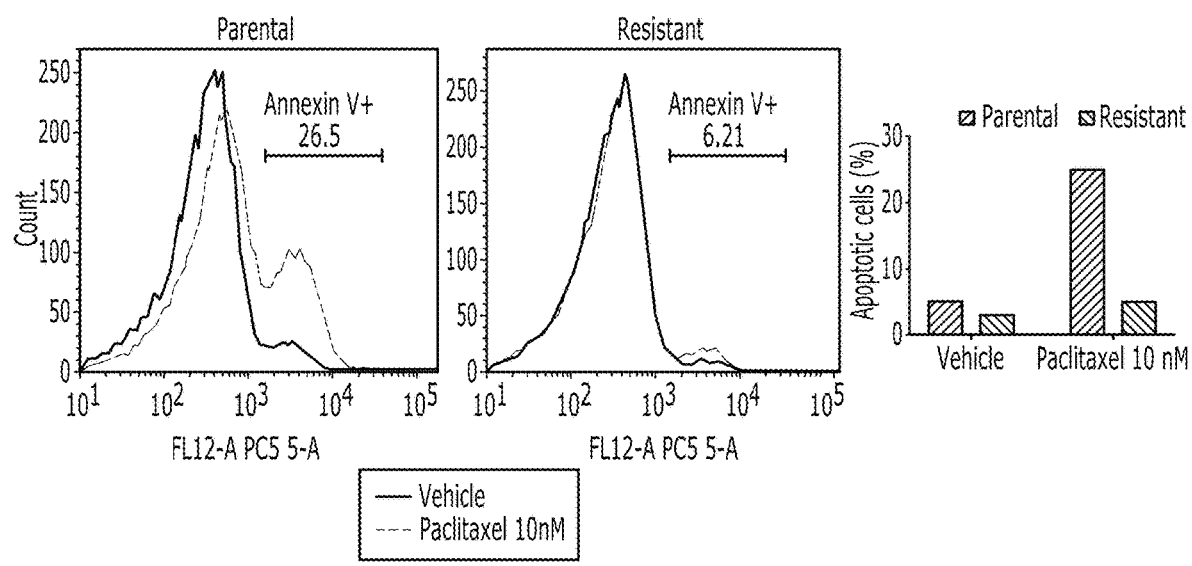

FIG. 25E is the results of Annexin-V apoptosis assay in H460 cells treated for 48 hours with vehicle or paclitaxel 10 nM, quantification right panel.

Figure 26A:
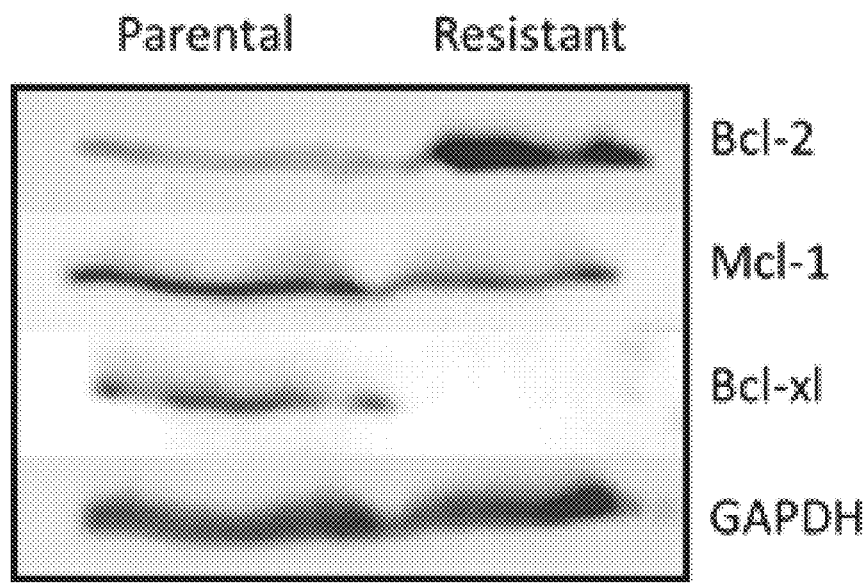

FIG. 26A is a Western blot analysis of H460 parental and derived paclitaxel resistant cells without any treatment and blotted with indicated antibodies.

Figure 26B:
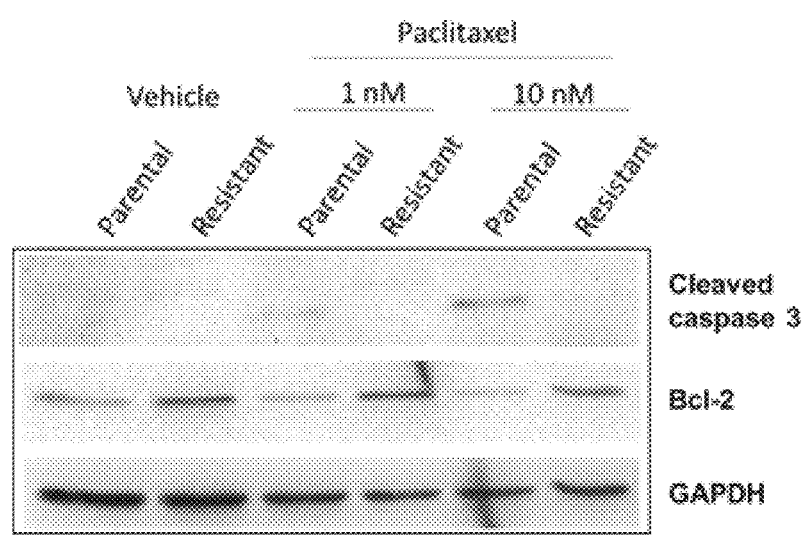

FIG. 26B is a Western blot analysis of H460 parental and resistant cells treated with paclitaxel for 48 hours and blotted with indicated antibodies.

Figure 26C:
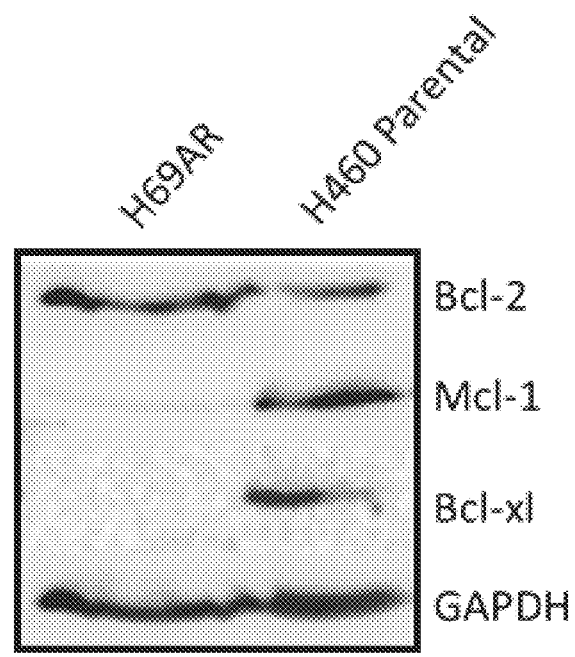

FIG. 26C is a Western blot analysis of multidrug resistant H69AR and H460 parental cells and blotted with indicated antibodies.

Figure 26D:
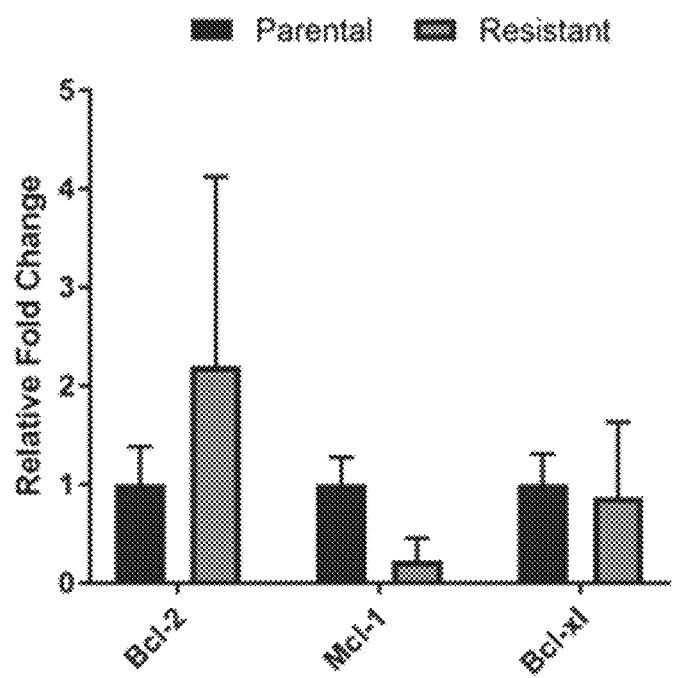

FIG. 26D is an mRNA expression analysis of Bcl-2, Mcl-1 and Bcl-xl levels in parental and resistant H460 cells using quantitative real-time PCR.

Figure 26E:
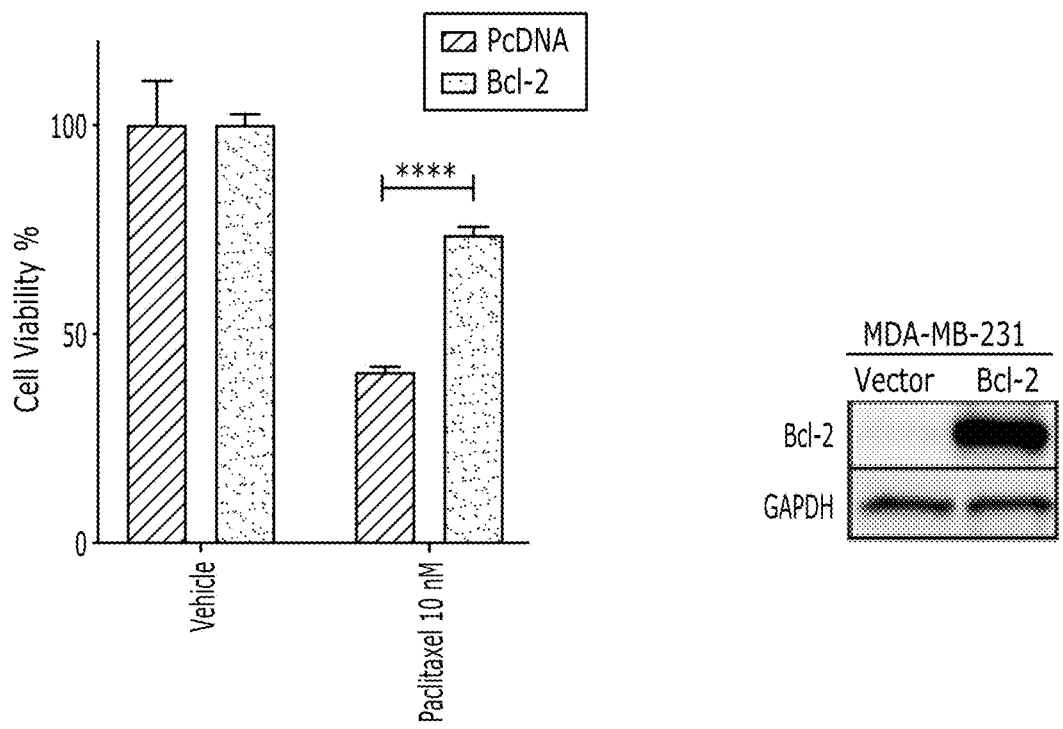

FIG. 26E is a viability assay in MDA-MB-231 cells expressing control pcDNA vector or Bcl-2, treated with vehicle or paclitaxel 10 nM; right panel: western blot analysis of transfected cells.

Figure 27A:
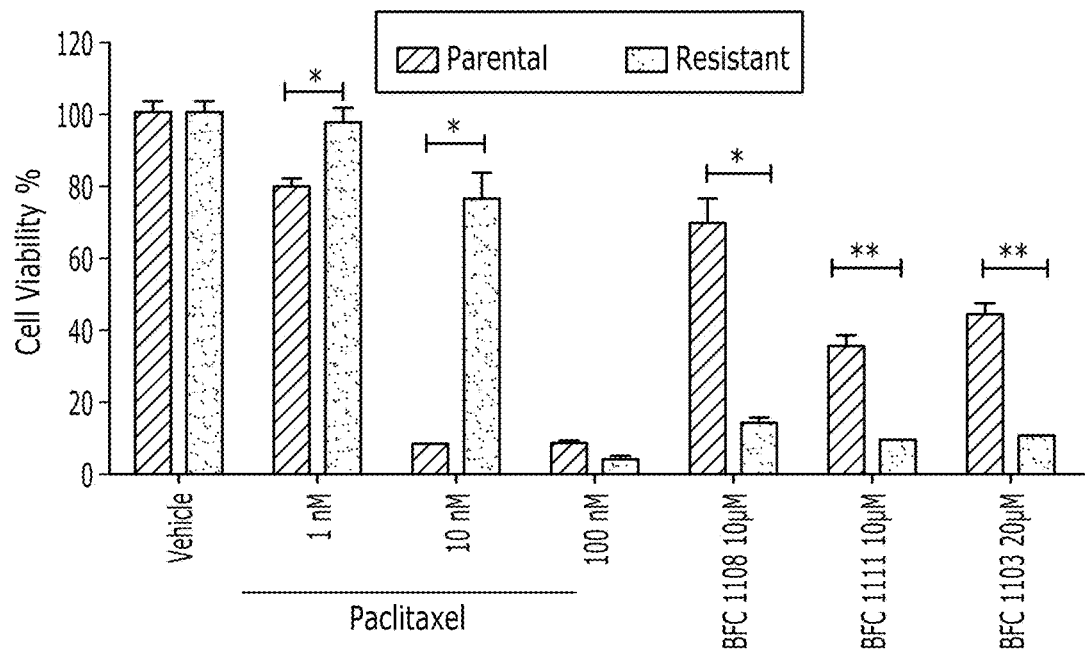

FIG. 27A is a viability assay of H460 parental and derived resistant cells treated for 72 hours with indicated compound. Percentage viability relative to vehicle treatment. Representative of three independent assays conducted in triplicate.

Figure 27B:
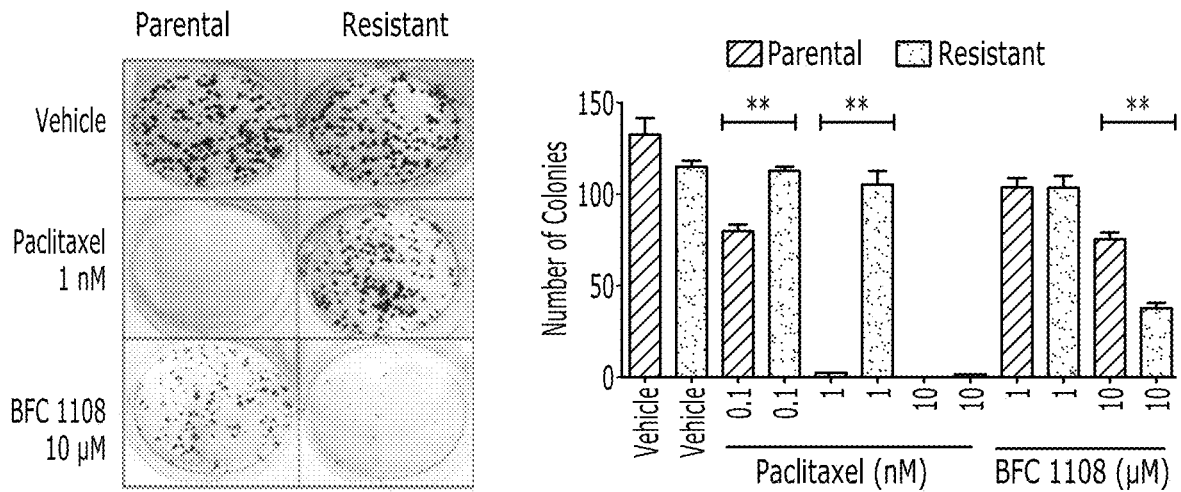

FIG. 27B demonstrates clonogenic survival assays in H460 parental and resistant cells treated continuously for 14 days with vehicle, or indicated concentration of paclitaxel and doxorubicin. Colony forming ability (%) relative to vehicle treatment. Representative of three independent conducted assays in triplicate.

Figure 27C:
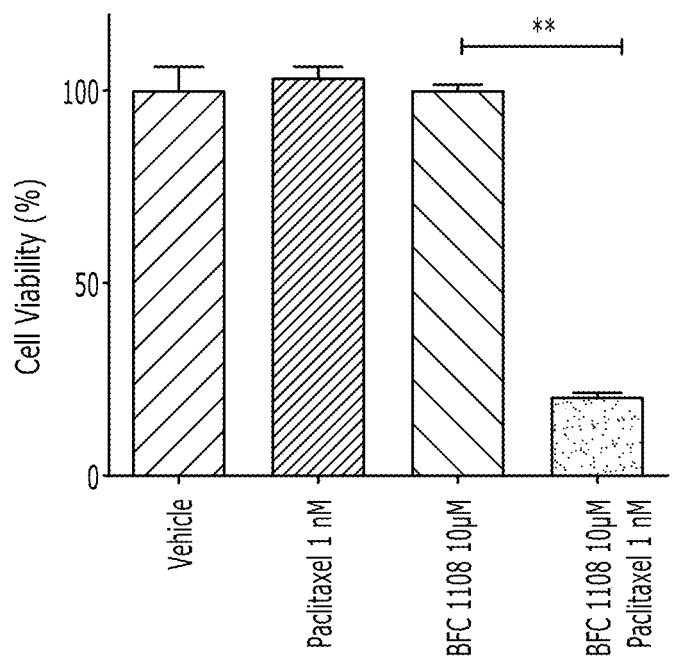

FIG. 27C demonstrates results of viability assay of H460 parent and resistant cells treated for 24 hours with indicated compounds. Representative of three independent assays conducted in triplicate.

Figure 27D:
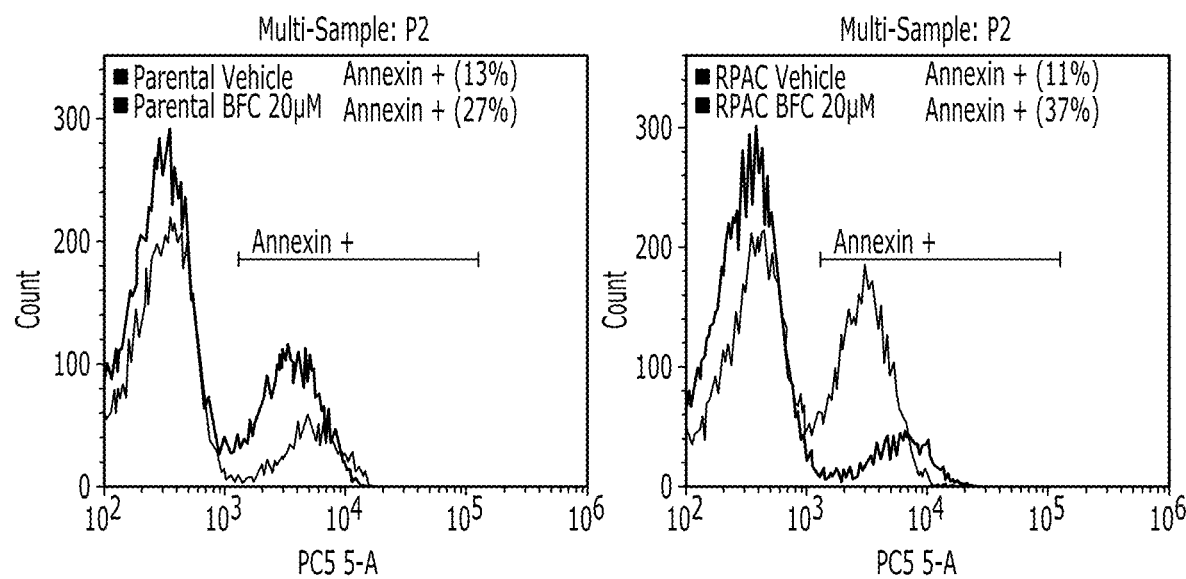

FIG. 27D shows results of Annexin-V apoptosis assay in H460 cells treated for 48 hours with vehicle or BFC 1108 20 μM, representative of three independent assays.

Figure 28A:
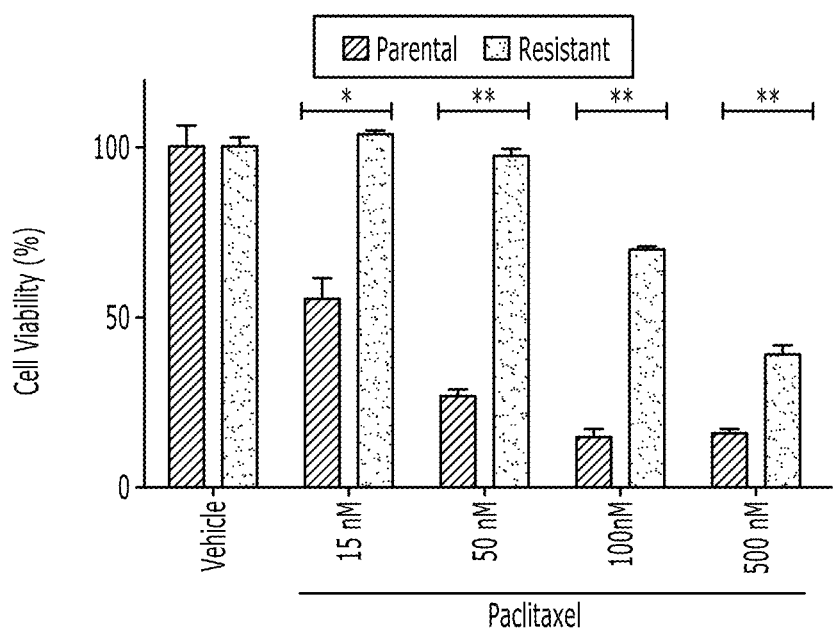

FIG. 28A shows results of viability assay of MDA-MB-468 parental and derived paclitaxel resistant cells treated for 72 hours. Percentage viability relative to vehicle treatment. Representative of three independent assays in triplicate.

Figure 28B:
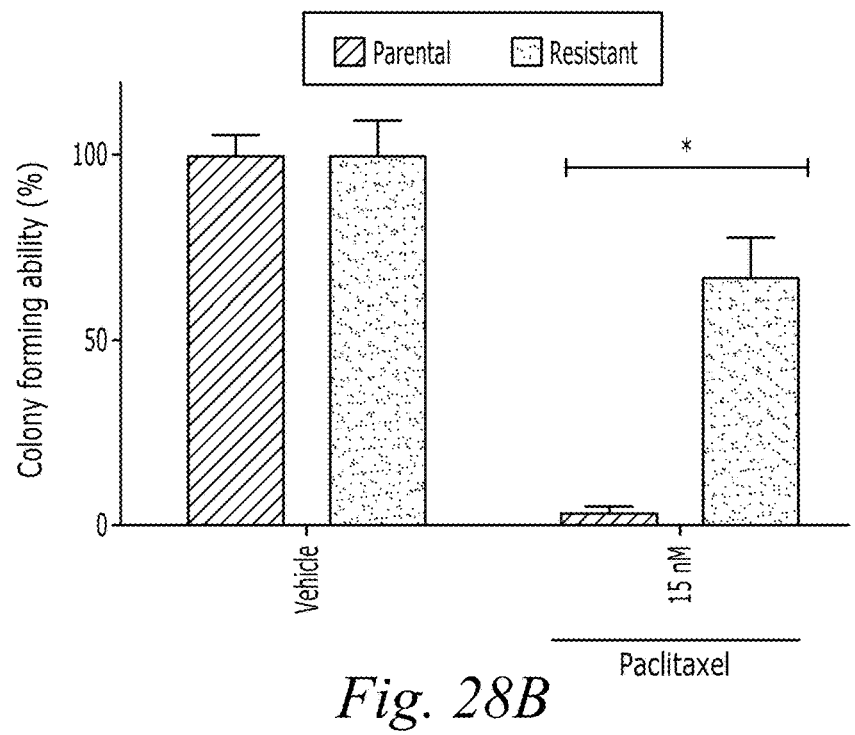

FIG. 28B depicts results of clonogenic survival assays in MDA-MB-468 parental and resistant cells treated continuously for 14 days with vehicle, or indicated concentration of paclitaxel. Colony forming ability (%) relative to vehicle treatment. Representative of three independent assays in triplicate.

Figure 28C:
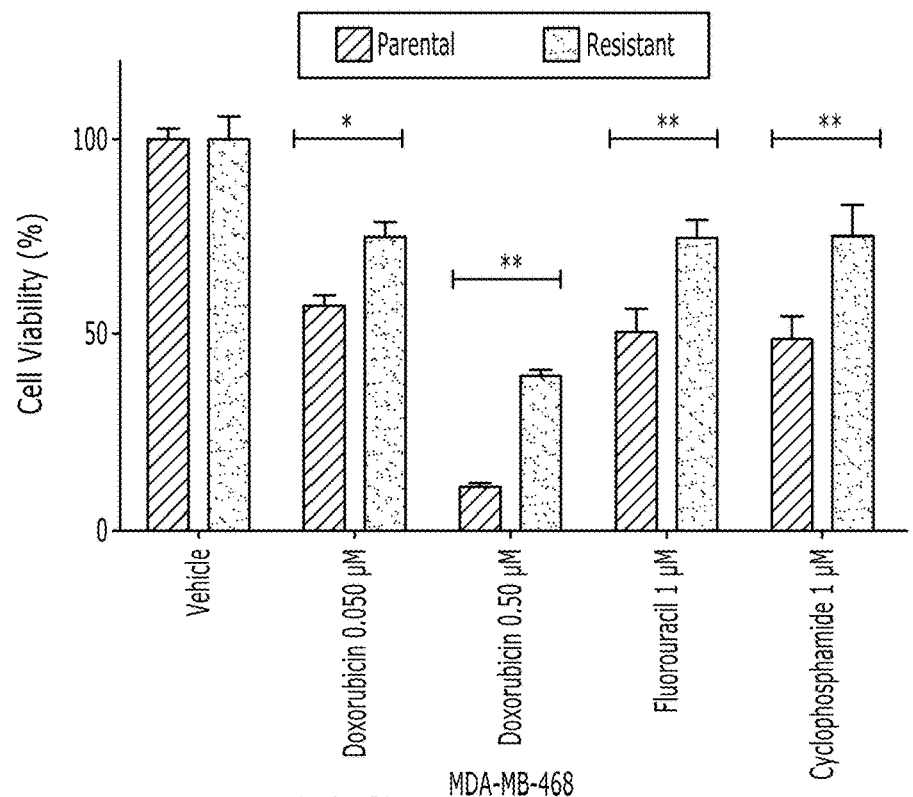

FIG. 28C shows results of viability assay of MDA-MB-468 parental and derived paclitaxel resistant cells treated for 72 hours with indicated compound. Percentage viability relative to vehicle treatment.

Figure 28D:
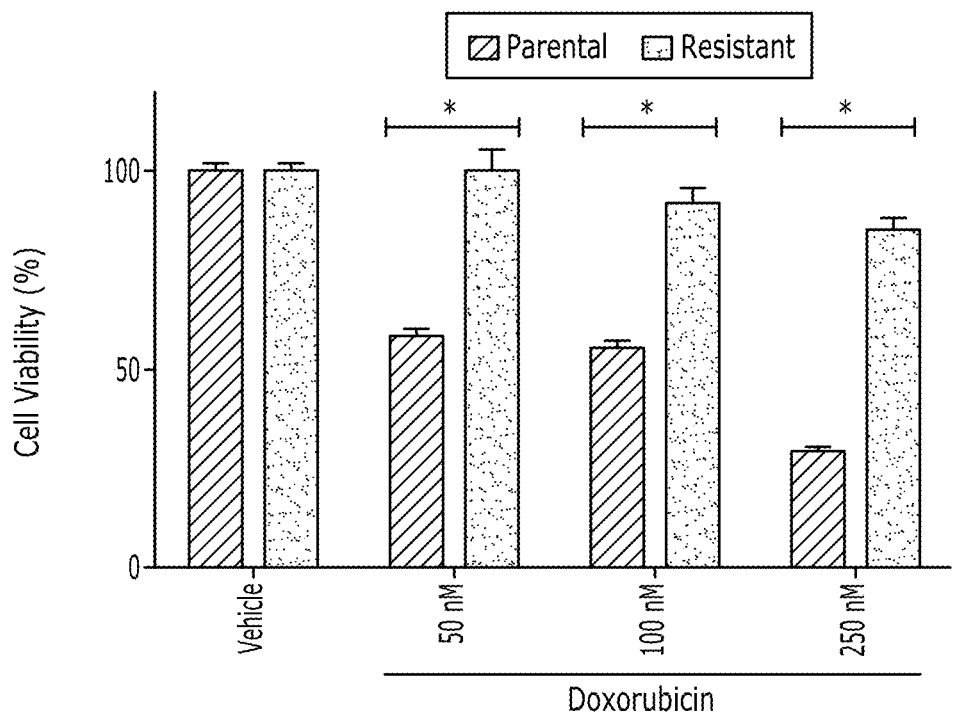

FIG. 28D shows results of viability assay of MDA-MB-468 parental and derived doxorubicin resistant cells treated for 72 hours. Percentage viability relative to vehicle treatment. Representative of three independent assays conducted in triplicate.

Figure 29A:
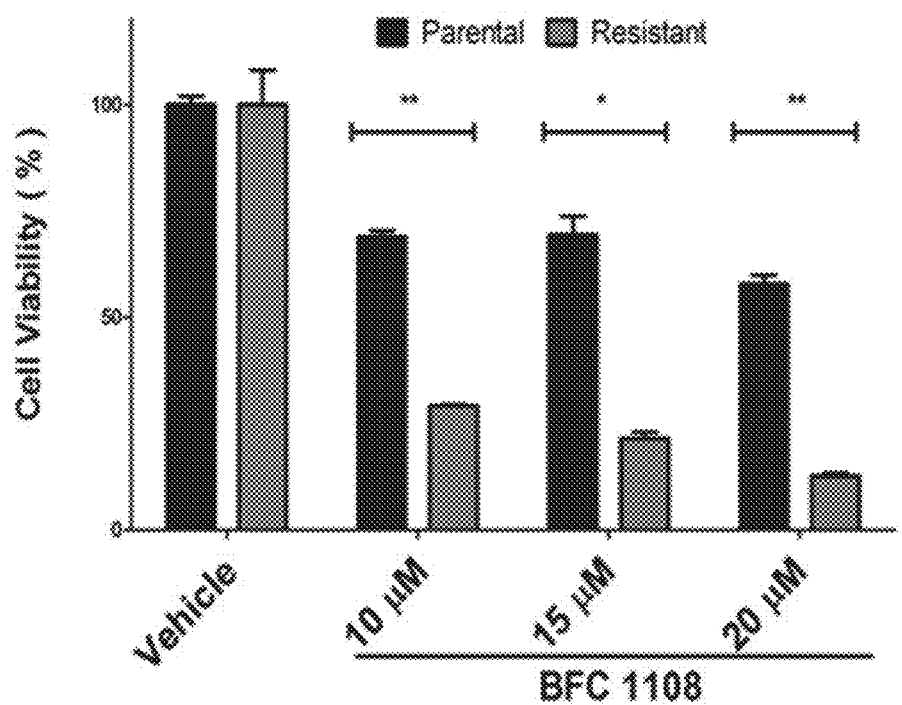

FIG. 29A shows results of viability assay of MDA-MB-468 parental and derived paclitaxel resistant cells treated for 72 hours. Percentage viability relative to vehicle treatment. Representative of three independent assays conducted in triplicate.

Figure 29B:
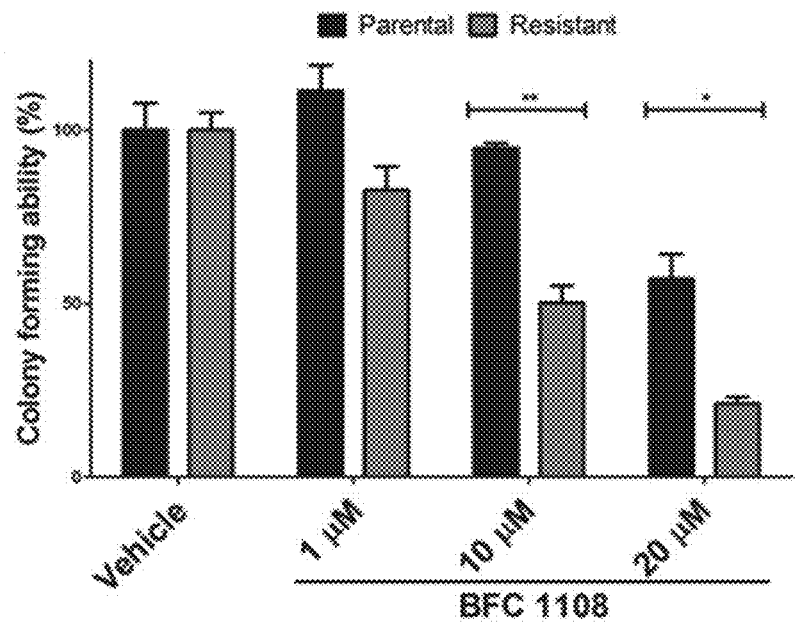

FIG. 29B is the results of clonogenic survival assays in MDA-MB-468 parental and resistant cells treated continuously for 14 days with vehicle, or indicated concentration of paclitaxel. Colony forming ability (%) relative to vehicle treatment. Representative of three independent assays conducted in triplicate.

Figure 29C:
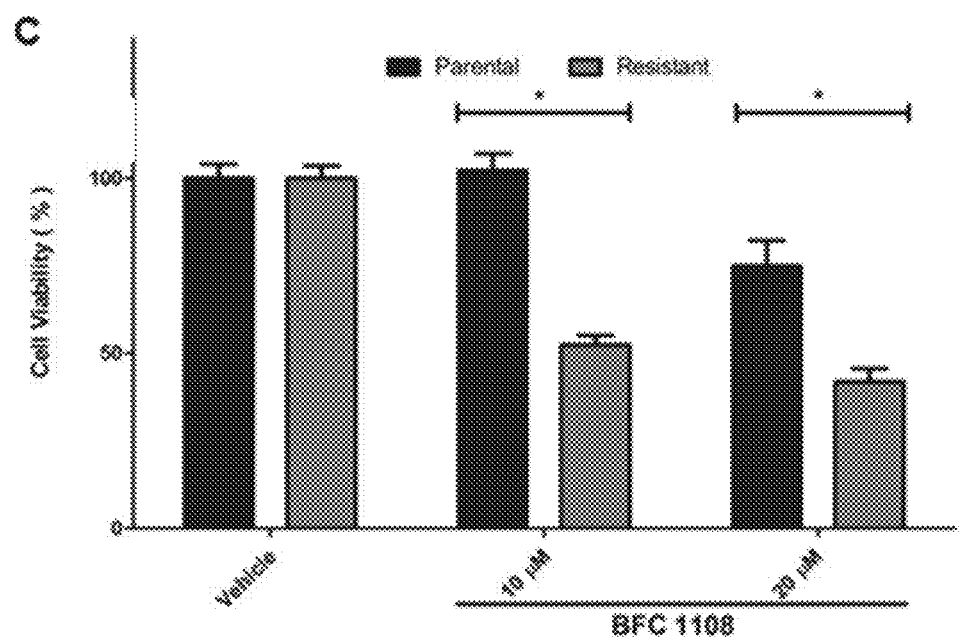

FIG. 29C shows results of viability assay of MDA-MB-468 parental and derived doxorubicin resistant cells treated for 72 hours. Percentage viability relative to vehicle treatment. Representative of three independent assays in triplicate.

Figure 30A:
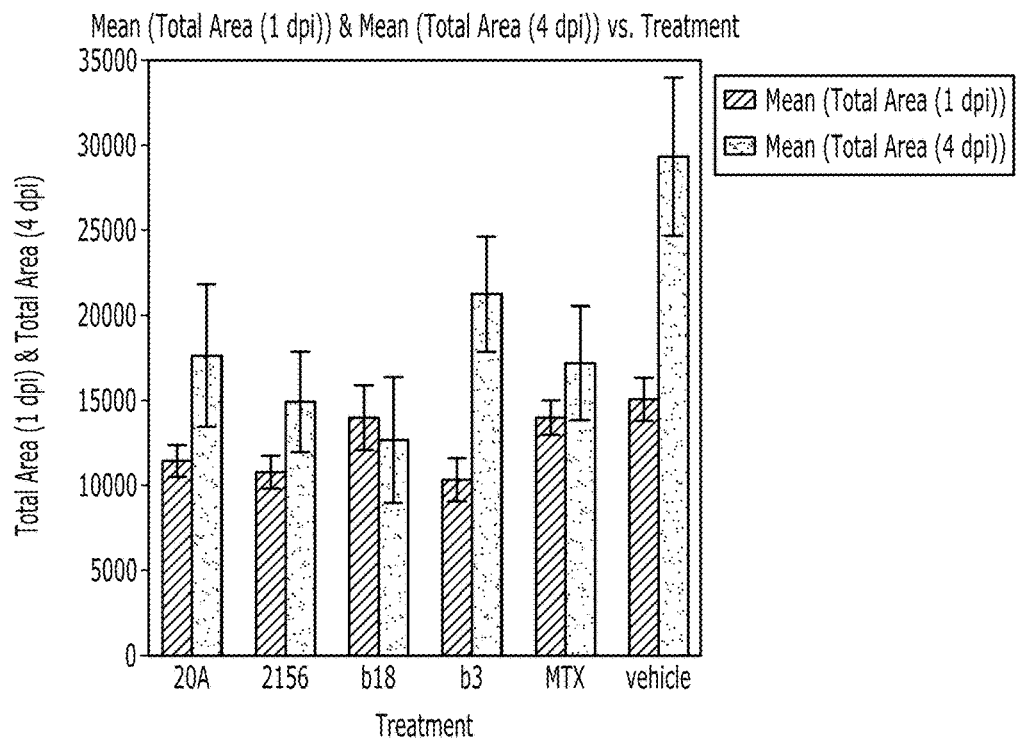

FIG. 30A shows growth of paclitaxel resistant h460 cells in zebrafish from 1 day post injection to 4 days post injection. Total area signifies total h460 cell area in zebrafish.

Figure 30B:
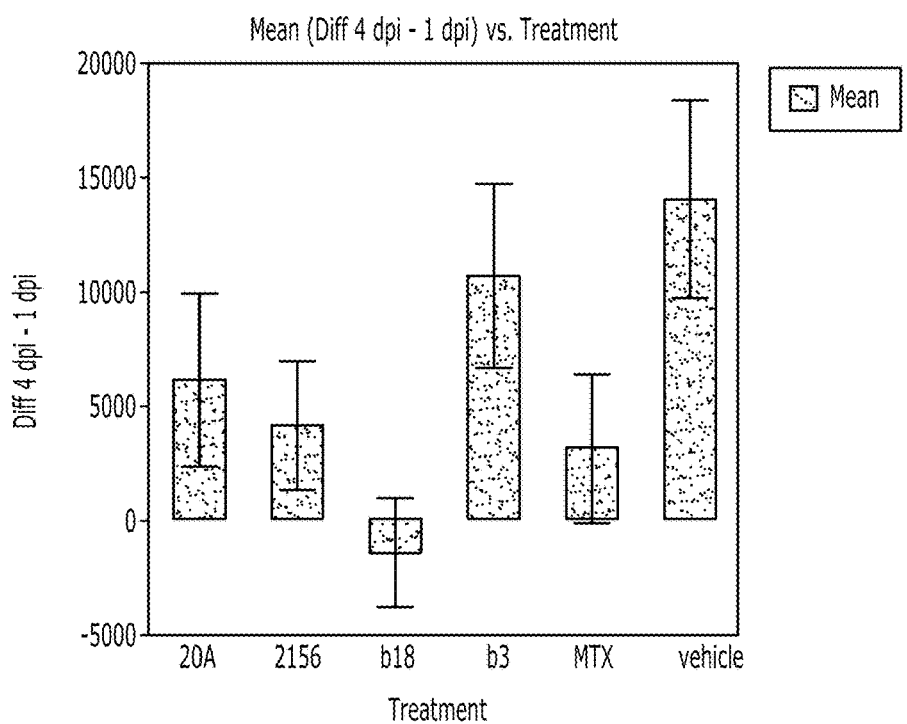

FIG. 30B shows difference in cell growth from day 1 to day 4 in zebrafish xenograft model.

Figure 31A:
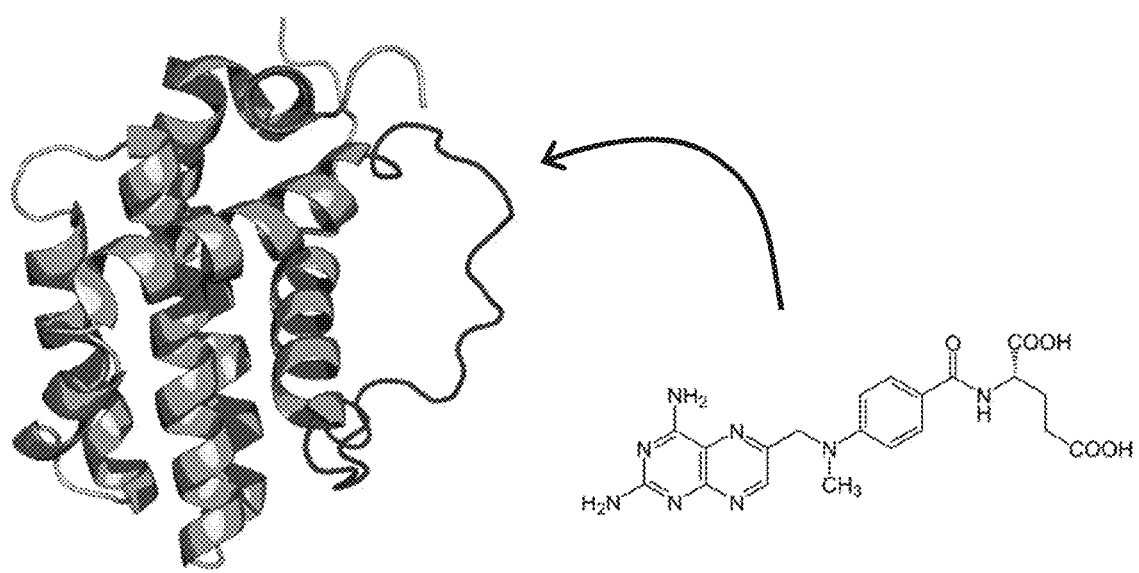

FIG. 31A depicts 3D structure of Bcl-2 with the loop domain (arrow) and the structure of methotrexate (MTX).

Figure 31B:
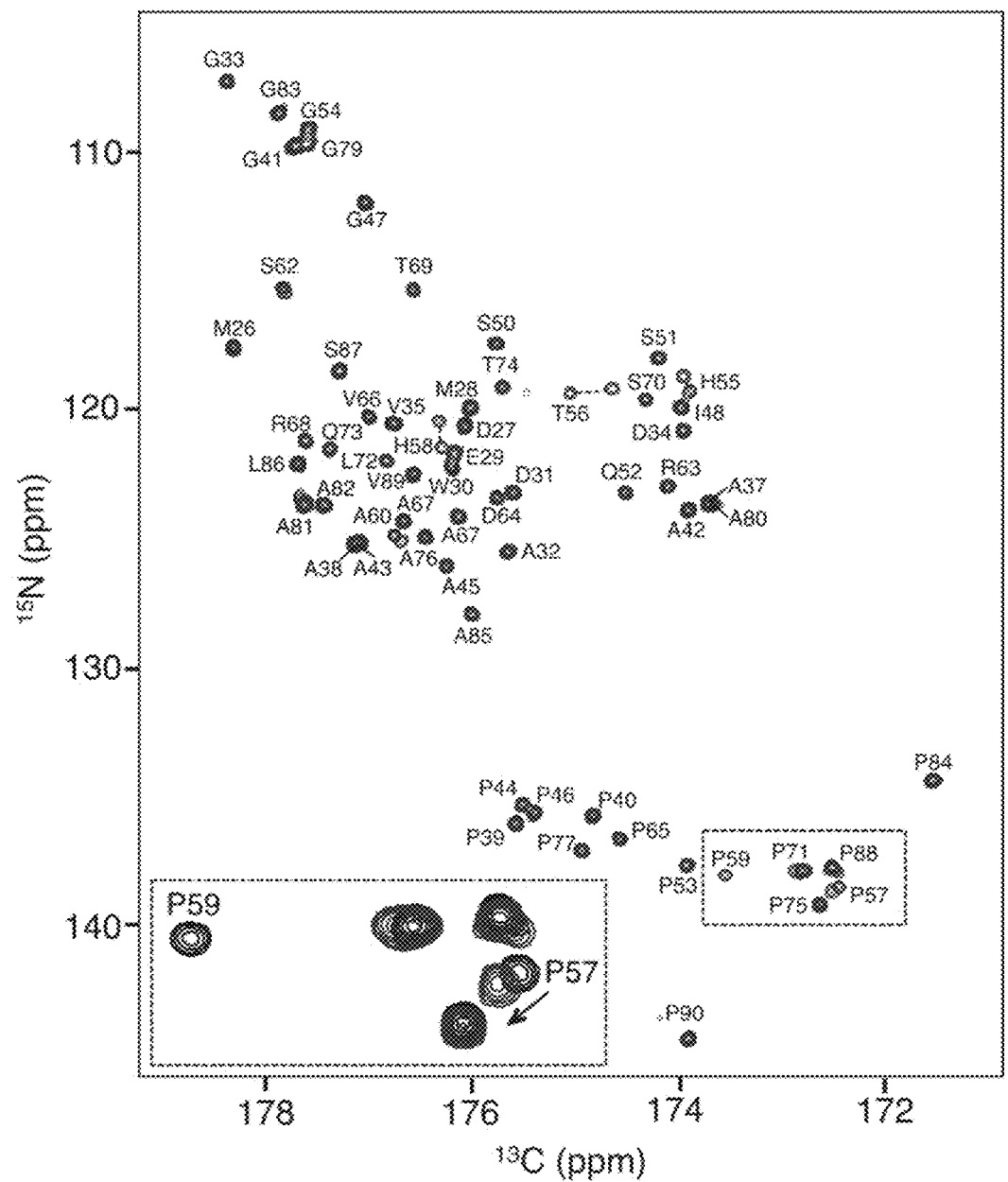

FIG. 31B is overlaid $^{15}N$-$^{13}C$ CON spectrum of 0.2 mM Bcl-2 loop domain, titrated with 5.4 mM MTX. Dashed box shows an expanded view of the proline spectrum region, highlighting the chemical shift perturbations of Pro57 and Pro59 upon MTX binding.

Figure 31C:
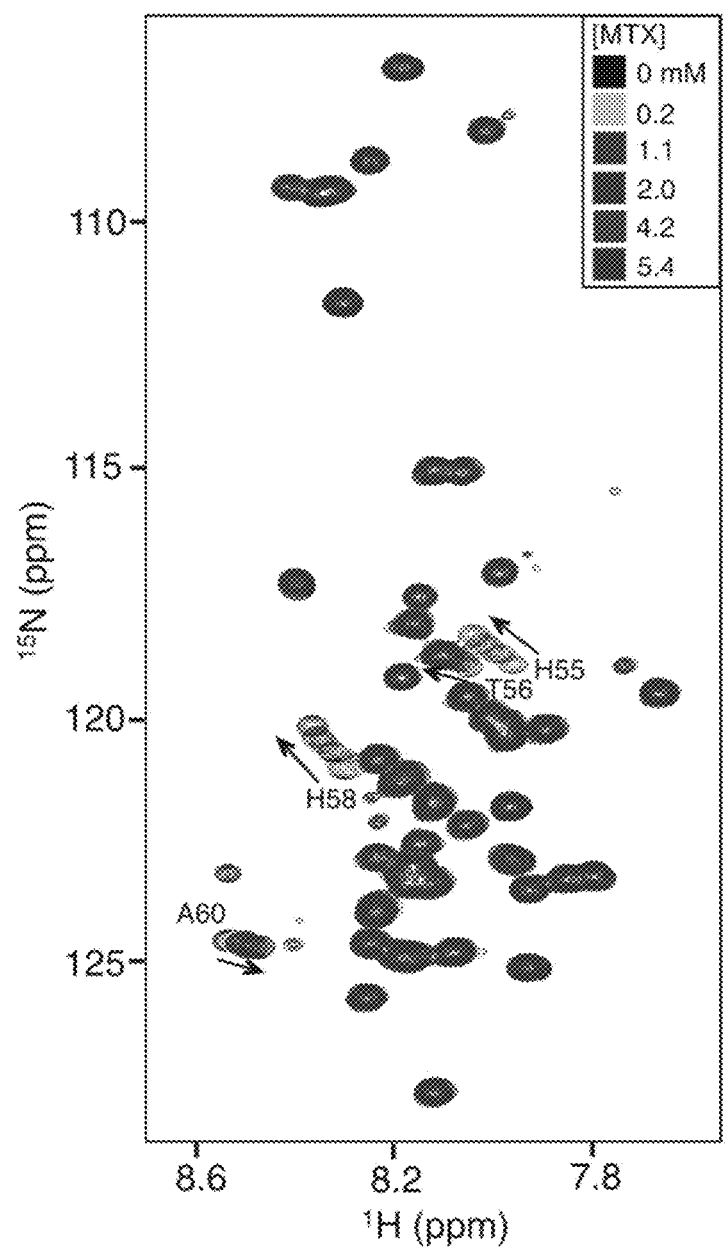

FIG. 31C are overlaid $^{1}H$-$^{15}N$ HSQC spectra of 0.2 mM Bcl-2 loop titrated with 0.2-5.4 mM MTX. Residues for which the amide resonance had a significant chemical shift perturbation are labeled.

Figure 31D:
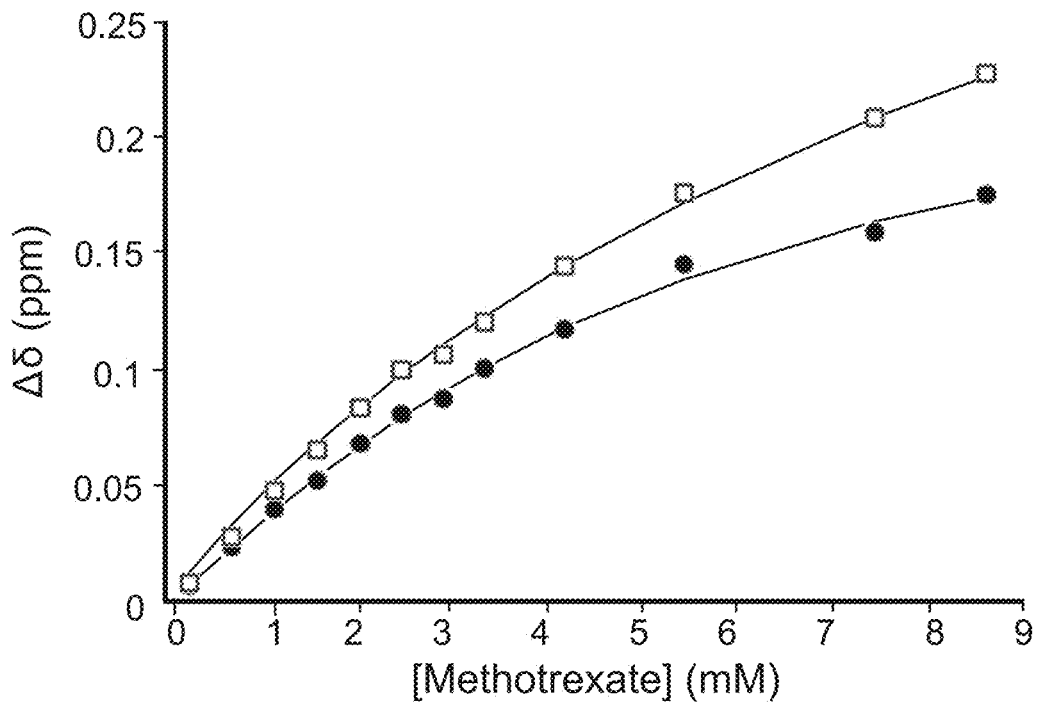

FIG. 31D illustrates the changes in chemical shift for His55 (black circles) and His58 (open circles) compared to MTX concentration and fit to a Hill model (solid lines). The calculated Hill coefficient was 1.2 for His55 and 1.0 for His58.

Figure 31E:
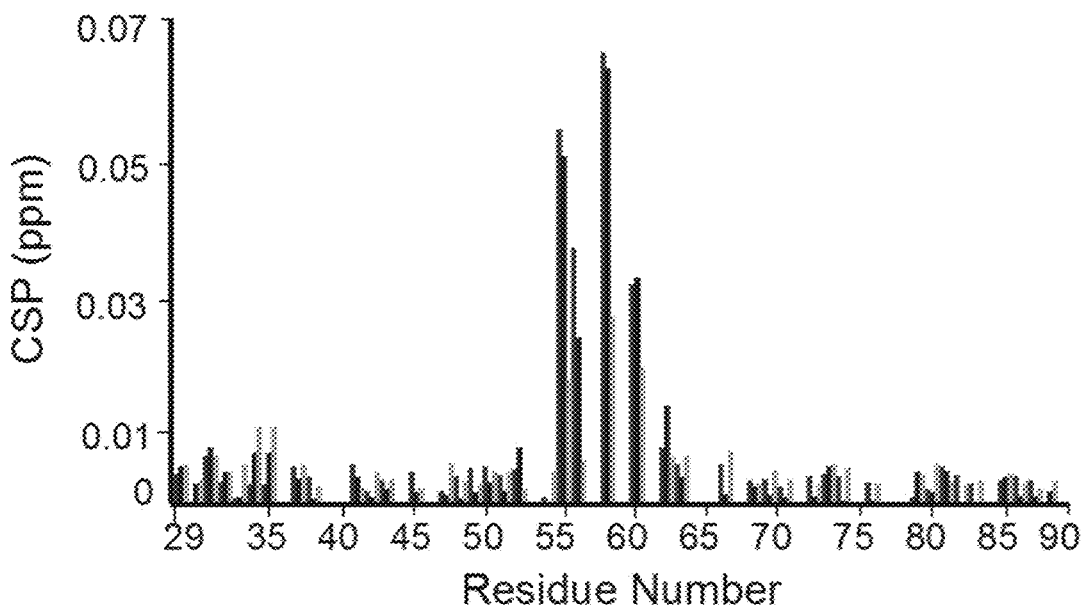

FIG. 31E is a plot (of the chemical shift perturbations measured for Bcl-2 loop domain backbone amides in the presence of 1.6 mM MTX (grey), 8.6 mM NuBCP-9 peptide (black), and 8.6 mM inactive mutant NuBCP-9 (light grey). Gaps correspond to proline residues.

Figure 31F:
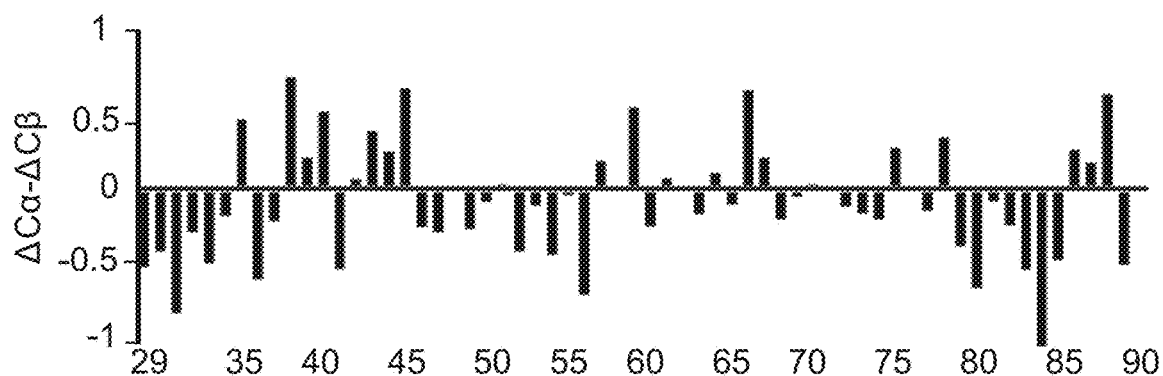

FIG. 31F shows secondary chemical shift differences that are plotted against residue number. $\Delta C\alpha$ and $\Delta C\beta$ values were calculated by subtracting the random coil chemical shift from the experimentally determined chemical shift value (Tamiola, 2010, JACS, Sequence-specific random coil chemical shifts of intrinsically disordered proteins). $\Delta C\alpha$–$\Delta C\beta$ values>±1.0 ppm were considered significant.

Figure 31G:
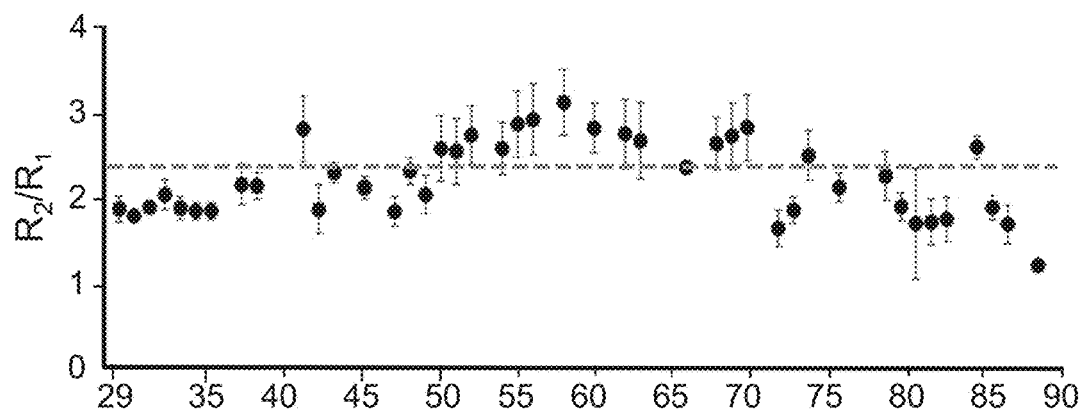

FIG. 31G is a plot of $R_2/R_1$ values measured at 10° C. per residue. A dotted line is placed at the average value (2.2) to aid in visualization.

Figure 31H:
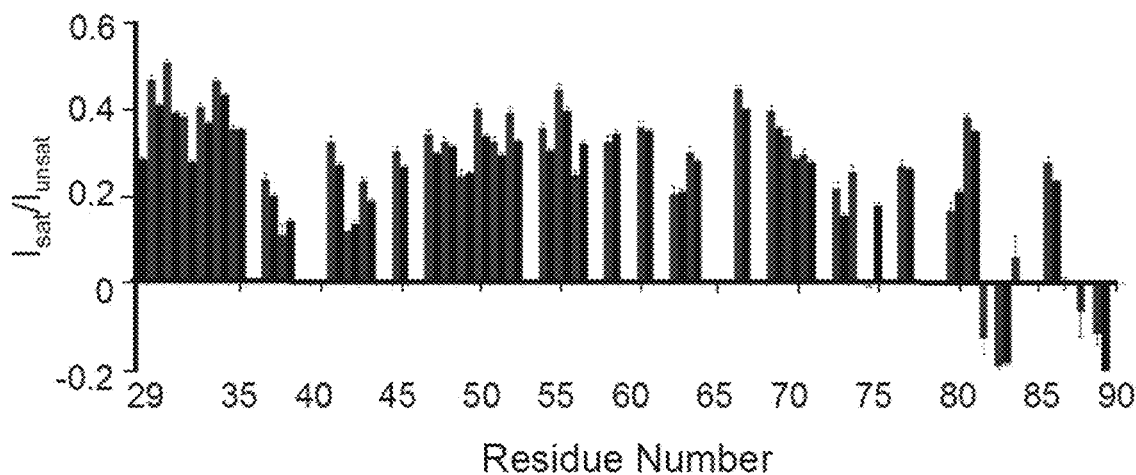

FIG. 31H shows heteronuclear NOE values measured at 10° C. plotted against residue number for unbound Bcl-2 loop domain (black) and Bcl-2 loop domain in the presence of 5.4 mM MTX (grey).

DETAILED DESCRIPTION OF THE INVENTION

There is a great deal of interest in developing small molecule inhibitors of Bcl-2 for cancer therapy. This is due to the role of Bcl-2 family of proteins in regulating cellular survival and resistance to cancer therapies.

Figure 1:
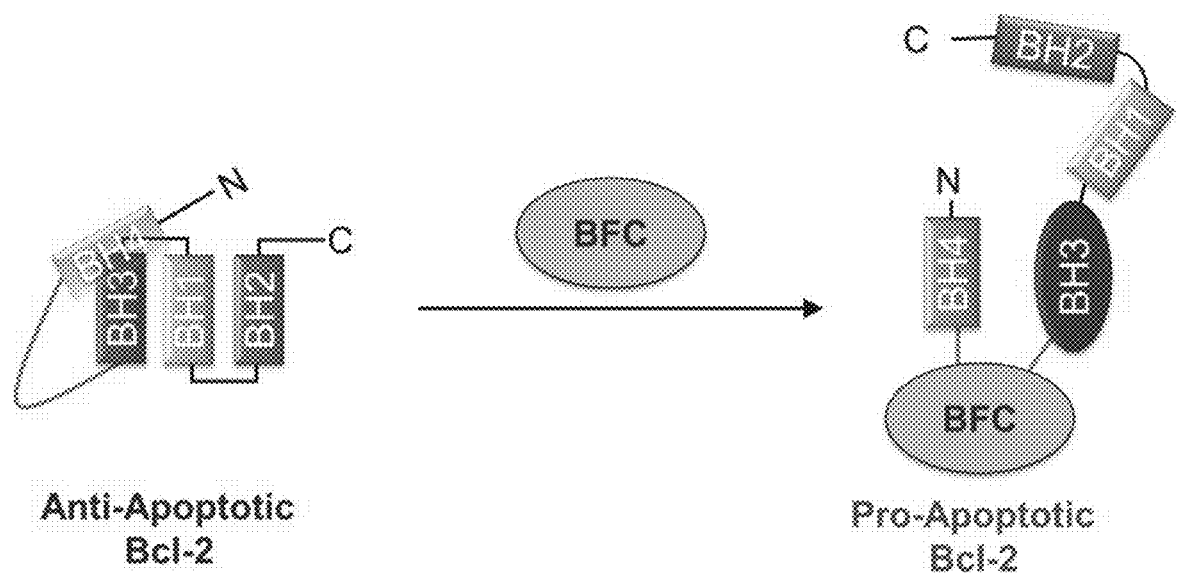
FIG. 1 depicts how small molecule Bcl-2 functional converters (BFC) interact with Bcl-2 and change the conformation of Bcl-2 exposing its BH3 death domain.

The Bcl-2 functional conversion from its anti-apoptotic form to a pro-apoptotic form is induced by binding of orphan nuclear receptor, Nur77. Nur77 or Nur77-derived peptide NuBCP-9 bind to the unstructured loop domain of Bcl-2 and expose its BH3 domain, which converts Bcl-2 from an anti-apoptotic protein into a pro-apoptotic (pro-death) protein. Based on this functional conversion mechanism, the inventors discovered that small molecules that mimic the functional activity of NuBCP-9 peptide can accomplish such conversion of Bcl-2 (FIG. 1). Such small molecule Bcl-2 functional converters (BFCs) are advantageous as they would be easy to administer and achieve therapeutic concentrations in vivo.

The three specific goals of this research are to 1) identify small molecules that can preferentially induce apoptosis in Bcl-2-overexpressing triple negative breast cancer cells, 2) test if these small molecules interact with Bcl-2, expose its BH3 domain and induce Bcl-2-dependent cell death, and 3) establish the efficacy of the identified small molecules in human primary and metastatic triple negative breast cancer xenograft mouse models.

To address these goals, the inventors designed a screening assay using human triple negative breast cancer cells (MDA-MB-231) with Bcl-2 overexpression along with their vector controls and screened small molecule libraries of either existing drugs or novel small molecules for Bcl-2-dependent effects on cell survival. Small molecules identified by this approach were revalidated based on their ability to preferentially induce cell death in Bcl-2 overexpressing MDA-MB-231 cells as compared to their vector control cells. Thus, the work invention provides methods for identification and testing of small molecule BFCs that have the potential in treating stubborn cancers that are dependent on Bcl-2 expression, methods for inducing apoptosis in cancer cells by BFCs, and methods of treatment of Bcl-2-overexpressing cancers or cancers that depend on Bcl-2 with small molecule BFCs.

1. Small Molecule Functional Converters of Bcl-2

In one aspect, provided herein are methods for inhibiting growth and/or inducing apoptosis of a Bcl-2-expressing cells, comprising treating or contacting a Bcl-2-expressing cells with an agent that exposes the BH3 domain of Bcl-2 thereby converting Bcl-2 into a pro-apoptotic protein and activating the intrinsic apoptosis pathway. In some embodiments, the cell is ex vivo. In other embodiments, the cell is in vivo, e.g., a human tumor cell.

In another aspect, provided herein methods of treating Bcl-2-expressing cancers in a subject comprising administering to a subject with a Bcl-2-expressing cancer a therapeutically effective amount of an agent that exposes the BH3 domain of Bcl-2 thereby converting Bcl-2 into a pro-apoptotic protein. In some embodiments, the cancer is selected from blood cancer, breast cancer, and lung cancer. In certain embodiments, the cancer is non-small cell lung cancer or triple-negative breast cancer.

In some embodiments, the agent of the methods of the invention is a small molecule, i.e., an organic compound with the molecular weight of about 900 daltons or less. In certain embodiments, the agent of the methods of the invention is a small molecule mimic of NuBCP-9 peptide. As used herein, "a small molecule mimic of NuBCP-9 peptide" is a small molecule that mimics binding of NuBCP-9 peptide to the loop domain of Bcl-2. In some embodiments, the small molecule mimic of NuBCP-9 peptide is non-peptidic.

There is a great deal of interest in developing small molecule inhibitors of Bcl-2 for cancer therapy. This is due to the role of Bcl-2 family of proteins in regulating cellular survival and resistance to cancer therapies. However, a new mechanism by which Bcl-2 is converted into a pro-death molecule was demonstrated using a 9 amino acid peptide, NuBCP-9 derived from the orphan nuclear receptor Nur77. This functional conversion mechanism has a great deal of advantages as compared to inhibition, for cancer therapy.

The inventors hypothesized sought to discover and develop small molecule mimetics of Nur77 or NuBCP-9 to selectively target cancers expressing Bcl-2. For this a functional screen was designed using triple negative breast cancer cells MDA-MB-231 with high and low expression of Bcl-2. The inventors found a number of small molecules that can selectively induce death in cells with high expression of Bcl-2. These small molecules could be further developed as successful therapies for treating cancers expressing Bcl-2 protein.

In cancer cells, the Bcl-2 family of proteins promotes cellular survival often by upregulation of its anti-death members (References 1-4). This phenomenon has made the Bcl-2 family of proteins an attractive target for developing targeted therapies in particular cancer types (Reference 5). As cancer cells depend on one or more of these Bcl-2 proteins for survival and development of resistance, targeting them makes an attractive proposal for drug development (Reference 5). The anti-apoptotic Bcl-2 proteins Bcl-2, Bcl-xL, Mcl-1, Bcl-w and Bfl-1 inhibit apoptosis by neutralizing the BH3 domains of pro-apoptotic proteins. This interaction happens between the BH3 domain of pro-apoptotic proteins and a groove formed by helices u2 (BH3) and parts of α3, α4, α5 (BH1) and α8 (BH2) of the anti-apoptotic proteins (Reference 5). This pocket is usually targeted by inhibitors to neutralize the protection mechanisms of the anti-apoptotic proteins (Reference 6). To inhibit the over-expression of anti-apoptotic proteins, numerous efforts to develop anti-sense molecules, peptide based inhibitors and small molecule inhibitors are at various stages of development (Reference 7-10).

There have been multiple approaches employed in the discovery of inhibitors of anti-apoptotic proteins (Reference 11). Screening assays were designed using small molecule screens and structure-based methodologies to identify an array of small molecules and peptides with various degrees of activity and specificity (Reference 12-15). While some peptides were based on the BH3 domains of pro-apoptotic proteins some were derived from completely different mechanism like NuBCP-9 from Nur77 protein (Reference 16-18). Whether peptide or small molecule, the goal of these inhibitors is to displace pro-apoptotic family members and restore the apoptotic pathway. Small molecules have an edge over peptides, in that, they are more stable and can be made cell-permeable making them easy to test their activity in animal models. Various techniques have been used to design high throughput screening assays for the discovery of small molecules that can disrupt the interaction between the hydrophobic groove of the anti-apoptotic proteins with the a helix of the pro-apoptotic proteins (Reference 19). Fluorescence polarization assays detected the very first small molecule disruptor of Bcl-xL/Bak BH3 and Bcl-xL/BAD BH3 by competitive binding, revealing the "BH3I" class of small molecules that could induce apoptosis (References 16, 20). Of note are the ABT-737 series of compounds that were initially discovered by high throughput biochemical screening; ABT-263 and ABT-199 are advancing in clinical trials showing efficacy in Bcl-2 dependent cancers (References 21-25). However, when a specific chemical inhibitor is used to block the activity of one protein, the cancer cells over-express other anti-apoptotic proteins as a resistance mechanism to avoid cell death (References 26-28). Pan chemical inhibitors that block multiple anti-apoptotic Bcl-2 members will likely have systemic toxicity.

A disadvantage to using inhibitors of the Bcl-2 family is that resistance is highly likely, and therefore, novel mechanisms of targeting the Bcl-2 proteins are desirable. Nur77 an orphan nuclear receptor interacts with Bcl-2 in mitochondria and changes its conformation exposing its BH3 domain (Reference 17). This was further demonstrated using a peptide derived from Nur77; NuBCP-9, a 9 amino acid peptide which binds to the loop domain of the Bcl-2 protein and changes its conformation to expose its BH3 domain. This exposure of the BH3 domain makes the Bcl-2 protein a pro-apoptotic protein (Reference 18). What sets apart this functional conversion of Bcl-2 from its inhibitors is that this changed conformation of Bcl-2 not just disrupts the interaction of anti-apoptotic Bcl-2 with its pro-apoptotic binding partners but Bcl-2 now acts like apro-apoptotic protein wherein it can neutralize other anti-apoptotic proteins and activate multi-domain pro-apoptotic proteins. NuBCP-9 was also shown to be targeting Bcl-B in addition to Bcl-2 (Reference 29). Therefore this functional conversion mechanism could be a better alternative to inhibitors which are susceptible to resistance due to over-expression of anti-apoptotic proteins not inhibited in the treatment regimen. The use of NuBCP-9 peptide is limited with the use of cell penetrating peptide (CPP) due to stability issues in vivo and to achieve a desirable pharmacokinetic profile (Reference 30). There is however some promising developments in the delivery of NuBCP-9 peptide using polymeric nanoparticles (Reference 31, 32). The inventors hypothesized that small molecule functional converters of Bcl-2 could be developed to use as therapeutics in Bcl-2 dependent and Bcl-2 expressing cancers.

In some embodiments, provided herein are methods for identification of small molecule agents, or BFCs, that can selectively convert Bcl-2 protein from its anti-apoptotic form into its pro-apoptotic form. In certain embodiments, the method is a method of screening for an agent that converts Bcl-2 from an anti-apoptotic protein into a pro-apoptotic protein, comprising:

(a) contacting a first population of cells with an agent, wherein the first population of cells expresses or over-expresses Bcl-2;
(b) determining the cell viability of the first population of cells;
(c) contacting a second population cells with the agent, wherein the second population of cells has no expression of Bcl-2 or expression of Bcl-2 lower than first cell population; and
(d) determining the cell viability of the second population of cells;
(e) comparing the cell viability of the first and second populations of cells to determine whether the agent converts Bcl-2 from an anti-apoptotic protein into a pro-apoptotic protein.

In some embodiments, identification of the selective BFCs is accomplished by screening of libraries of compounds using the assays provided herein. An exemplary library is the LOPAC®, 1280 is a chemical library of 1280 pharmacologically active compounds. The master library plate consists of 80 compounds per 96 well plate at 10 mM concentration dissolved in DMSO. A screening plate was made by diluting the master plate to yield 1 mM concentration, so as to treat the cells at a final concentration of 10 μM. Screening this library would reveal if any known therapeutics specifically target Bcl-2 and if they are effective in treating Bcl-2 overexpressing cancers.

Another exemplary embodiment, is the ChemBridge DIVERset™ library, a more diverse library with a broad range of pharmacophore structural diversity. The Chem- Bridge library was also prepared by diluting the master plate from 10 mM to 1 mM in a 96 well plate format with 80 compounds per plate.

In some embodiments, in vitro methods of screening for agents that convert Bcl-2 from its anti-apoptotic to its pro-apoptotic form are provided. In certain embodiments, the screening methods comprise contacting a first population of cells expressing or overexpressing Bcl-2 and a second population of cells, wherein the second population does not express Bcl-2 or expresses less Bcl-2 compared to the first population of cells, with the agent and comparing cell viability of the two cell populations.

Figure 2:
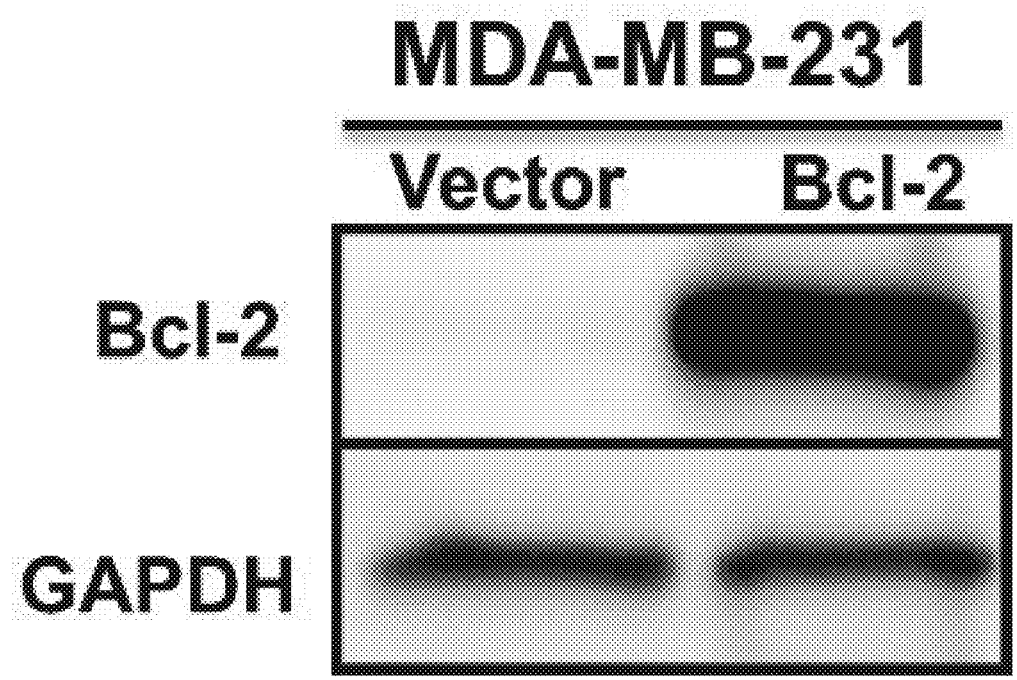
FIG. 2 represents a Western Blot showing Bcl-2 high expression in MDA-MB-231 cells. After generating stable clones of Bcl-2 high expressing cell along with their vector controls a moderately high expressing clone of MDA-MB-231 cells was selected for screening.
Figure 3:
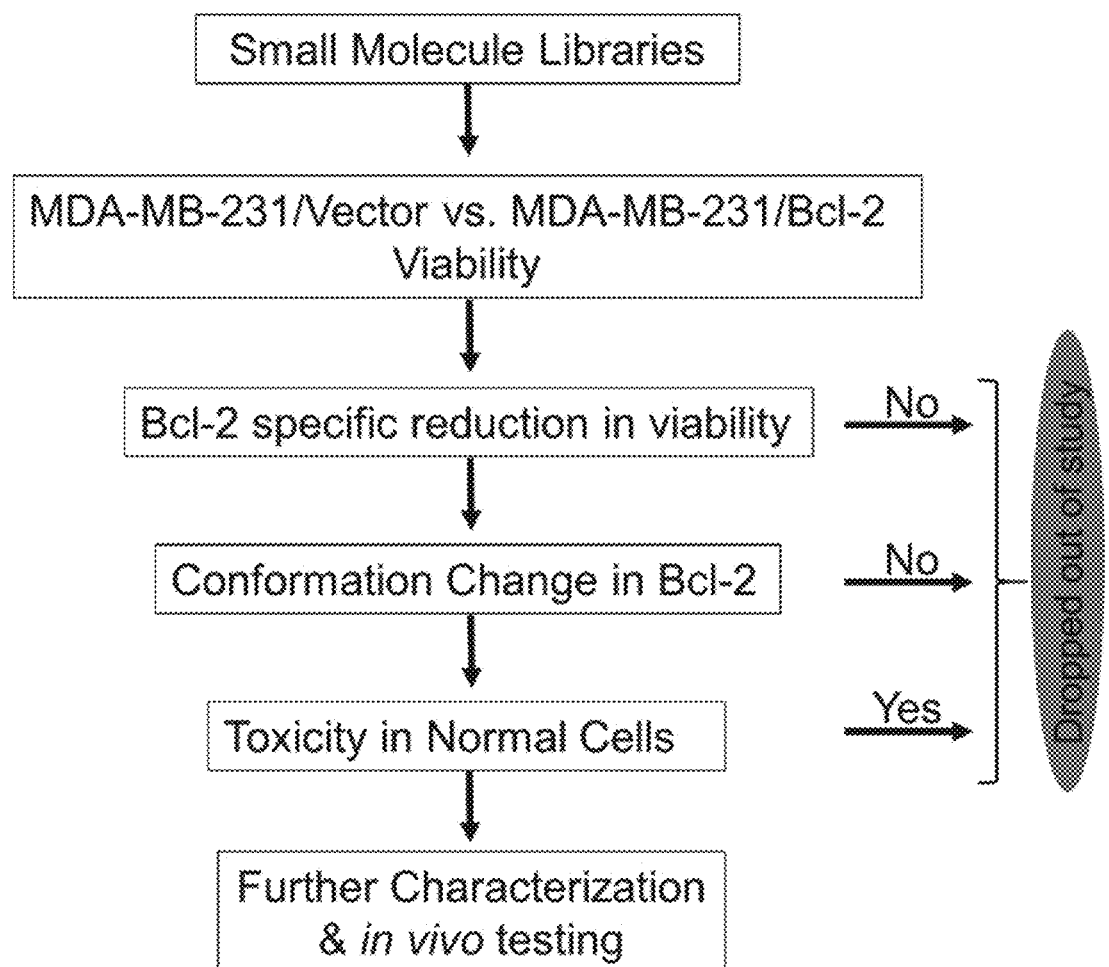
FIG. 3 depicts a schematic of the screening process for identification of small molecules that selectively induce apoptosis in Bcl-2 high expressing cells. A 1280 compound LOPAC library and 50,000 compounds from the ChemBridge DIVERset library were screened in a viability assay. The hits were then re-validated in a confirmatory screen. After final confirmation 2 compounds from LOPAC library and 6 from ChemBrigde library were shortlisted for further characterization.
Figure 4:
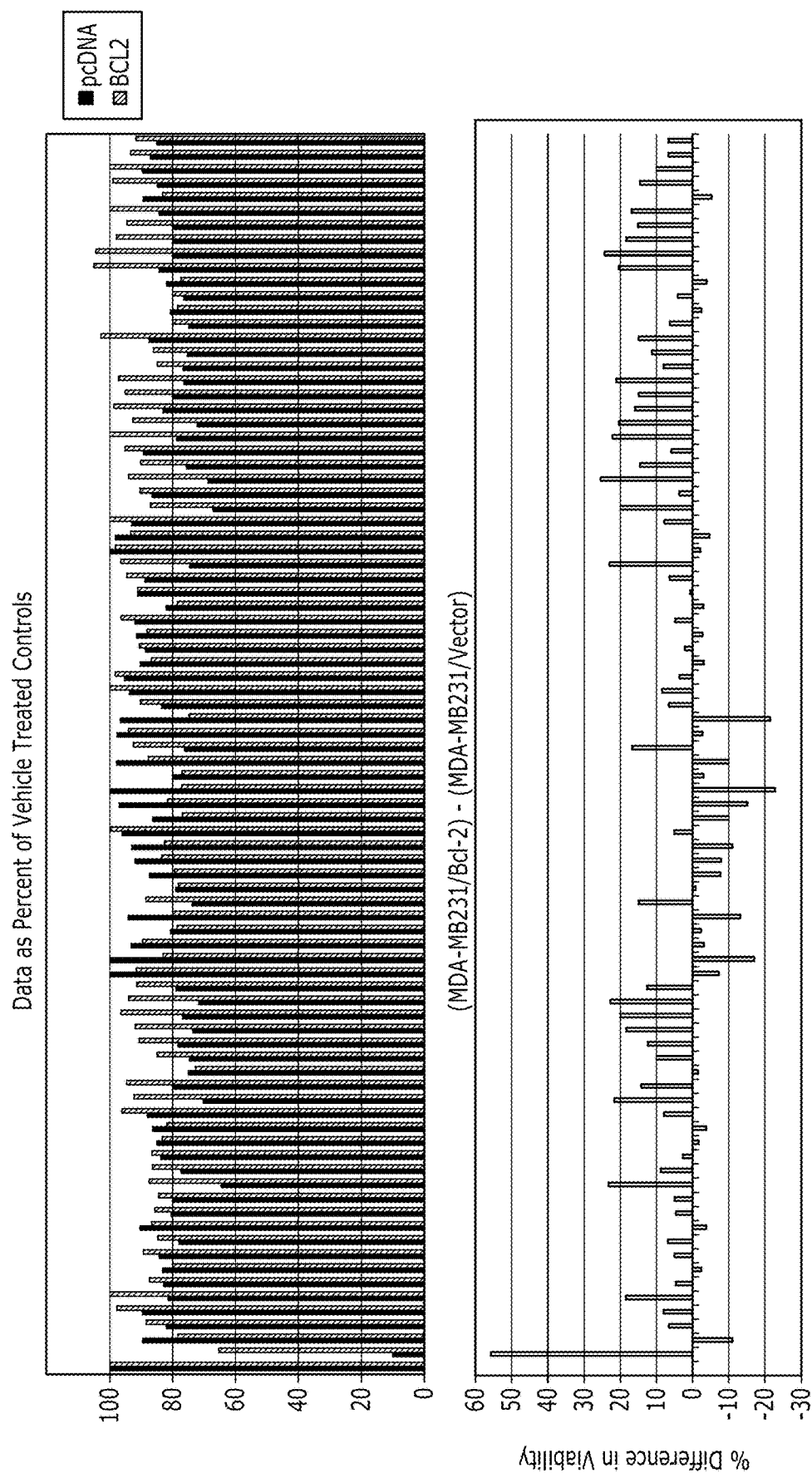
FIG. 4 shows representative data from screening. Screening was performed in 96 well plates using 4000 cells per well of MDA-MB-231 high and low expressing cells. Treatment was done using 10 µM concentration of the test compounds for 24 h at 10% serum conditions. Compounds having 20% or more reduction in viability in Bcl-2 high expressing cells were shortlisted for further testing (negative scale, lower graph).

In one example, a triple negative breast cancer cell line, MDA-MB-231, was used for screening these libraries. The MDA-MB-231 cells were transfected to stably express high levels of Bcl-2 (MDA-MB-231/Bcl-2) along with their vector controls (MDA-MB-231/Vector) (FIG. 2) These cell lines were treated with the chemical libraries at a final concentration of 10 μM for 24 h with 1% DMSO as vehicle control in a 96 well plate. At the end of the assay, cell viability was determined using the cell titer Glo assay. This chemical genetic approach yielded compounds that preferentially induced cell death in Bcl-2 high expressing cells (MDA-MB-231/Bcl-2), compared to cells expressing no Bcl-2 or cells expressing less Bcl-2, e.g., their vector controls. A hit was defined as a compound inducing more than 20% reduction in viability of MDA-MB-231/Bcl-2 cells, compared to vector controls (MDA-MB-231/Vector). In the next step these shortlisted small molecules were tested for their ability to convert the conformation of Bcl-2 into a pro-apoptotic one. A schematic of the screening process is given in FIG. 3. A representative output of the data from the initial screen is shown in FIG. 4.

Hits from the primary screen were reconfirmed using the compounds from the library plates. About 15 hits from LOPAC library and about 240 hits from ChemBridge library were retested for confirmation. Of the 15 hits from LOPAC library only 5 hits were reconfirmed and of the 240 hits from the ChemBridge library only 26 were reconfirmed. The reconfirmed compounds were then re-ordered in higher amounts to be revalidated. Of the re-ordered compounds only 2 compounds from the LOPAC screen and 6 compounds from the ChemBridge library were revalidated. The structure and IUPAC names of these revalidated compounds are given in Table 1. These compounds were further characterized for their role in changing conformation of Bcl-2 and inducing apoptosis in a Bcl-2 dependent way.

Figure 5:
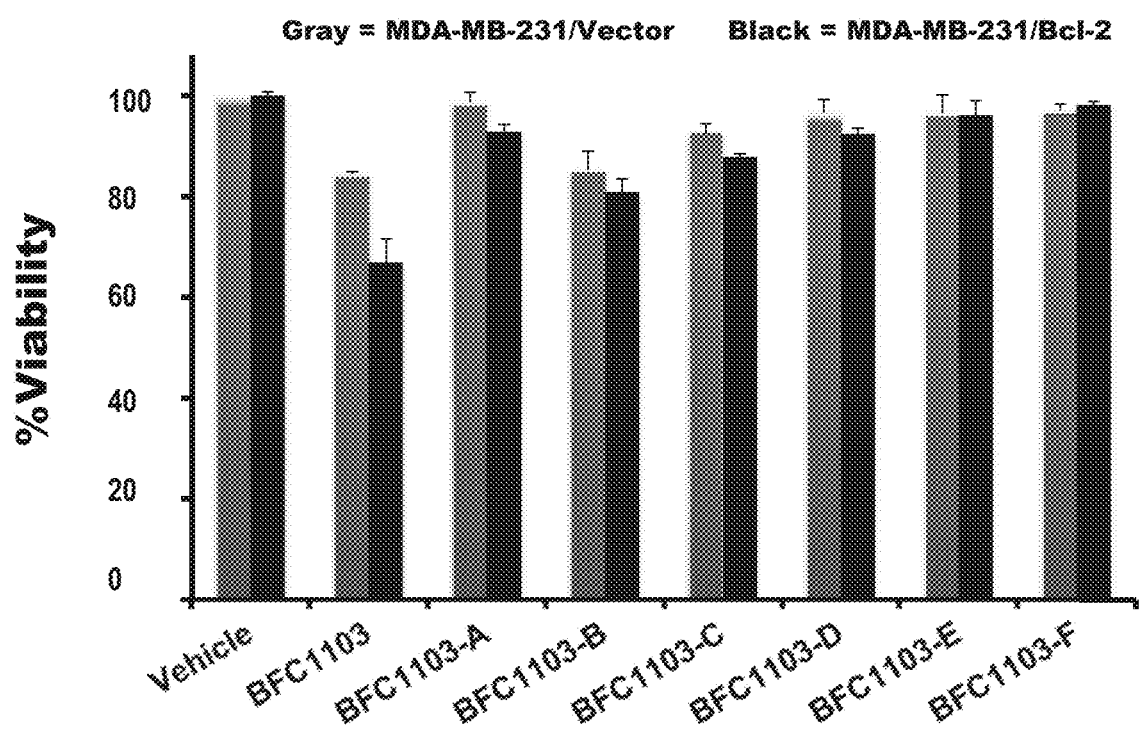
FIG. 5 demonstrates that certain structural analogs of BFC1103 do not show Bcl-2 dependency. Structural analogs of BFC1103 were treated along with BFC1103 in MDA-MB-231 cells with high and low expression of Bcl-2 in a viability assay using 10 µM concentration for 24 h in triplicate wells. Among all the analogs only BFC1103 had a Bcl-2 selective induction of cell death.
Figure 6:
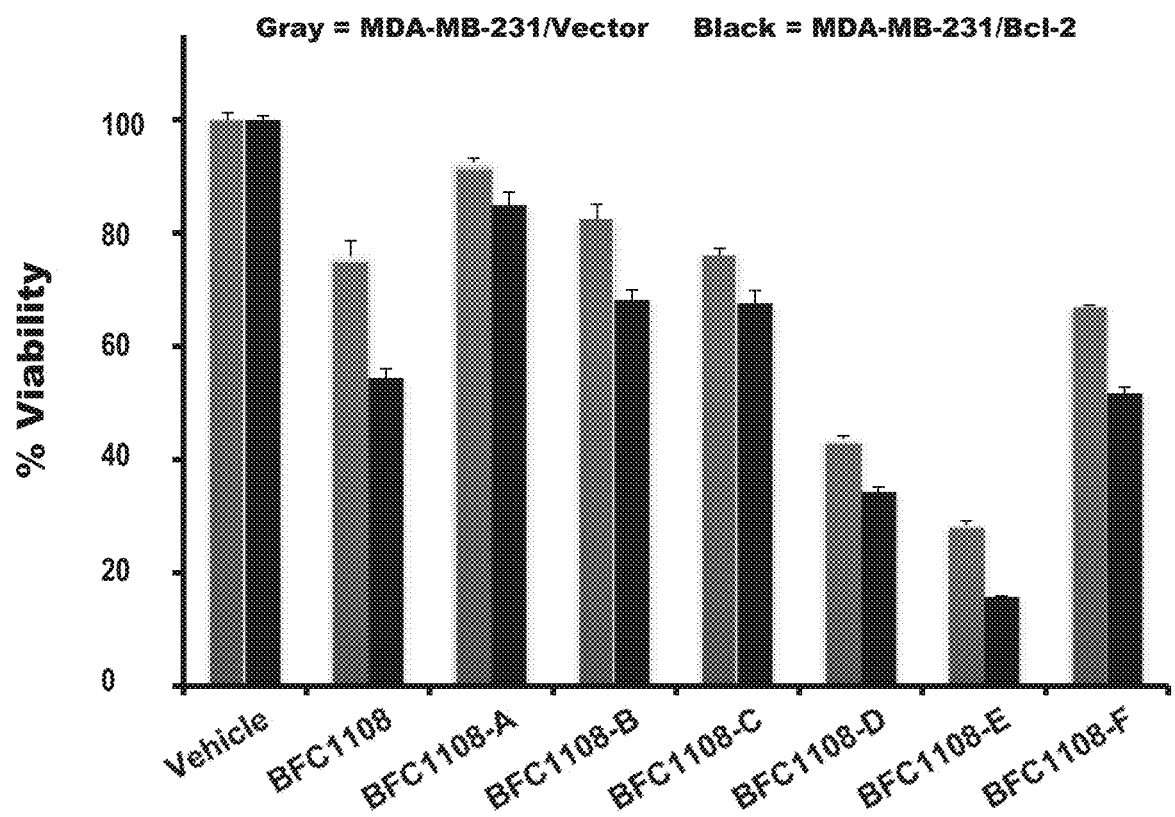
FIG. 6 demonstrates that structural analogs of BFC1108 do not show better Bcl-2 selectivity. Structural analogs of BFC1108 were treated along with BFC1108 in MDA-MB-231 cells with high and low expression of Bcl-2 in a viability assay using 10 µM concentration for 24 h in triplicate wells. Among all the analogs only BFC1108 had better Bcl-2 selective induction of cell death.
Figure 7:
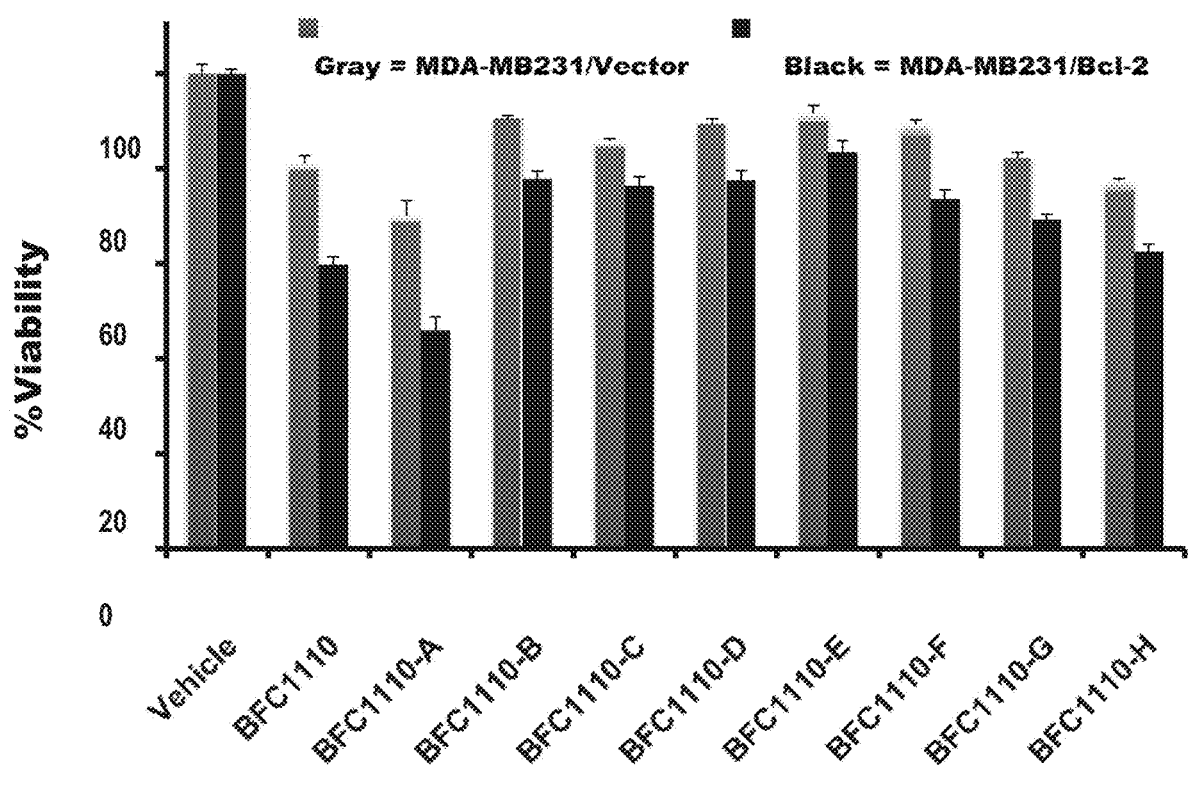
FIG. 7 demonstrates Bcl-2 dependency of structural analogs of BFC1110. Structural analogs of BFC1110 were treated along with BFC1110 in MDA-MB-231 cells with high and low expression of Bcl-2 in a viability assay using 10 µM concentration for 24 h in triplicate wells. Among all the analogs only BFC1110-A (BFC1111) had comparable Bcl-2 selective induction of cell death as the parent BFC1110.
Figure 8:
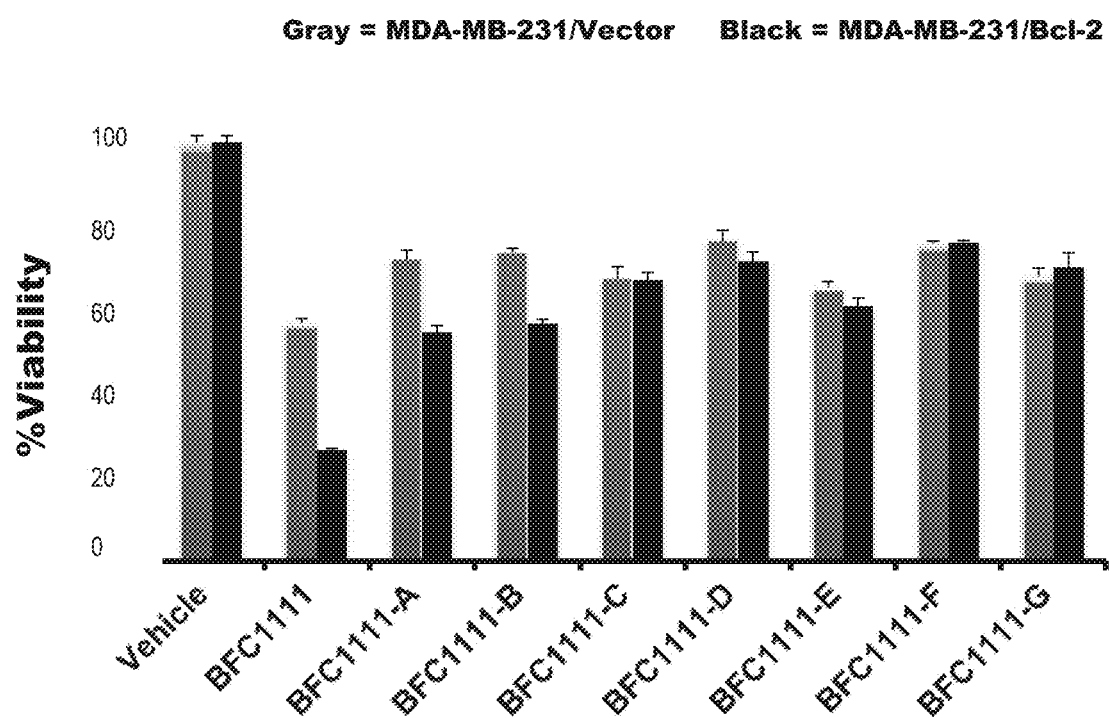
FIG. 8 demonstrates Bcl-2 dependency of structural analogs of BFC1111. Structural analogs of BFC1111 were treated along with BFC1111 in MDA-MB-231 cells with high and low expression of Bcl-2 in a viability assay using 10 µM concentration for 24 h in triplicate wells. None of the analogs BFC1111 had a better Bcl-2 selective induction of cell death.

In order to optimize the revalidated compounds for better potency and drug like properties, structural analogs were tested in a similar manner as the initial screening. The closest structural analogs were selected based on the availability from the chemical suppliers at the time of revalidation. Table 2 contains the structural analogs of BFC1103 along with their IUPAC names. Of the analogs of BFC1103, only BFC1103 showed Bcl-2 dependency and thus was selected for further characterization. FIG. 5 compares the analogs of BFC1103 in the viability assay using the MDA-MB-231 system. Similarly, BFC1108 was compared with its structural analogs. Table 3 shows the structures and the IUPAC names of the analogs of BFC1108 that were tested. Although some analogues of BFC1108 had Bcl-2 dependent effects, the parent compound BFC1108 was selected for further characterization (FIG. 6). Of the BFC1110 analogues (Table 4), BFC1110-A had good Bcl-2 dependent effects in MDA-MB-231 cells (FIG. 2.6) and was further optimized with closer analogues (Table 5). However, BFC1110-A (relabeled as BFC11111) had better Bcl-2 dependent effects and was selected for further characterization (FIG. 8). In conclusion, a total of 8 small molecules were identified that induce Bcl-2 dependent reduction in viability in MDA-MB-231 cells.

TABLE 1

Revalidated hits form LOPAC and ChemBridge Libraries

| Name | IUPAC Name | Structure |
| --- | --- | --- |
| Methotrexate | (2S)-2-[[4-[(2,4 diaminopteridin-6-yl)methylmethylamino]benzoyl]amino] pentanedioc acid | 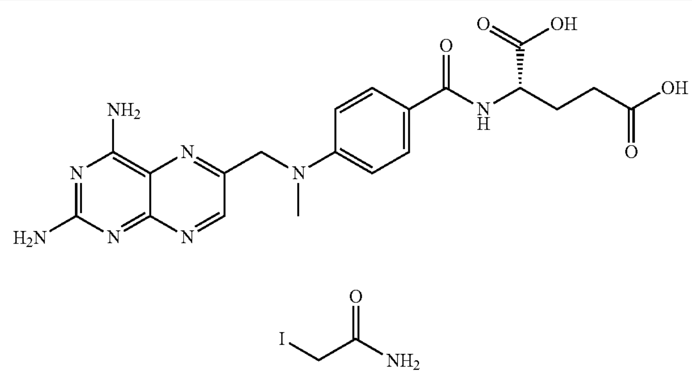 |
| Iodoacetamide | 2-Iodo acetamide | |
| BFC1103 | N-2-benzyl-N-1-(4-butylphenyl)-N-2-(methylsulfo-nyl) glycinamide | 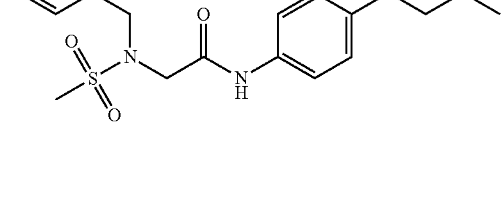 |

TABLE 1-continued

Revalidated hits form LOPAC and ChemBridge Libraries

| Name | IUPAC Name | Structure |
| --- | --- | --- |
| BFC1108 | 5-chloro-N-(2-ethoxyphenyl)-2-[(4-methoxybenzoyl)amino]-benzamide | 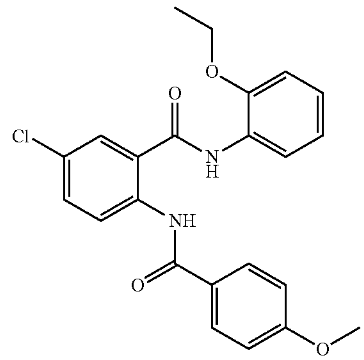 [SMILES: CCOc1ccccc1NC(=O)c1cc(Cl)ccc1NC(=O)c1ccc(OC)cc1] |
| BFC1110 | 2-({2-[1-(2-methoxyethyl)-2,5-dimethyl-1H-pyrrol-3-yl]-2-oxoethyl}thio)-5,6-dimethyl-3-phenylthieno[2,3-d]pyrimidin-4(3H)-one | 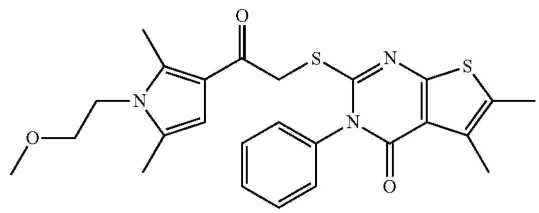 |
| BFC1111 | 2-[(2-methoxy-5-nitrobenzyl)thio]-3-phenyl-5,6,7,8-tetrahydro[1]benzothieno[2,3-d]pyrimidin-4(3H)-one | 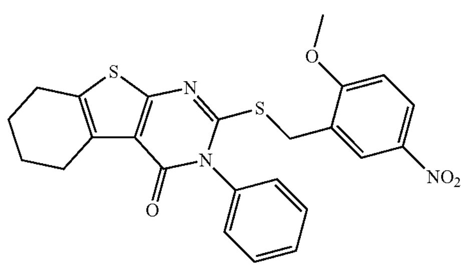 [SMILES: COc1ccc([N+](=O)[O-])cc1CSc1nc2sc3c(c2c(=O)n1-c1ccccc1)CCCC3] |
| BFC1105 | 3-{[2,4-dichlorophenoxy)acetyl]amino}-N-isobutyl benzamide | 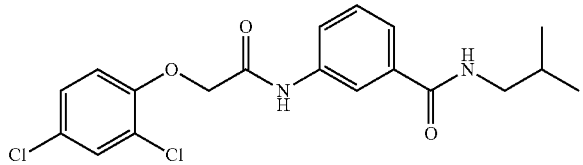 [SMILES: CC(C)CNC(=O)c1cccc(NC(=O)COc2ccc(Cl)cc2Cl)c1] |
| BFC1107 | 4-allyl-1-[2-(4-fluorophenoxy)ethoxy]-2-meth-oxybenzene | 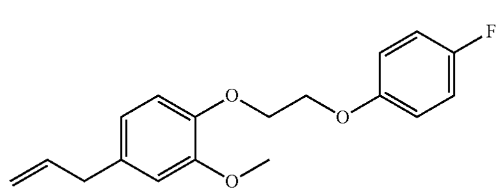 [SMILES: C=CCc1ccc(OCCOc2ccc(F)cc2)c(OC)c1] |

TABLE 2

Structural analogs of BFC1103. Six structural analogs (A-F) were obtained from ChemBridge. Analogs were selected based on subtle changes in side group chemistry.

| Name | IUPAC Name | Structure |
| --- | --- | --- |
| BFC1103-A | N~2~-benzyl-N~1~-(3,4-dimethylphenyl)-N~2~-(methylsulfonyl) glycinamide | 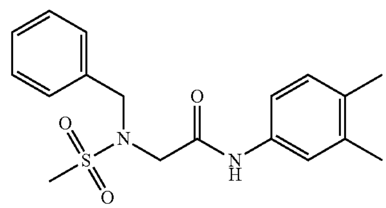 [SMILES: Cc1ccc(NC(=O)CN(Cc2ccccc2)S(C)(=O)=O)cc1C] |
| BFC1103-B | N~2~-(4-chlorobenzyl)-N~1~-(4-ethylphenyl)-N~2~-(methylsulfonyl) glycinamid | 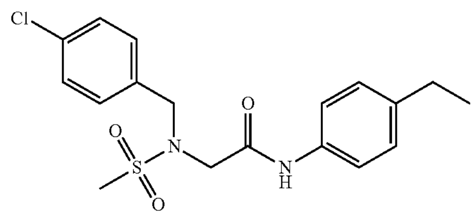 [SMILES: CCc1ccc(NC(=O)CN(Cc2ccc(Cl)cc2)S(C)(=O)=O)cc1] |
| BFC1103-C | N~2~-benzyl-N~2~-(methylsulfonyl)-N~1~-[3-(trifluoromethyl)phenyl]-glycinamide | 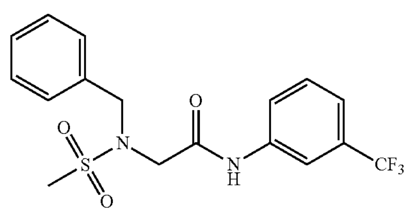 [SMILES: CS(=O)(=O)N(CC(=O)Nc1cccc(C(F)(F)F)c1)Cc1ccccc1] |
| BFC1103-D | N~1~-(4-butylphenyl)-N~2~-methyl-N~2~-(methylsulfonyl)glycin-amide | 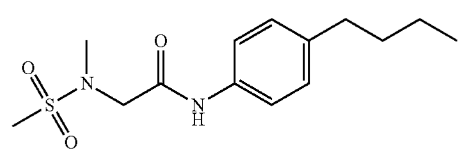 [SMILES: CCCCc1ccc(NC(=O)CN(C)S(C)(=O)=O)cc1] |
| BFC1103-E | methyl 4-{[N-benzyl-N-(methylsulfonyl)glycyl]-amino}benzoate | 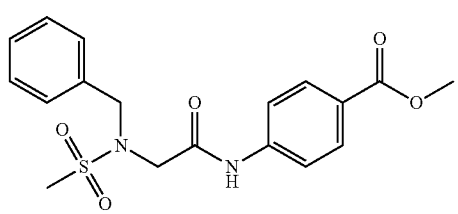 [SMILES: COC(=O)c1ccc(NC(=O)CN(Cc2ccccc2)S(C)(=O)=O)cc1] |
| BFC1103-F | N~2~-(4-fluorobenzyl)-N~2~-(methylsulfonyl)-N~1~-phenyl glycinamide | 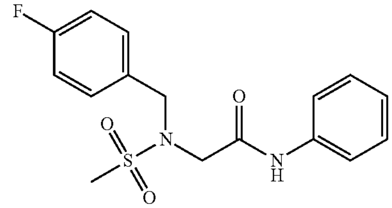 [SMILES: CS(=O)(=O)N(CC(=O)Nc1ccccc1)Cc1ccc(F)cc1] |

TABLE 3

Structural analogs of BFC1108. Six structural analogs (A-F) were obtained from ChemBridge. Analogs were selected based on subtle changes in side group chemistry.

| | | |
|---|---|---|
| BFC1108-A | 3-chloro-4-ethoxy-N-(2-ethoxyphenyl)-benzamide | 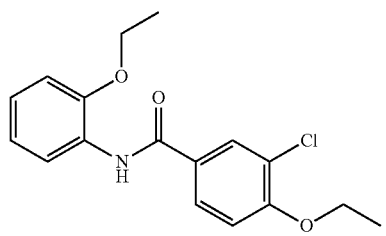 [SMILES: CCOc1ccc(C(=O)Nc2ccccc2OCC)cc1Cl] |
| BFC1108-B | 2,4-dichloro-N-(4-chloro-2-{[(2-ethoxyphenyl)amino]-carbonyl}phenyl)benz-amide | 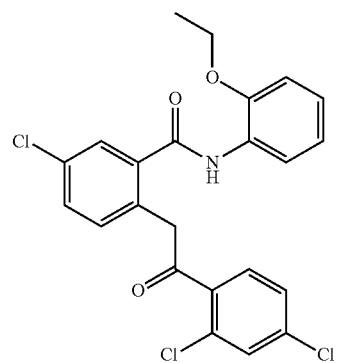 [SMILES: CCOc1ccccc1NC(=O)c1cc(Cl)ccc1CC(=O)c1ccc(Cl)cc1Cl] |
| BFC1108-C | N-(4-chloro-2-{[(2-ethoxyphenyl)amino]carbonyl}phenyl)-2-furamide | 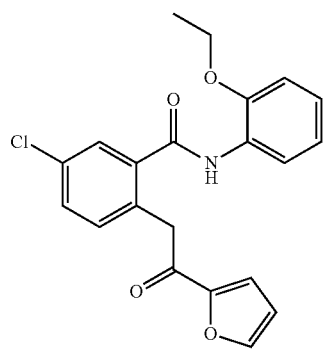 [SMILES: CCOc1ccccc1NC(=O)c1cc(Cl)ccc1CC(=O)c1ccco1] |
| BFC1108-D | 3-chloro-N-(2-{[(2-methoxyphenyl)amino]carbonyl}phenyl)-4-methyl benzamide | 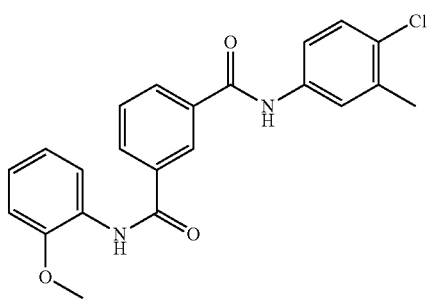 [SMILES: COc1ccccc1NC(=O)c1cccc(C(=O)Nc2ccc(Cl)c(C)c2)c1] |

TABLE 3-continued

Structural analogs of BFC1108. Six structural analogs (A-F) were obtained from ChemBridge. Analogs were selected based on subtle changes in side group chemistry.

| | | |
|---|---|---|
| BFC1108-E | 3,5-dichloro-N-(2-ethoxyphenyl)-2-[(3-nitrobenzoyl)amino]benzamide | |
| BFC1108-F | 2-[(4methoxybenzoyl)amino]-N-(2-{[(2-methoxyphenyl)amino]carbonyl}phenyl)benz-amide | |

TABLE 4

Structural analogs of BFC1110. Eight structural analogs (A-H) were obtained from ChemBridge. Analogs were selected based on subtle changes in side group chemistry.

| Name | IUPAC Name | Structure |
|---|---|---|
| BFC1110-A | 2-[(2-methoxy-5-nitrobenzyl)thio]-3-phenyl-5,6,7,8-tetrahydro[1]benzothieno[2,3-d]pyrimidin-4(3H)-one | 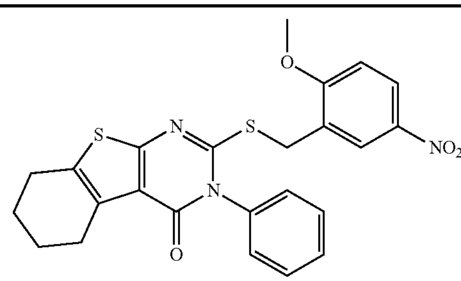 |
| BFC1110-B | 3-(4-fluorophenyl)-2-{[2-oxo-2-(1-pyrrolidinyl)ethyl]thio}-5,6,7,8-tetrahydro[1][2,3-d]pyrimidin-4(3H)-one | 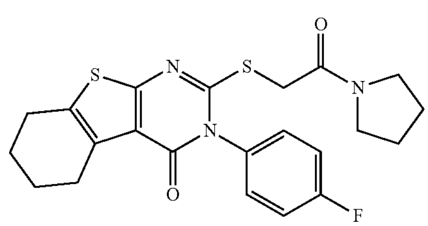 [SMILES: O=C(CSc1nc2sc3c(c2c(=O)n1-c1ccc(F)cc1)CCCC3)N1CCCC1] |
| BFC1110-C | 2-{[2-(4-chlorophenyl)-2-oxoethyl]thio}-5,6-dimethyl-3-phenylthieno[2,3-d]pyrimidin-4(3H)-one | 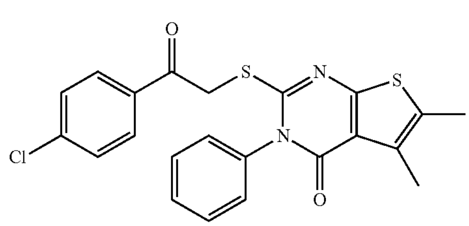 [SMILES: Cc1sc2nc(SCC(=O)c3ccc(Cl)cc3)n(-c3ccccc3)c(=O)c2c1C] |

TABLE 4-continued

*Structural analogs of BFC1110. Eight structural analogs (A-H) were obtained from ChemBridge. Analogs were selected based on subtle changes in side group chemistry.*

| Name | IUPAC Name | Structure |
| --- | --- | --- |
| BFC1110-D | 5,6-dimethyl-2-{[(2-methyl-1,3-thiazol-4-yl)methyl]thio}-3-phenylthieno[2,3-d]pyrimidin-4(3H)-one | 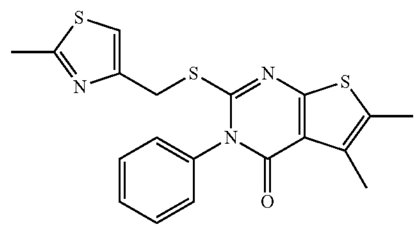 |
| BFC1110-E | 2-({2-[4-(2-hydroxyethyl)-1-piperazinyl]-2-oxoethyl}thio)-5,6-dimethyl-3-phenyl-thieno[2,3-d]pyrimidin-4(3H)-one | 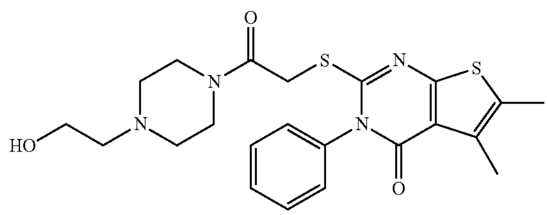 [SMILES: Cc1sc2nc(SCC(=O)N3CCN(CCO)CC3)n(-c3ccccc3)c(=O)c2c1C] |
| BFC1110-F | 5,6-dimethyl-2-{[2-(4-nitrophenyl)-2-oxo-ethyl]thio}-3-phenyl-thieno[2,3-d]pyrimidin-4(3H)-one | 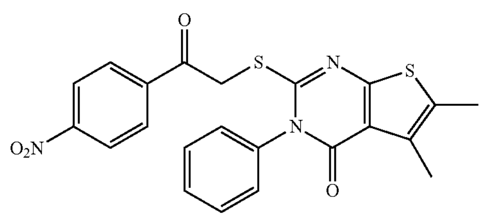 [SMILES: Cc1sc2nc(SCC(=O)c3ccc([N+](=O)[O-])cc3)n(-c3ccccc3)c(=O)c2c1C] |
| BFC1110-G | 2-{[2-(4-fluorophenoxy)ethyl]thio}-5,6-dimethyl-3-phenylthieno[2,3-d]pyrimidin-4(3H)-one | 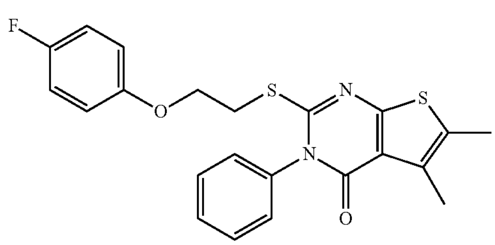 [SMILES: Cc1sc2nc(SCCOc3ccc(F)cc3)n(-c3ccccc3)c(=O)c2c1C] |
| BFC1110-H | 2-{[2-oxo-2-(2-thienyl)ethyl]thio}-3-phenyl-5,6,7,8-tetrahydro[1]benzothieno[2,3-d]pyrimidin-4(3H)-one | 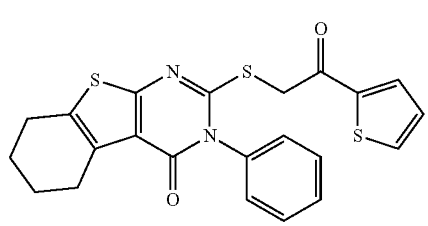 [SMILES: O=C(CSc1nc2sc3c(c2c(=O)n1-c1ccccc1)CCCC3)c1cccs1] |

TABLE 5

Structural analogs of BFC1111. Eight structural analogs (A-H) were obtained from ChemBridge. Analogs were selected based on subtle changes in side group chemistry.

| Name | IUPAC Name | Structure |
| --- | --- | --- |
| BFC1111-A | 2-[(4-nitrobenzyl)thio]-3-phenyl-5,6,7,8-tetrahydro[1]benzothieno[2,3-d]pyrimidin-4(3H)-one | 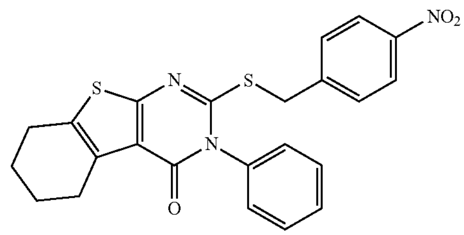 [SMILES: O=c1c2c3c(sc2nc(SCc2ccc([N+](=O)[O-])cc2)n1-c1ccccc1)CCCC3] |
| BFC1111-B | 2-(benzylthio)-3-phenyl-5,6,7,8-tetrahydro[1]benzothieno[2,3-d]pyrimidin-4(3H)-one | 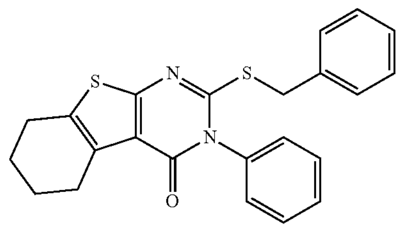 [SMILES: O=c1c2c3c(sc2nc(SCc2ccccc2)n1-c1ccccc1)CCCC3] |
| BFC1111-C | 2-[(4-methoxybenzyl)thio]-3-phenyl-5,6,7,8-tetrahydro[1]benzothieno[2,3-d]pyrimidin-4(3H)-one | 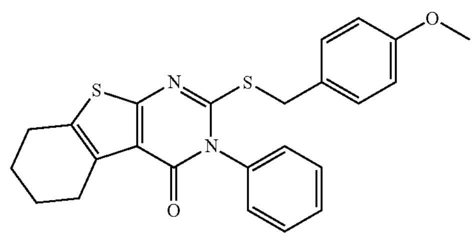 [SMILES: COc1ccc(CSc2nc3sc4c(c3c(=O)n2-c2ccccc2)CCCC4)cc1] |
| BFC1111-D | {[3-(4-ethoxyphenyl)-4-oxo-3,4,5,6,7,8-hexahydro[1]-benzothieno[2,3-d]pyrimidin-2-yl]thio}acetic acid | 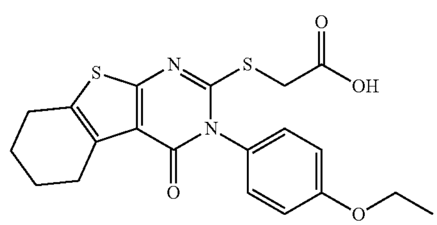 [SMILES: CCOc1ccc(-n2c(SCC(=O)O)nc3sc4c(c3c2=O)CCCC4)cc1] |
| BFC1111-E | 2-{[3-(4-ethoxyphenyl)-4-oxo-3,4,5,6,7,8-hexahydro[1]-benzothieno[2,3-d]pyrimidin-2-yl]thio}acetamide | 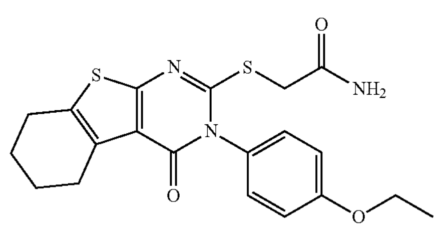 [SMILES: CCOc1ccc(-n2c(SCC(N)=O)nc3sc4c(c3c2=O)CCCC4)cc1] |
| BFC1111-F | 4-({[3-(4-methoxyphenyl)-4-oxo-3,4,5,6,7,8-hexahydro[1]benzothieno[2,3-d]pyrimidin-2-yl]thio}methyl)benzoic acid | 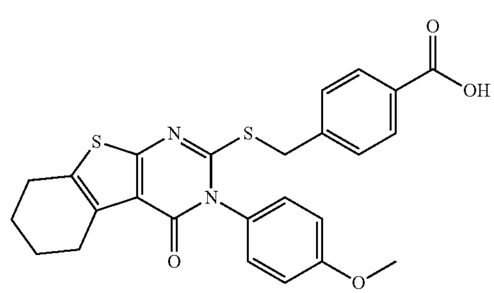 [SMILES: COc1ccc(-n2c(SCc3ccc(C(=O)O)cc3)nc3sc4c(c3c2=O)CCCC4)cc1] |

TABLE 5-continued

Structural analogs of BFC1111. Eight structural analogs (A-H) were obtained from ChemBridge. Analogs were selected based on subtle changes in side group chemistry.

| Name | IUPAC Name | Structure |
|---|---|---|
| BFC1111-G | 7-tert-butyl-2-[(4-methoxybenzyl)thio]-3-phenyl-5,6,7,8-tetrahydro[1]-benzothieno[2,3-d]pyrimidin-4(3H)-one | 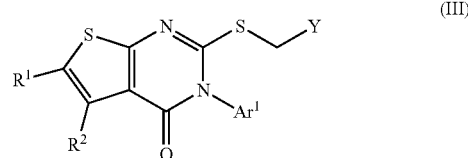 |

In some embodiments, the agent of the methods disclosed herein is a structural analog of compound BFC1103. Such structural analogs of compound BFC1103 include compounds of Formula (I):

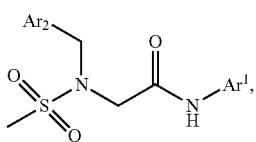

its isomer, tautomer, hydrate, or salt,
wherein:
  $Ar^1$ is optionally substituted C6-C10 aryl or optionally substituted C5-C10 heteroaryl; and
  $Ar^2$ is H, optionally substituted C6-C10 aryl, or optionally substituted C5-C10 heteroaryl.

In other embodiments, the agent of the methods disclosed herein is a structural analog of compound BFC1108. Such structural analogs of compound BFC1108 include compounds of Formula (II):

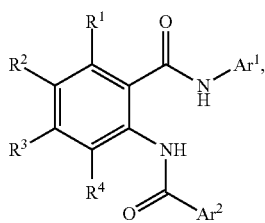

its isomer, tautomer, hydrate, or salt,
wherein:
  $Ar^1$ is optionally substituted C6-C10 aryl or optionally substituted C5-C10 heteroaryl;
  $Ar^2$ is optionally substituted C6-C10 aryl, or optionally substituted C5-C10 heteroaryl; and
  $R^1$, $R^2$, $R^3$, and $R^4$ are independently H, halogen, optionally substituted C1-C8 alkyl, optionally substituted C1-C8 alkenyl, optionally substituted C1-C8 alkynyl, O(C1-C8 alkyl), or C(O)NHR, wherein R is optionally substituted C1-C8 alkyl, optionally substituted C6-C10 aryl, or optionally substituted C5-C10 heteroaryl.

In certain embodiments, the agent of the methods disclosed herein is a structural analog of compound BFC1110 or BFC1111. Such structural analogs include compounds of Formula (III):

$$\text{(III)}$$

its isomer, tautomer, hydrate, or salt,
wherein:
  $Ar^1$ is optionally substituted C6-C10 aryl or optionally substituted C5-C10 heteroaryl;
  $R^1$ and $R^2$ are independently H, halogen, optionally substituted C1-C8 alkyl, optionally substituted C1-C8 alkenyl, optionally substituted C1-C8 alkynyl, O(C1-C8 alkyl), or C(O)NHR, wherein R is optionally substituted C1-C8 alkyl, optionally substituted C6-C10 aryl, or optionally substituted C5-C10 heteroaryl; or together with the carbon atoms to which each is attached, $R^1$ and $R^2$ form an optionally substituted 6-membered cycle;
  Y is COOH, $CONH_2$, optionally substituted C6-C10 aryl, optionally substituted C5-C10 heteroaryl, or C(O)X; and
  X is optionally substituted C6-C10 aryl, optionally substituted C5-C10 heteroaryl, or optionally substituted C3-C10 heteroaryl.

As used herein, the terms "alkyl," "alkenyl," and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as C1-C10 or C1-10. The term "heteroalkyl," "heteroalkenyl," and "heteroalkynyl," as used herein, mean the corresponding hydrocarbons wherein one or more chain carbon atoms have been replaced by a heteroatom. Exemplary heteroatoms include N, O, S, and P. When heteroatoms are allowed to replace carbon atoms, for example, in heteroalkyl groups, the numbers describing the group, though still written as e.g.

C3-C10, represent the sum of the number of carbon atoms in the cycle or chain plus the number of such heteroatoms that are included as replacements for carbon atoms in the cycle or chain being described.

Typically, the alkyl, alkenyl, and alkynyl substituents of the invention contain 1-10 carbon atoms (alkyl) or 2-10 carbon atoms (alkenyl or alkynyl). Preferably, they contain 1-8 carbon atoms (alkyl) or 2-8 carbon atoms (alkenyl or alkynyl). Sometimes they contain 1-4 carbon atoms (alkyl) or 2-4 carbon atoms (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl, and alkynyl groups can be optionally substituted to the extent that such substitution makes sense chemically. Typical substituents include, but are not limited to, halogens (F, Cl, Br, I), =O, =N—CN, =N—OR, =NR, OR, $NR_2$, SR, $SO_2R$, $SO_2NR_2$, $NRSO_2R$, $NRCONR_2$, NRC(O)OR, NRC(O)R, CN, C(O)OR, C(O)$NR_2$, OC(O)R, C(O)R, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halogens (F, Cl, Br, I), =O, =N—CN, =N—OR', =NR', OR', $NR'_2$, SR', $SO_2R'$, $SO_2NR'_2$, $NR'SO_2R'$, $NR'CONR'_2$, NR'C(O)OR', NR'C(O)R', CN, C(O)OR', C(O)$NR'_2$, OC(O) R', C(O)R', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

While "alkyl" as used herein includes cycloalkyl and cycloalkylalkyl groups, the term "cycloalkyl" is used herein to describe a carbocyclic non-aromatic group that is connected via a ring carbon atom, and "cycloalkylalkyl" is used to describe a carbocyclic non-aromatic group that is connected to the molecule through an alkyl linker. Similarly, "heterocyclyl" is used to identify a non-aromatic cyclic group that contains at least one heteroatom as a ring member and that is connected to the molecule via a ring atom, which may be C or N; and "heterocyclylalkyl" may be used to describe such a group that is connected to another molecule through an alkylene linker. As used herein, these terms also include rings that contain a double bond or two, as long as the ring is not aromatic.

"Aromatic" or "aryl" substituent or moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms. Suitable heteroatoms include N, O, and S, inclusion of which permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl, and fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halogens (F, Cl, Br, I), OR, $NR_2$, SR, $SO_2R$, $SO_2NR_2$, $NRSO_2R$, $NRCONR_2$, NRC(O)OR, NRC(O)R, CN, C(O)OR, C(O)$NR_2$, OC(O)R, C(O)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

"Optionally substituted," as used herein, indicates that the particular group being described may have one or more hydrogen substituents replaced by a non-hydrogen substituent. In some optionally substituted groups or moieties, all hydrogen substituents are replaced by a non-hydrogen substituent. If not otherwise specified, the total number of such substituents that may be present is equal to the number of H atoms present on the unsubstituted form of the group being described. Where an optional substituent is attached via a double bond, such as a carbonyl oxygen or oxo (=O), the group takes up two available valences, so the total number of substituents that may be included is reduced according to the number of available valences

REFERENCES

1. Tsujimoto, Y., Finger, L. R., Yunis, J., Nowell, P. C. & Croce, C. M. Cloning of the chromosome breakpoint of neoplastic B cells with the t(14;18) chromosome translocation. *Science* 226, 1097-1099 (1984).
2. Tsujimoto, Y., Cossman, J., Jaffe, E. & Croce, C. M. Involvement of the bcl-2 Gene in Human Follicular Lymphoma. *Science* 228, 1440-1443 (1985).
3. Vaux, D. L., Cory, S. & Adams, J. M. Bcl-2 gene promotes haemopoietic cell survival and cooperates with c-myc to immortalize pre-B cells. *Nature* 335, 440-442 (1988).
4. Sattler, M. et al. Structure of Bcl-xL-Bak peptide complex: Recognition between regulators of apoptosis. *Science* 275, 983-986 (1997).
5. Kang, M. H. & Reynolds, C. P. BCL-2 inhibitors: targeting mitochondrial apoptotic pathways in cancer therapy. *Clin. Cancer Res.* 15, 1126-1132 (2009).

6. Degterev, A. et al. Identification of small-molecule inhibitors of interaction between the BH3 domain and Bcl-xL. *Nat Cell Biol* 3, 173-82 (2001).
7. Enyedy, I. J. et al. Discovery of small-molecule inhibitors of Bcl-2 through structure based computer screening. *J Med Chem* 44, 4313-24 (2001).
8. Kitada, S. et al. Discovery, characterization, and structure-activity relationships studies of proapoptotic polyphenols targeting B-cell lymphocyte/leukemia-2 proteins. *J Med Chem* 46, 4259-64 (2003).
9. Nguyen, M. et al. Small molecule obatoclax (GX15-070) antagonizes MCL-1 and overcomes MCL-1-mediated resistance to apoptosis. *Proc Natl Acad Sci USA* 104, 19512-7 (2007).
10. Oltersdorf, T. et al. An inhibitor of Bcl-2 family proteins induces regression of solid tumours. *Nature* 435, 677-681 (2005).
11. Berg, T. Small-molecule inhibitors of protein-protein interactions. *Curr. Op. Drug Disc. Dev.* 11, 666-674 (2008).
12. Petros, A. M. et al. Discovery of a potent and selective Bcl-2 inhibitor using SAR by NMR. *Bioorg Med Chem Lett* 20, 6587-91 (2010).
13. Walensky, L. D. et al. Activation of apoptosis in vivo by a hydrocarbon-stapled BH3 helix. *Science* 305, 1466-70 (2004).
14. Wang, G. et al. Structure-based design of potent small-molecule inhibitors of antiapoptotic Bcl-2 proteins. *J Med Chem* 49, 6139-42 (2006).
15. Qian, J. et al. Discovery of novel inhibitors of Bcl-xL using multiple high-throughput screening platforms. *Anal. Biochem.* 328, 131-138 (2004).
16. Degeretev, A. et al. Identification of small molecule inhibitors of interaction between the BH3 domain and BCL-XL. *Nature Cell Biol.* 3, 173-182 (2001).
17. Lin, B. et al. Conversion of Bcl-2 from protector to killer by interaction with nuclear orphan receptor Nur77/TR3. *cell* 116, 527-540 (2004).
18. Kolluri, S. K. et al. A short Nur77-derived peptide converts Bcl-2 from a protector to a killer. *Cancer Cell* 14, 285-298 (2008).
19. Zhai, D., Jin, C., Satterthwait, A. C. & Reed, J. C. Comparison of chemical inhibitors of antiapoptotic BCL-2 family proteins. *Cell Death Diff.* 13, 1419-1421 (2006). 13. Tzung, S. P. et al. Antimycin A mimics a cell-death-inducing Bcl-2 homology domain 3.*Nat Cell Biol* 3, 183-91 (2001).
20. Zhai, D. et al. High-throughput fluorescence polarization assay for chemical library screening against anti-apoptotic Bcl-2 family member Bcl-2. *Journal of Biomolecular Screening* 17, 350-360 (2012).
21. Tse, C. et al. ABT-263: a potent and orally bioavailable Bcl-2 family inhibitor. *Cancer Res* 68, 3421-8 (2008).
22. Wilson, W. H. et al. Navitoclax, a targeted high-affinity inhibitor of BCL-2, in lymphoid malignancies: a phase 1 dose-escalation study of safety, pharmacokinetics, pharmacodynamics, and antitumour activity. *Lancet Oncol.* 11, 1149-59 (2010).
23. Gandhi, L. et al. Phase 1 study of Navitoclax (ABT-263), a novel Bcl-2 family inhibitor, in patients with small-cell lung cancer and other solid tumors. *J Clin Oncol* 29, 909-16 (2011).
24. Roberts, A. W. et al. Substantial susceptibility of chronic lymphocytic leukemia to BCL2 inhibition: Results of Phase 1 study of navitoclax (ABT-263) in patients with relapsed or refractory disease. *J Clin Onc* (2011).
25. Konopleva, M. et al. Mechanisms of apoptosis sensitivity and resistance to the BH3 mimetic ABT-737 in acute myeloid leukemia. *Cancer Cell* 10, 375-388 (2006).
26. Lin, X. et al. "Seed" analysis of off-target siRNAs reveals an essential role of MCL-1 in resistance to the small-molecule Bcl-2/Bcl-xL inhibitor ABT-737. *Oncogene* 26, 3972-3979 (2007).
27. van Delft, M. F. et al. The BH3 mimetic ABT-737 targets selective Bcl-2 proteins and efficiently induces apoptosis via Bak/Bax if Mcl-1 is neutralized. *Cancer Cell* 10, 389-399 (2006).
28. Yecies, D., Carlson, N. E., Deng, J. & Letai, A. Acquired resistance to ABT-737 in lymphoma cells that up-regulate MCL-1 and BFL-1. *Blood* 115, 3304-13 (2010).
29. Luciano, F. et al. Nur77 converts phenotype of Bcl-B, an antiapoptotic protein expressed in plasma cells and myeloma. *Blood* 109, 3849-3855 (2007).
30. Watkins, C. L. et al. Co-operative membrane disruption between cell-penetrating peptide and cargo: implications for the therapeutic use of the Bcl-2 converter peptide D-NuBCP-9-r8. *Mol. Ther. J. Am. Soc. Gene Ther.* 19, 2124-2132 (2011).
31. Kumar, M. et al. Intracellular delivery of peptide cargos using iron oxide based nanoparticles: studies on antitumor efficacy of a BCL-2 converting peptide, NuBCP-9. *Nanoscale* 6, 14473-14483 (2014).
32. Kumar, M. et al. Novel polymeric nanoparticles for intracellular delivery of peptide Cargos: antitumor efficacy of the BCL-2 conversion peptide NuBCP-9. *Cancer Res.* 74, 3271-3281 (2014).

2. Methotrexate Functionally Converts Bcl-2 into a Pro-Apoptotic Protein

In some embodiments, the agent of the methods disclosed herein is methotrexate (MTX) or a methotrexate analog. In certain embodiments, the methotrexate analog is a compound of Formula (IV):

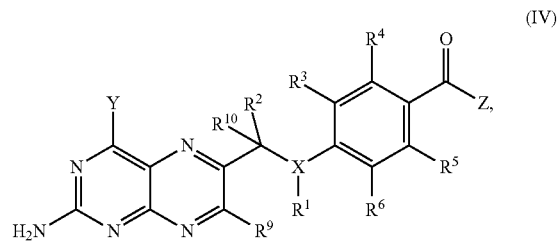

its isomer, tautomer, hydrate, or salt,
wherein:
$R^1$ is H, C1-C8 alkyl, C1-C8 alkenyl, or C1-C8 alkynyl;
$R^2$ is H, C1-C8 alkyl, C1-C8 alkenyl, or C1-C8 alkynyl;
$R^{10}$ is H or $R^{10}$ and $R^2$, taken together, form an oxo group (=O);
$R^3$, $R^4$, $R^5$, and $R^6$ are independently H, halogen, C1-C8 alkyl, C1-C8 alkenyl, C1-C8 alkynyl, or $R^5$ and $R^6$, together with the carbon atoms to which each is attached, form a 5 or 6-membered aromatic or heteroaromatic ring;
$R^9$ is H or $R^9$ and $R^1$ form a C1-C3 alkylene;
Y is $NH_2$ or OH;
X is N or C; and Z is OH, $NH_2$, $OR^8$, or

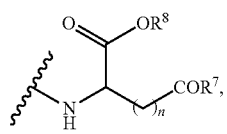

wherein $R^8$ is H or C1-C8 alkyl, n is 1 or 2, and R7 is H, OH, $NH_2$, or C1-C8 alkyl.

Figure 9A:
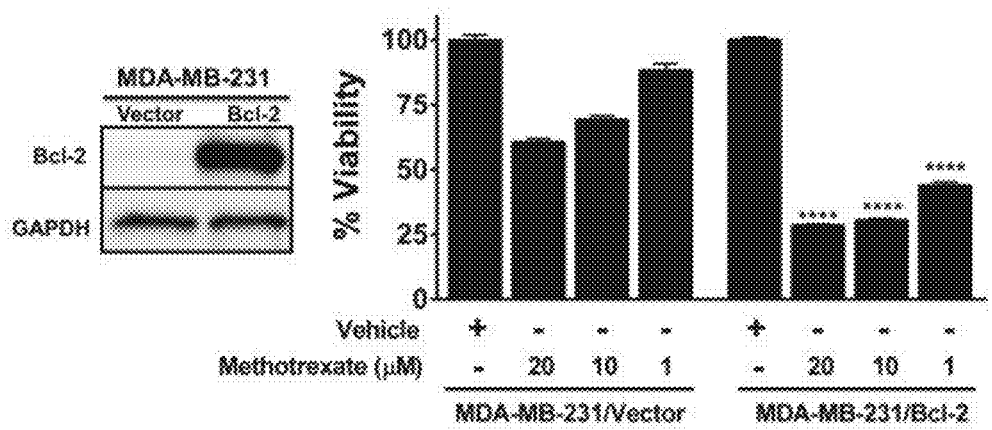
FIG. 9A depicts effect of methotrexate in certain cancer cell types. Left panel: Bcl-2 expression in MDA-MB231 cells transfected with pcDNA control vector (MDA-MB231/Vector) or Bcl-2 expression vector (MDA-MB-231/Bcl-2) was determined by Western blot. Right panel: Cells were exposed to various concentrations of Methotrexate as indicated for 24 h in a medium containing 10% FBS and viability was determined by cell titer glossary.
Figure 9B:
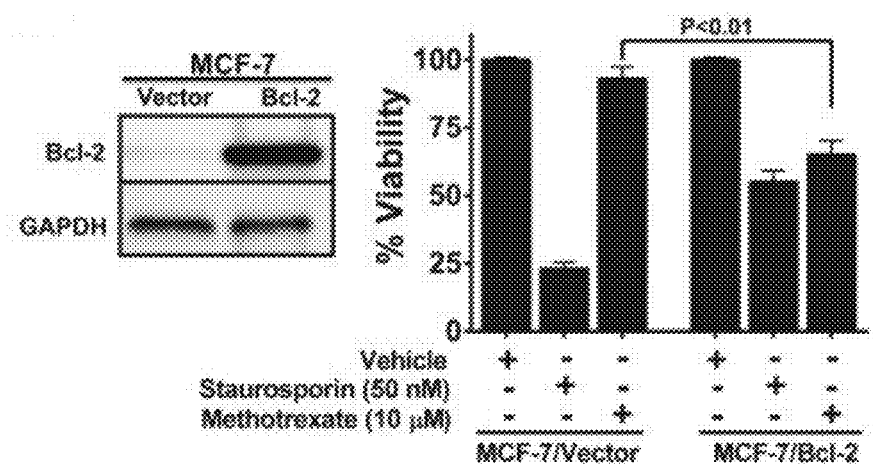
FIG. 9B depicts effect of methotrexate in certain cancer cell types. Left panel: Bcl-2 expression in MCF-7 cells transfected with pcDNA control vector (MCF7/Vector) or Bcl-2 expression vector (MCF7/Bcl-2) was determined by Western blot. Right panel: Cells were exposed to MTX (10 µM) for 24 h in a medium containing 10% FBS and viability was determined by cell titer glo assay.
Figure 9C:
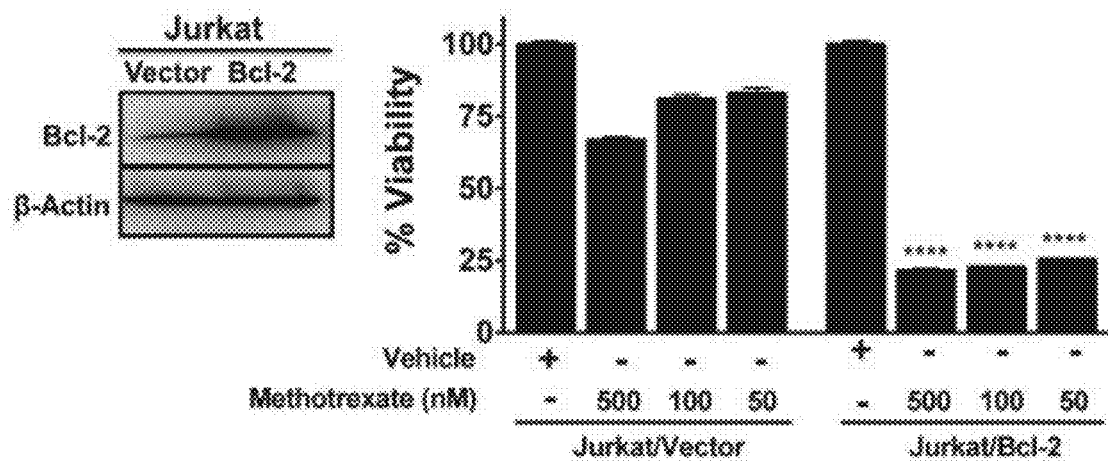
FIG. 9C depicts effect of methotrexate in certain cancer cell types. Left panel: Bcl-2 expression for Jurkat cells transfected with Neo control vector (Jurkats/Vector) or Bcl-2 expression vector (Jurkats/Bcl-2). Right panel: Cells were exposed to various concentrations of Methotrexate as indicated for 24 h in a medium containing 10% FBS and viability was determined by cell titer glo assay.

To identify small molecules that can serve as functional converters of Bcl-2 and hence induce apoptosis in Bcl-2 over-expressing cancers, the inventors designed a screening assay using Bcl-2 over-expressing cell lines. MDA-MB-231 cells expressing high or low Bcl-2 were used in an assay for screening library compounds. MTX was identified as one of the lead molecules in the screen that selectively induced apoptosis in MDA-MB-231 cells with increased expression of Bcl-2. MTX effects with respect to Bcl-2 expression were further characterized. The result of the library screening was reproduced in the subsequent validation assay for MTX (FIG. 9A), and this observation was extended to various cancer types. MTX reduced viability in MDA-MB-231/Bcl-2 cells significantly in comparison to the MDA-MB-231/Vector control cells (FIG. 9A). This Bcl-2 dependent effect of MTX was consistent in estrogen receptor (ER) positive MCF-7 cells over-expressing Bcl-2 (MCF-7/Bcl-2) (FIG. 9B) and was also observed in Jurkat T-cell lymphocytes over-expressing Bcl-2 (Jurkat/Bcl-2) (FIG. 9C).

Figure 9D:
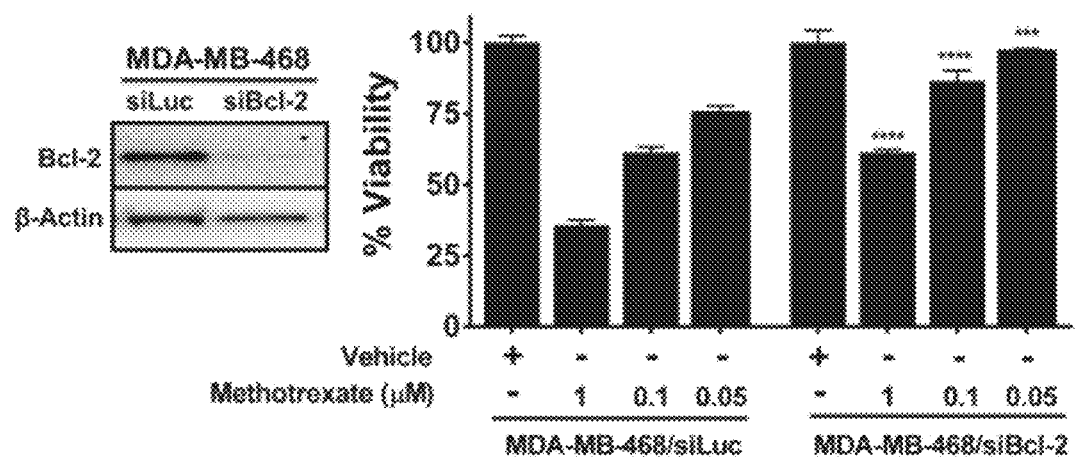
FIG. 9D depicts effect of methotrexate in certain cancer cell types. Left panel: Western blot for MDA-MB-468 cells after transient knockdown of Bcl-2. Right panel: Cells were exposed to various concentrations of Methotrexate as indicated for 24 h in a medium containing 10% FBS and viability was determined by cell titer glo assay.
Figure 9E:
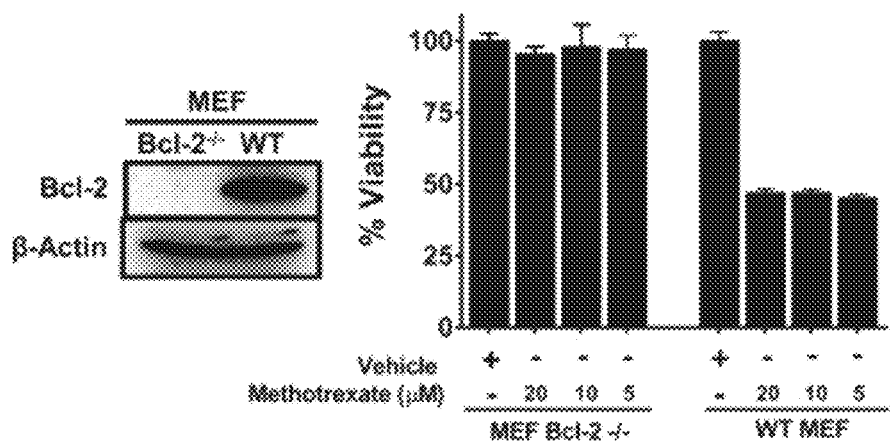
FIG. 9E depicts effect of methotrexate in certain cancer cell types. Left Panel: Bcl-2 levels in WT and Bcl-2–/– MEFs. Right panel: MEF cells were exposed to indicated concentrations of Methotrexate in medium containing 10% FBS and viability was determined by cell titer glo assay.
Figure 9F:
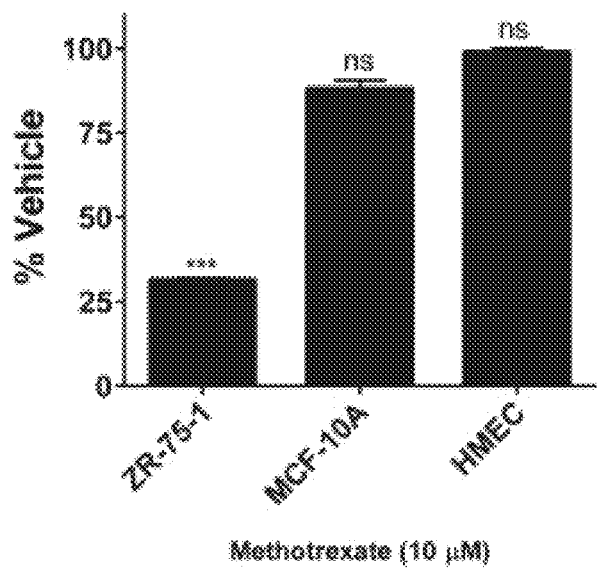
FIG. 9F depicts viability of methotrexate treated breast cancer cell line (ZR-75-1) in comparison to normal mammary epithelial cells (MCF-10A and HMECs).
Figure 9G:
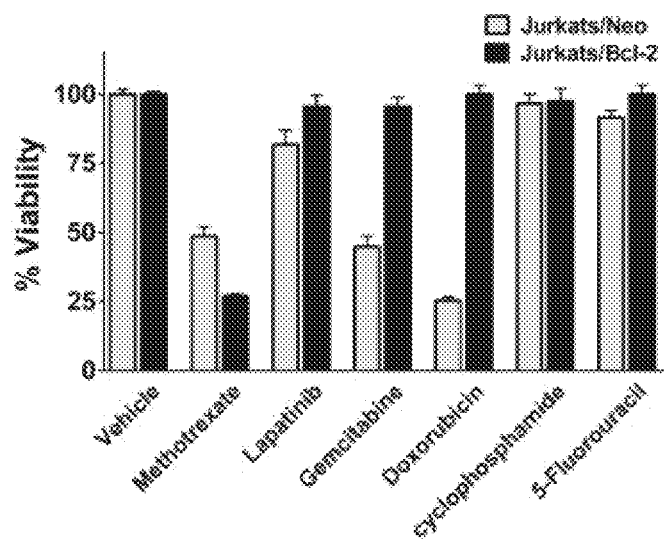
FIG. 9G depicts comparison of various cancer therapeutics in Jurkat cells with high and low expression of Bcl-2.
Figure 10A:
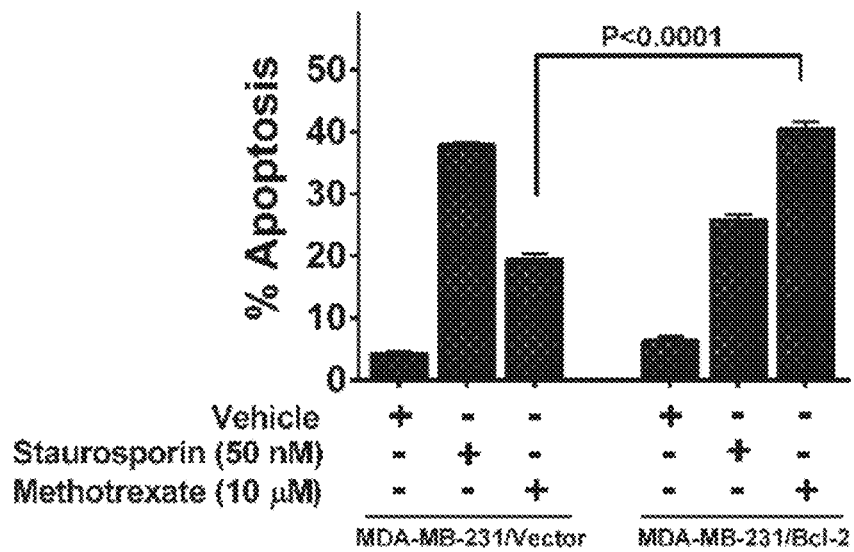
FIG. 10A demonstrates Bcl-2 dependent anti-tumorigenic effects of methotrexate. MDA-MB-231 cells with or without the Bcl-2 expression vector was treated with MTX at 10 µM for 24 h in a medium containing 10% FBS and apoptosis was determined by DAPI staining.
Figure 10B:
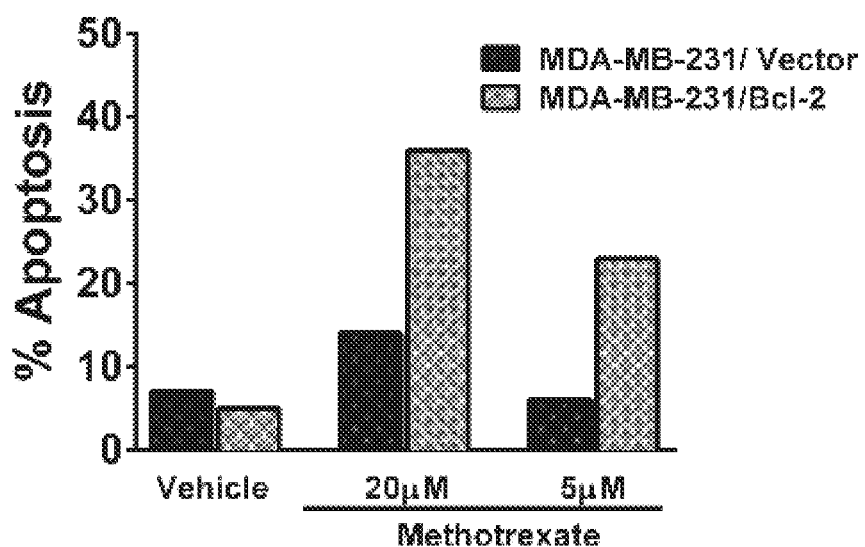
FIG. 10B shows MDA-MB-231 cells with or without the Bcl-2 expression vector was treated with MTX at the indicated concentrations for 24 h in a medium containing 10% FBS and apoptosis was determined by Annexin V staining.

Knockdown of Bcl-2 in MDA-MB-468 cells diminished the apoptotic effect of MTX (FIG. 9D). This Bcl-2 dependent induction of apoptosis by MTX was also seen in mouse embryonic fibroblast cells with or without Bcl-2 (FIG. 9E). Normal breast epithelial cells, MCF-10A, and human mammary epithelial cells (HMEC) were relatively unaffected when exposed to similar concentrations of MTX (FIG. 9F). In contrast, Bcl-2 expression protected Jurkat cells when exposed to chemotherapeutic drugs such as lapatinib, gemcitabine, doxorubicin, cyclophosphamide or 5-fluoro uracil (FIG. 9G). To determine the mechanism of the cell viability inhibition by MTX, MDA-MB-231 cells were subjected to nuclear condensation and fragmentation analysis (FIG. 10A). As expected, MTX treatment resulted in a higher apoptosis rate in the presence of the Bcl-2 protein. Furthermore, annexin-V staining, the assay that measures the exposure of phosphatidylserine, an early apoptotic event, showed increased apoptosis in the presence of the Bcl-2 protein (FIG. 10B). These results indicate that MTX inhibits cancer cell viability in Bcl-2 dependent manner by inducing apoptosis.

Figure 10C:
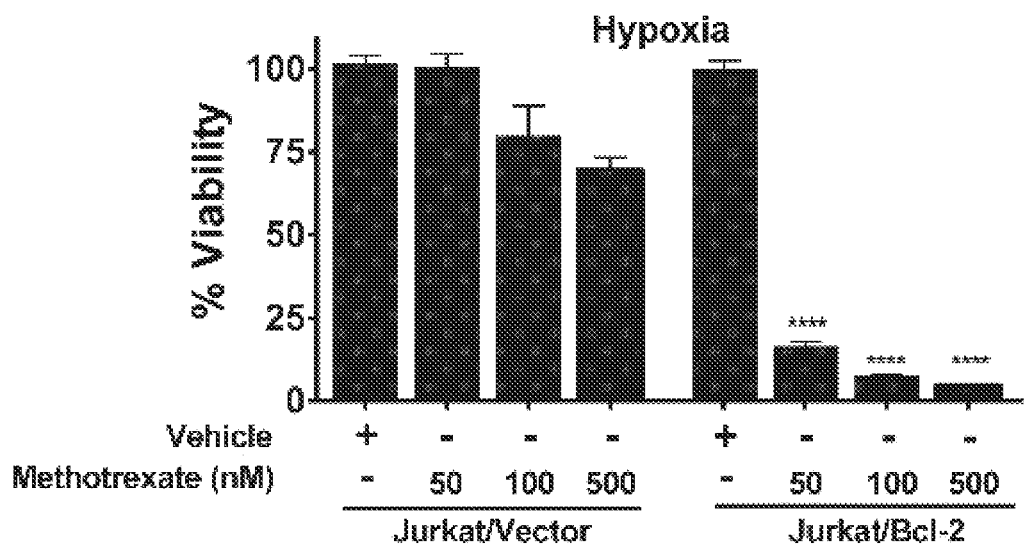
FIG. 10C shows Bcl-2 dependent effects of methotrexate on viability of jurkat cells with high and low expression of Bcl-2 under hypoxic conditions with 10% FBS for 24 h.
Figure 10D:
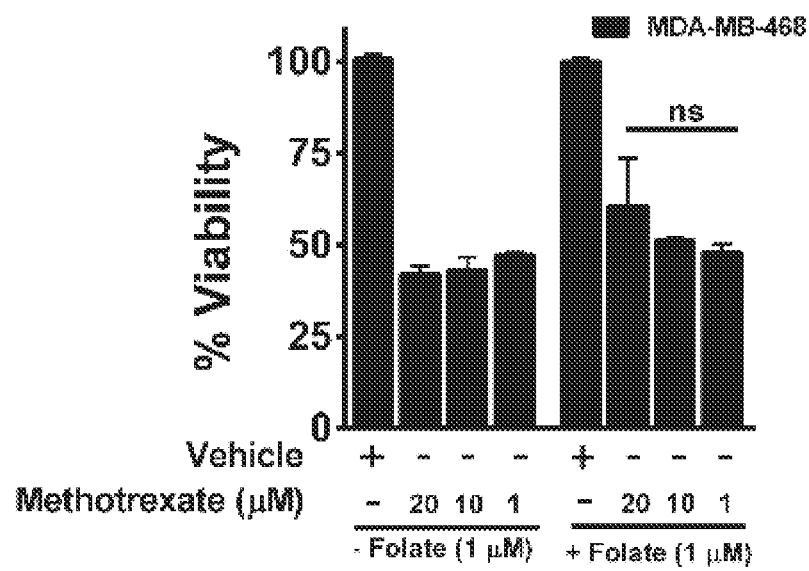
FIG. 10D demonstrates Folate rescue of jurkat cells treated with methotrexate. Methotrexate was treated at the indicated concentrations in jurkat cells with high and low expression of Bcl-2. At the same time of treatment with methotrexate folate at 1 µM was supplemented to determine the rescue effects of folate on methotrexate treated cells.

In certain embodiments, the small molecule Bcl-2 functional converters, for example, MTX and MTX analogs disclosed herein induce apoptosis under hypoxic conditions, as described below. It was tested if Bcl-2 dependent induction of apoptosis would also occur under hypoxic conditions. A significant reduction in viability of Jurkat/Bcl-2 cells compared to their Vector control (FIG. 10C) was seen. To rule out the influence of folate synthesis pathway, Jurkat cells were supplemented with 1 µM of folic acid and Bcl-2 dependent apoptosis was still observed (FIG. 10D).

Figure 10E:
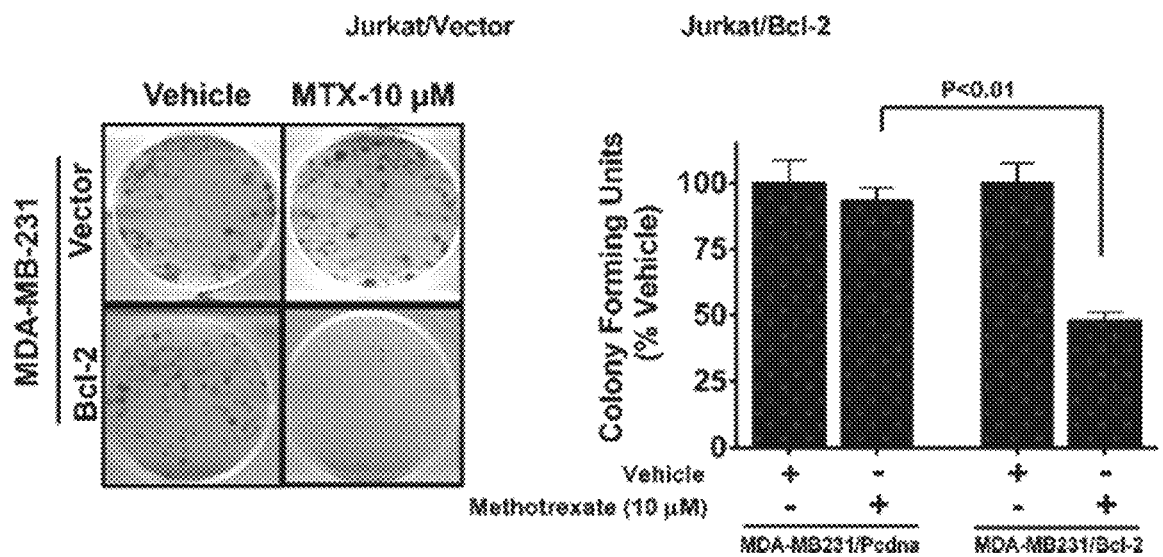
FIG. 10E shows effect of MTX on clonogenic survival of MDA-MB-231/Vector and MDA-MB-231/Bcl-2 cells was determined using 10 µM concentration of MTX for 24 h.
Figure 10F:
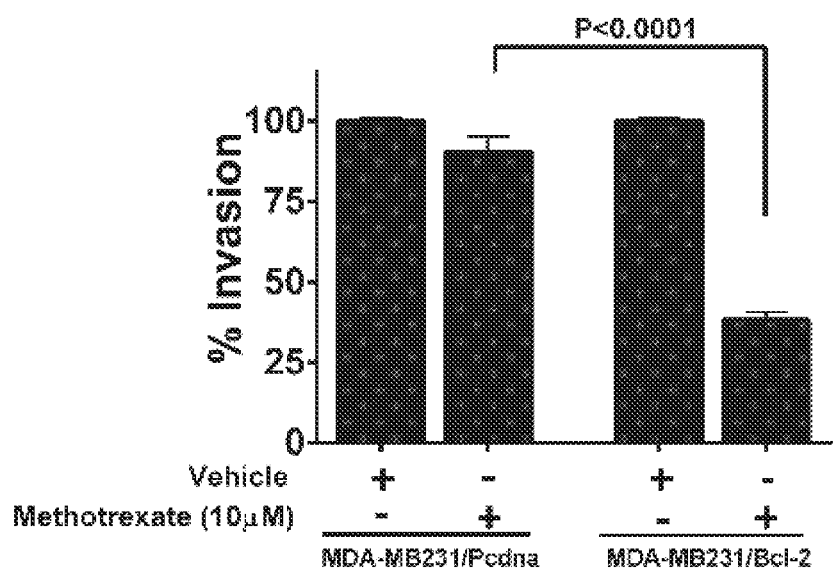
FIG. 10F is MDA-MB231 cells with or without Bcl-2 expression vector were treated with 10 µM MTX or vehicle in a matrigel invasion chamber for 16 h and the membrane was then fixed, stained and number of cells invaded counted.

The effect of MTX on the clonogenic survival of MDA-MB-231 cells was determined. Following treatment with 10 µM MTX, MDA-MB-231/Bcl-2 cells formed significantly fewer colonies by 60%, compared to vector controls (FIG. 10E). This led the inventors to ask if there is an effect on the invasive potency of the MDA-MB-231/Bcl-2 cells. In a transwell matrigel assay, treatment with 10 µM MTX inhibited the invasive potential of Bcl-2 over-expressing cells, compared to their vector controls (FIG. 10F). These data suggest that MTX inhibits cell viability and cell invasion in the presence of Bcl-2 protein.

Methotrexate Interaction with Bcl-2

Figure 11A:
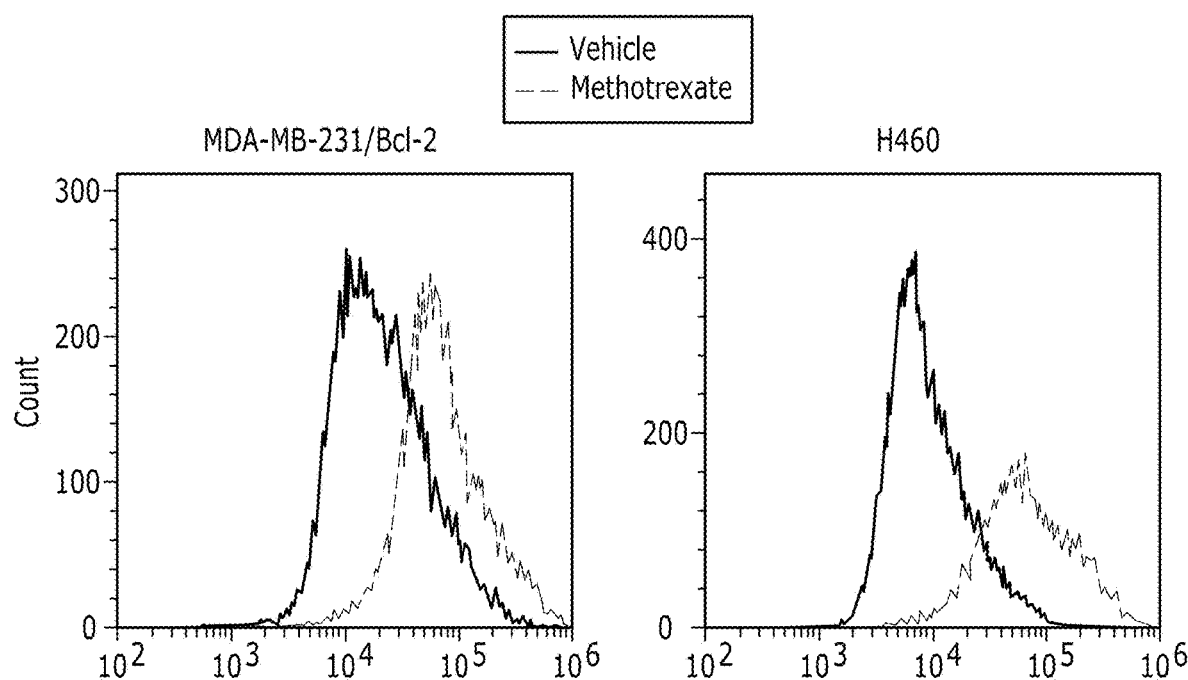
FIG. 11A depicts Interaction of methotrexate with Bcl-2. MDA-MB231/Bcl-2 cells and H460 cells were exposed to MTX at 10 µM concentration for 24 h in a medium containing 10% serum. Change in Bcl-2 conformation was determined using Bcl-2 BH3 only anti-body followed by flow cytometric analysis.
Figure 11B:
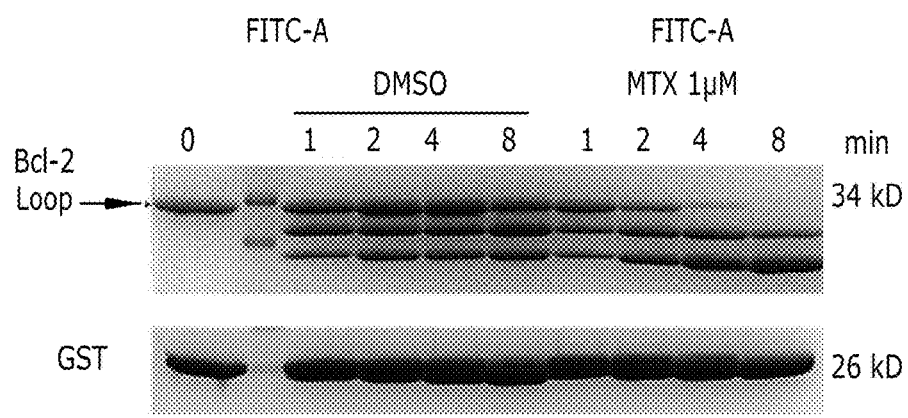
FIG. 11B depicts proteolysis of Bcl-2 loop domain in the presence of methotrexate. GST tagged BCl-2 loop domain was incubated with 1 µM methotrexate at the indicated times to determine if methotrexate interaction with loop domain has an effect on the proteolysis pattern upon co incubation with trypsin.
Figure 11C:
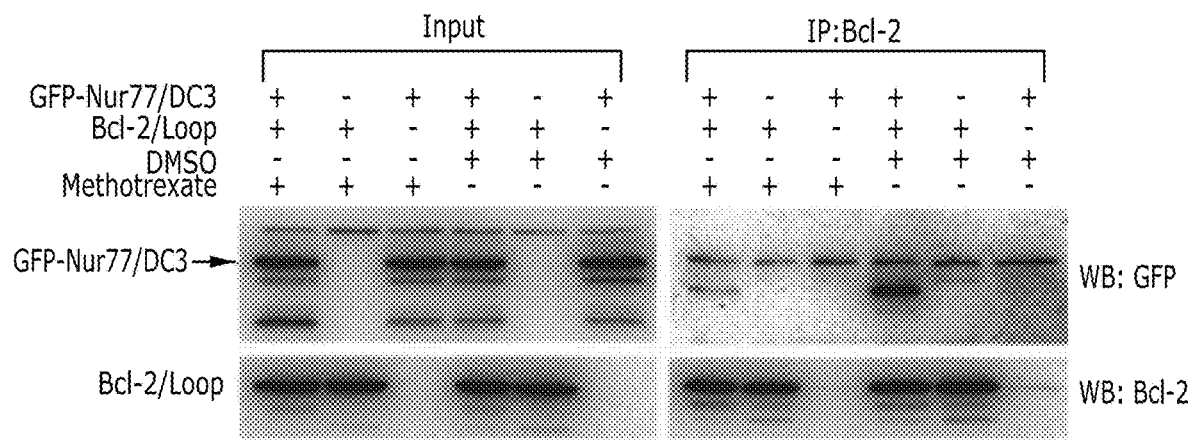
FIG. 11C demonstrates that methotrexate competes with Nur-77 for interaction with BCl-2 loop domain. Methotrexate reduced the interaction of Nur-77 with BCl-2 domain upon co-incubation indicating methotrexate interacts with the same region of loop domain as does Nur-77.

To evaluate whether the apoptotic action of MTX was due to conformational change in the Bcl-2 protein, converting its function to a pro-apoptotic one, the inventors used a Bcl-2 BH3 domain antibody to recognize the change in conformation of Bcl-2 between vehicle and MTX treated MDA-MB-231/Bcl-2 cells (FIG. 11A). When there is a conformational change in Bcl-2 protein, the BH3 domain is exposed and is detected by the Bcl-2 BH3 domain antibody. Consistent with the hypothesis, there was a considerable shift in the staining of MTX treated cells indicating change in the Bcl-2 conformation (FIG. 11A). This phenomenon was also observed in H460 cells treated with MTX under similar conditions (FIG. 11A). Thus, the Bcl-2 dependent induction of apoptosis by MTX is due to change in conformation of the Bcl-2 protein. To further characterize the interaction of MTX with the Bcl-2 protein, the inventors set out to evaluate if MTX interaction has an effect on limited proteolysis of the Bcl-2 loop domain. The inventors observed a differential proteolysis pattern in the presence of MTX (FIG. 11B). In addition, in a co-immunoprecipitation assay, the competition between MTX and Nur77 in interacting with the Bcl-2 protein could be seen (FIG. 11C). These data indicate that MTX directly binds to the Bcl-2 protein on the loop domain thereby unmasking or exposing the pro-apoptotic BH3 domain to induce apoptosis.

Methotrexate Induces Mitochondrial Intrinsic Death Pathway

Figure 12A:
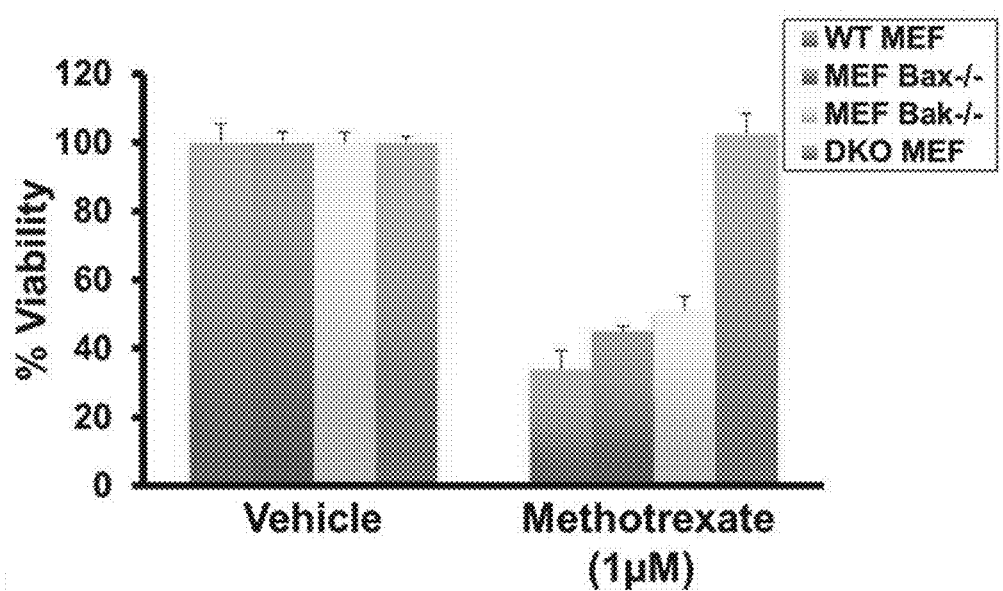
FIG. 12A demonstrates methotrexate induced mitochondrial intrinsic death pathway. WT MEF, BAX$^{-/-}$ MEF, BAK$^{-/-}$ MEF and Bax$^{-/-}$ Bak$^{-/-}$ MEF cells were treated with MTX at 1 µM concentration for 24 h in 10% serum conditions. Viability was assessed using the Glo assay. MTX treatments were normalized to 100% of Vehicle.
Figure 12B:
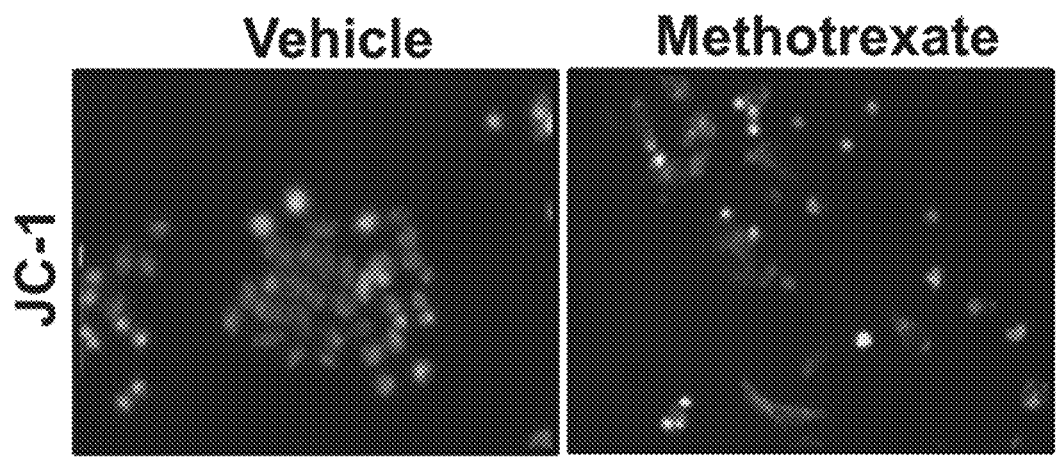
FIG. 12B demonstrates methotrexate induced mitochondrial intrinsic death pathway. JC-1 was used to stain live cells undergoing treatment with MTX at 10 µM for 16 h and images taken with FITC and Rhodamine filters were overlayed. Cells stained orange have intact mitochondrial outer membrane and the ones turning green have compromised outer membrane indicating loss of membrane potential.

In order to further probe the mechanism of MTX induced cell death, MEF cells with or without Bax or Bak were treated with MTX and their viability was determined. Wild type MEF cells were most effected by MTX, with only about 30% being viable. Bax$^{-/-}$ MEF and Bak$^{-/-}$ MEF also had reduced viability to about 40%. However, viability of Bax$^{-/-}$ Bak$^{-/-}$ MEF (DKO) cells was not effected in comparison to the cells having Bax or Bak (FIG. 12A), indicating Bax or Bak is required for MTX to induce cell death. MTX treated H460 cells showed decrease in their mitochondrial membrane potential when stained with JC-1 dye, demonstrating collapse of mitochondrial outer membrane permeabilization (MOMP) (FIG. 12B). Thus, MTX induced apoptosis was not only dependent on the Bcl-2 protein, but also required the Bax or Bak expression, indicating that MTX induced apoptosis may follow the mitochondrial intrinsic pathway.

Efficacy of Methotrexate in an In Vivo Model

The MDA-MB-231/Bcl2 cell line was used in a xenograft study using NOD SCID mice to test MTX effect using an in vivo model. MTX treated mice had significant inhibition of tumor growth by 15 days of treatment with 100 mg/kg dose of MTX, compared to the vehicle treated mice (FIG. 13A). At the end of the study, immunohistochemistry was performed on the tumor sections from these mice. Apoptosis was detected using TUNEL staining (FIG. 13B), and a change in Bcl-2 conformation was detected by the Bcl2 BH3-specific antibody (FIG. 13C). To further validate the mitochondrial intrinsic cell death pathway, activated Bax was also detected (FIG. 13D) along with cleaved caspase-3 (FIG. 13E). Thus, MTX caused a change in conformation of Bcl-2 and induced apoptosis in Bcl-2 over-expressing tumors in an in vivo model. This change in conformation of Bcl-2 resulted in activation of Bax and cleaved caspase-3, which are indicative of intrinsic apoptotic pathway.

Discovery of Methotrexate Analogs that Induce Bcl-2-Dependent Cell Death.

In certain embodiments, agent of the methods for inducing apoptosis in a cell or the methods of cancer treatment is a methotrexate (MTX) or MTX analog, for example, a compound of Table 6.

A number of methotrexate analogs were tested in MDA-MB-231 cells with low or high expression of Bcl-2. The cells were treated with different concentrations of the analogs for 48 or 72 hours. This led to the identification of compounds that induced apoptosis in Bcl-2-dependent manner with higher affinity than the parental compound Table 6 lists exemplary MTX analogs that can be used in the methods disclosed herein. Table 7 shows the minimal effective concentrations that induced Bcl-2-dependent reduction in cell viability in Bcl-2 low and high expressing Jurkat lymphoma cells that were plated and treated for 72 hours with various concentrations of methotrexate analogs.

TABLE 6

Structures of methotrexate analogs that were tested for Bcl-2 dependent apoptosis.

| Compound | Structure |
|---|---|
| MTX | *structure* |
| 1 | *structure* |
| 2 | *structure* |
| 3 | *structure* |
| 4 | *structure* |

TABLE 6-continued
Structures of methotrexate analogs that were tested for Bcl-2 dependent apoptosis.
| Compound | Structure |
|---|---|
| 5 | 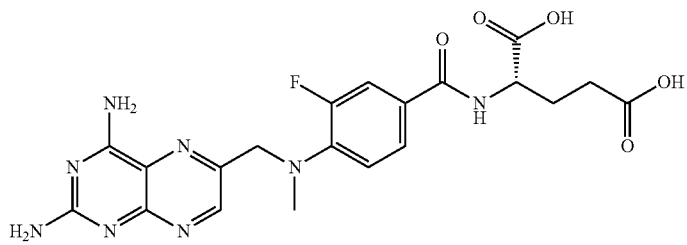 [SMILES: CN(Cc1cnc2nc(N)nc(N)c2n1)c1ccc(C(=O)N[C@@H](CCC(=O)O)C(=O)O)cc1F] |
| 6 | 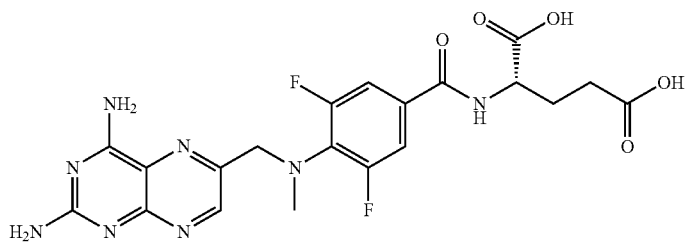 [SMILES: CN(Cc1cnc2nc(N)nc(N)c2n1)c1c(F)cc(C(=O)N[C@@H](CCC(=O)O)C(=O)O)cc1F] |
| 7 | 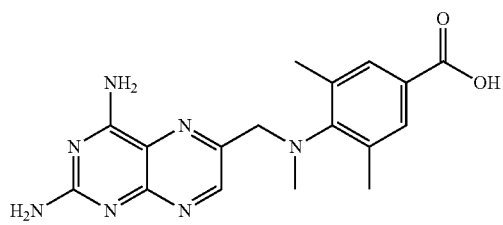 [SMILES: Cc1cc(C(=O)O)cc(C)c1N(C)Cc1cnc2nc(N)nc(N)c2n1] |
| 8 | 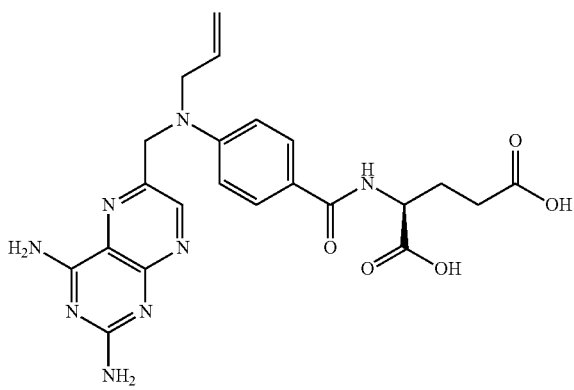 [SMILES: C=CCN(Cc1cnc2nc(N)nc(N)c2n1)c1ccc(C(=O)N[C@@H](CCC(=O)O)C(=O)O)cc1] |
| 9 | 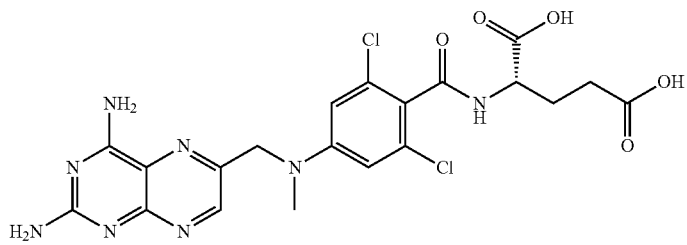 [SMILES: CN(Cc1cnc2nc(N)nc(N)c2n1)c1cc(Cl)c(C(=O)N[C@@H](CCC(=O)O)C(=O)O)c(Cl)c1] |

TABLE 6-continued

Structures of methotrexate analogs that were tested for Bcl-2 dependent apoptosis.

| Compound | Structure |
|---|---|
| 10 | 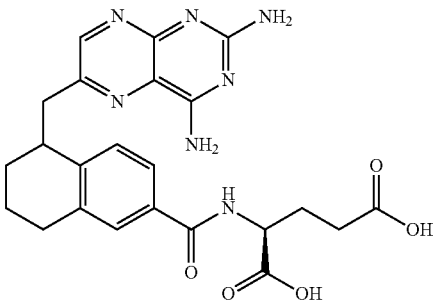 [SMILES: Nc1nc(N)c2nc(CC3CCCc4cc(C(=O)N[C@@H](CCC(=O)O)C(=O)O)ccc43)cnc2n1] |
| 11 | 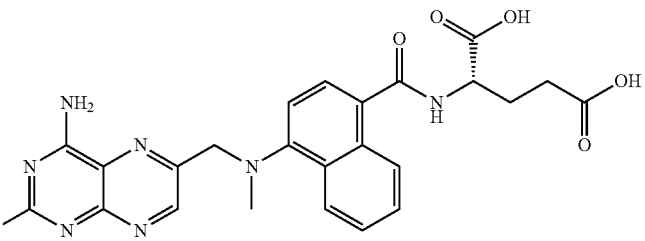 |
| 12 | 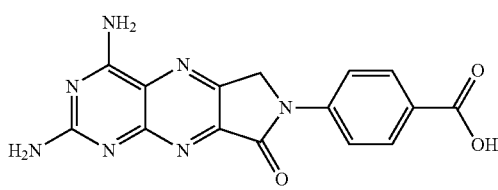 [SMILES: Nc1nc(N)c2nc3c(nc2n1)C(=O)N(c1ccc(C(=O)O)cc1)C3] |

TABLE 7

Minimal effective concentrations of exemplary MTX analogs that induced Bcl-2-dependent reduction in cell viability ("n/d" means no reduction was detected at concentrations tested).

| Compound | MW | Bcl-2 dependent effects in Jurkat Lymphoma cells | Lowest effective dose (uM) |
|---|---|---|---|
| MTX |  | Yes | 0.01 |
| 1 | 440 | Yes | 0.01 |
| 2 | 523 | Yes | 0.001 |
| 3 | 426 | Yes | 10.0 |
| 4 | 455 | No | n/d |
| 5 | 472 | Yes | 0.01 |
| 6 | 490 | Yes | 0.01 |
| 7 | 353 | No | n/d |
| 8 | 480 | Yes | 0.01 |
| 9 | 523 | Yes | 1.0 |
| 10 | 480 | Yes | 0.1 |
| 11 | 505 | Yes | 0.001 |
| 12 | 337 | No | n/d |

It was found that methotrexate directly interacts with Bcl-2. This interaction results in a change in the phenotype of Bcl-2 from anti-apoptotic to pro-apoptotic. This functional conversion of Bcl-2 resulted in induction of apoptosis in cancer cells expressing Bcl-2. There was minimal or no cell death in cancer cells expressing either low Bcl-2 or in Bcl-2 knockout cells. Also, MTX spared normal breast epithelial cells of both mouse and human origin. Bcl-2 dependence was observed in triple negative breast cancer (TNBCs) cells, MDA-MB-231, over-expressing Bcl-2. It is evident that TNBCs are challenging to treat because of the absence of growth hormones and other reliable molecular targets that can distinguish them from normal tissue. In another TNBC cell line, MDA-MB-468, the inventors transiently knocked down Bcl-2 and found that the apoptotic effect of MTX diminished. The inventors showed this phenomenon in estrogen receptor positive breast cancer cells, MCF-7, as well as in Jurkat T-cell lymphocytes, suggesting that for the apoptotic inducing action of MTX, presence of Bcl-2 protein is sufficient, independent of the cancer cell type.

The finding that MTX binds to the loop domain of Bcl-2, inducing change in its conformation and reversal of its function, will have implications in the prognosis and treatment of diseases where MTX is currently used. This also lays the foundation for the study of Bcl-2 protein in those diseases. Many drugs under development fail to work under hypoxic conditions. When MTX was tested under hypoxic conditions it was not only effective in inducing cell death but it was also dependent on Bcl-2. Bcl-2 over-expression results in more aggressive tumors and the invasive capacity of tumor cells increases, resulting in metastasis. MTX treatment could reduce the invasiveness of Bcl-2 over-expressing TNBC cells, rendering its use in metastatic and aggressive cancers. The use of MTX in Bcl-2 positive tumors is of immense utility as the side effects caused by inhibition of its classical folate synthesis pathway targets are alleviated by supplementing with folate or leucovorin. Even at saturating concentrations of 1 μM folate, MTX induced Bcl-2 dependent apoptosis. The inventors tested other chemotherapeutic drugs for breast cancer and only MTX was found to induce Bcl-2 dependent apoptosis. The loop domain of Bcl-2 acts as a regulator of its activity. The function of Bcl-2 is reversed when the loop is phosphorylated, cleaved by caspases or interacting with other proteins like p53 and Nur77. Inventors found that MTX interacts with the loop domain of Bcl-2 exposing its BH3 domain. This change in conformation of Bcl-2 by MTX was seen both in vitro and in vivo. The inventors also verified this interaction by showing the alteration in proteolysis of the loop domain of Bcl-2 in the presence of MTX. MTX could also compete with NuBCP-9 in its affinity to interact with the loop domain of Bcl-2. This raises questions of whether MTX interacts with other proteins that have unstructured loop domain similar to Bcl-2. Investigation on these lines could potentially unravel other pathways or diseases where MTX could be used. MTX induced an intrinsic mitochondrial apoptotic pathway by functional conversion of Bcl-2. Bax activation upon treatment with MTX was seen both in vitro and in vivo. MTX demonstrated potent anti-tumor activity in an orthotopic breast cancer model. The Bcl-2 over-expressing MDA-MB-231 cells were used in the generation of the tumors in the mammary fat pad and, as expected, the arising tumors were quite aggressive. This in vivo experiment only serves as a proof of concept model since the half-life of MTX is different in mice (0.5 h) and humans (7-10 h).

Current small molecule therapeutics under development target Bcl-2 by inhibiting its pro-survival function. This is accomplished by binding to its hydrophobic grove thus inhibiting other pro-apoptotic proteins from binding to it. Of the numerous small molecules under development, ABT-199 stands out among them. However, ABT-199 has hit roadblocks due to development of resistance by multiple mechanisms. There have been mutations in the Bcl-2 binding region of ABT-199 rendering it ineffective. Additionally, over-expression of other Bcl-2 family proteins like Mel-1 has led to resistance. Here the inventors show MTX targets Bcl-2 different from the Bcl-2 inhibitors. MTX doesn't inhibit Bcl-2 but actually converts it into a pro-death protein. MTX has been traditionally used as a chemotherapeutic along with cyclophosphamide and 5-fluorouracil. A clinical study showed this cocktail (CMF) had better outcome in Bcl-2 positive cancers as opposed to Bcl-2 negative cancers. Herein, the inventors show that MTX alone is effective in inducing apoptosis in Bcl-2 positive cancers. Fluorouracil was shown to reduce Bcl-2 expression in gastric cancer cells and hence should be used in combination with other drugs and not MTX. In another clinical study, Bcl-2 positive breast cancer patients had better responses to MTX. There was no clear-cut correlation between Bcl-2 expression and chemotherapy response in patients likely due to use of MTX in the chemotherapy cocktail (Cyclophosphamide-MTX-Fluorouracil). This study may clear that doubt and warrant the use of MTX as a targeted therapeutic. The nature of MTX binding to the loop domain of Bcl-2 is discussed below.

In certain embodiments, the methods for inducing apoptosis or the methods for treatment of cancer disclosed are used in combination with other cancer therapy, for example, radiation therapy. There are numerous occasions where Bcl-2 is upregulated due to radiation therapy, chemotherapy, or prolonged use of other targeted cancer drugs. MTX can be used in combination with these treatments to increase their efficacy. Since MTX is effectively tested in low doses for long term use in certain indications, it could be tested for cancer treatment to avoid relapse. MTX can be a cost effective targeted therapy ready to be used in clinics.

In some embodiments, the methods for treatment of cancer disclosed herein further comprising administering a folate or leucovorin. It is known in the art that the side effects of MTX dosing are well studied and can be easily overcome by supplementing with leucovorin or folic acid. MTX can be used at a low dose and yet its bioavailability could be as high as 70%. Polymorphisms in the RCF1 gene could be screened in patients to predict therapeutic response. There are also new formulations of MTX for improved bioavailability and convenience of administration.

In conclusion, the inventors demonstrated that MTX, which has been used for over 5 decades as a drug, interacts with Bcl-2, changing it into a pro-apoptotic protein to induce apoptosis. Thus, the studies disclosed herein discovered a new mechanism of action of MTX and identified it as a Bcl-2 targeted therapeutic.

3. Small Molecule Bcl-2 Functional Converter BFC1108 for Breast Cancer Therapy In certain embodiments, the agent of the methods for inducing apoptosis in a cell or the methods of cancer treatment is compound BFC 1108 or its structural analog, for example, a compound of Formula (III).

To screen for small molecules that can specifically target and induce apoptosis in Bcl-2 expressing cancer cells, a viability assay was employed. MDA-MB-231 cells stably expressing high levels of Bcl-2 (MDA-MB-231/Bcl-2) were used along with cell with low expression of Bcl-2, e.g., its vector controls (MDA-MB-231/Vectors). A DIVERset™ library from ChemBridge was used to treat these cells in a 24 h viability assay. Compounds were shortlisted and retested based on Bcl-2 dependent effect on viability.

The lead compound BFC1108 (FIG. 15A) had dose dependent reduction in viability of Bcl-2-high expressing cells (MDA-MB-231/Bcl-2), compared to their vector controls (FIG. 15B). This phenomenon is confirmed in other cancer cell types. It was found that MCF-7 cells with high-Bcl-2 expression are more sensitive to BFC1108 compared to their Bcl-2 low-expressing control cells (FIG. 15C). In Jurkat T-Cell Lymphocytes with high-Bcl-2 expression, reduction in viability was seen compared to their Bcl-2 low-expressing control cells (FIG. 15D). This effect of BFC1108 was further evaluated if it was abrogated in the absence of Bcl-2. For this, transient knockdown of Bcl-2 expression in MDA-MB-468 cells was employed. In siRNA-transfected control cells the inventors discovered reduced viability of cells in a dose-dependent manner. When Bcl-2 was knocked down, the cells were rescued from the effects of BFC1108 (FIG. 15E). Thus BFC1108 specifically targets Bcl-2. Next, BFC1108 was evaluated if it had any cytotoxic effects in normal mammary epithelial cells. For this, similar concentrations of BFC1108 to those used in cancer cells were tested on MCF-10A control epithelial cells to evaluate their viability. No effect on the viability of MCF-10A cells was seen when treated under similar conditions used for cancer cells (FIG. 15F). BFC1108 was shown to reduce viability in a variety of cancer cell types including LNCaP, HepG2, H460, A375 and U251, suggesting BFC1108 is effective in multiple types of cancer cells (FIG. 15F).

Anti-Tumorigenic Effects of BFC1108

The effects of BFC1108 on clonogenic survival of MDA-MB-231 cells were determined. When exposed to BFC1108, MDA-MB-231/Bcl-2 cells formed fewer colonies compared to their vector controls (FIG. 16A). When MDA-MB-231/Bcl-2 cells were treated with 10 µM BFC1108, there was a 50% reduction in its colony forming ability compared to its vehicle controls. This effect was not seen in low Bcl-2 expressing 231/Vector control cells. In addition, colony forming ability of mouse embryonic fibroblasts (MEFs) was also evaluated. Wild type (WT) MEFs had fewer colonies during exposure to BFC1108 at a 10 µM concentration compared to their vehicle controls (FIG. 16B). This effect was absent in MEF Bcl-2−/− cells. Next, it was confirmed if the effect of BFC1108 on cell viability was due to apoptosis. For this, MDA-MB-231/Bcl-2 along with their vector controls were exposed to BFC1108 at 10 µM for 48 h and cells were stained with annexin V to detect early stages of apoptosis. As in the case of viability assays, increased apoptosis in MDA-MB-231/Bcl-2 cells was observed, indicating that BFC1108 induces apoptosis in a Bcl-2 dependent manner (FIG. 16C).

BFC1108 Induces Conformational Change in Bcl-2

When Bcl-2 interacts with orphan receptor Nur77/TR3 or with p53, its conformation is changed. This type of interaction causes exposure of its own BH3 domain, leading to reversal of its function from anti-apoptotic to pro-apoptotic. This changed conformation of Bcl-2 can be detected by a Bcl-2-BH3 domain antibody. When MDA-MB-231/Bcl-2 cells were treated with BFC1108 and analyzed using flow cytometry, changed conformation of Bcl-2 was detected (FIG. 17A). To further investigate the interaction of BFC1108 with the loop domain of Bcl-2, it was evaluated if the presence of BFC1108 would impact the proteolysis of the Bcl-2 loop domain. If there is direct interaction of BFC1108 with Bcl-2 loop domain the proteolysis of Bcl-2 loop domain is expected to be different. Indeed, increased proteolysis of Bcl-2 loop domain was noticeable by 4 min time point, compared to vehicle, suggesting the direct interaction of Bcl-2 loop and BFC1108 (FIG. 17B).

BFC1108 Induces Intrinsic Mitochondrial Death Pathway

To further validate that the changed conformation of Bcl-2 initiates the intrinsic apoptotic pathway, the requirement of Bax and/or Bak for the apoptotic action of BFC1108 was tested. In MEF cells treated with BFC1108, the inventors observed no effect on viability in DKO MEFs, whereas Bax-1-MEF and Bak-1-MEF have diminished viability, just as WT MEFs are susceptible to BFC1108 (FIG. 17C). Thus Bax and/or Bak are required for the Bcl-2 dependent apoptotic action of BFC1108. Next, the mitochondrial permeability was tested as the intrinsic mitochondrial pathway is activated by the action of BFC1108. BFC1108 treated H460 cells, stained with JC-1 dye, showed decreased mitochondrial membrane potential indicating collapse of mitochondrial outer membrane (FIG. 17D). Thus, BFC1108 induced change in Bcl-2 conformation leads to intrinsic mitochondrial death pathway.

BFC1108 Suppresses Bcl-2 Over-Expressing Breast Cancer In Vivo

To test the potency of BFC1108 in vivo, orthotopic breast cancer xenografts derived from MDA-MB-231/Bcl-2 cells were treated with BFC1108 for 4 weeks via intraperitoneal route. BFC1108 significantly reduced the growth of a xenograft tumor (FIG. 18A). To ascertain if this reduction in tumor growth was due to tumor cells undergoing apoptosis and not growth inhibition, the inventors determined apoptosis in these tumor sections by immunohistochemistry for TUNEL stain and active-caspase-3. TUNEL-positive cells (FIG. 18B) and active caspase-3 cells (FIG. 18C) could be detected, confirming the inductions of apoptosis by BFC1108 in vivo. The inventors further probed these tumor sections to detect the presence of changed conformation of Bcl-2. In the tumor sections treated with BFC1108, there was increased fluorescence, indicating presence of Bcl-2 with changed conformation, compared to their vehicle controls (FIG. 18D). To link changed conformation to activation of Bax, the inventors probed the tumor section with activated Bax antibody and found Bax activation in BFC1108 treated sections (FIG. 18E). Thus the mechanism of functional conversion of Bcl-2 leading to activation of intrinsic mitochondrial death pathway was validated in vivo.

Efficacy of BFC1108 in a Lung Metastatic Model

Next, the efficacy of BFC1108 in suppressing breast cancer lung metastasis was evaluated. LMD231 cells are lung metastatic cells derived from triple negative breast cancer tumors of MDA-MB-231 cells. LMD231 cells are thus pre-programmed to form only lung metastatic tumors. LMD231 cells were engineered to stably express luciferase to aid in the detection of metastasis. LMD231-Luc cells, when injected through the tail vein, formed lung metastasis in 2 weeks. Doses of 100 mg/kg BFC1108 were given, 4 times a week by intraperitoneal injections. By the end of 7 weeks, BFC1108 suppressed the growth of lung metastasis (FIGS. 19A and 19B). On IHC staining an analysis of the lung tissue for Ki-67, only vehicle treated animals showed Ki-67 positivity, indicating presence of actively proliferating tumor cells.

In this study, a class of small molecule Bcl-2 functional converter (BFC1108 and its structural analogs) was found that can suppress primary and metastatic breast cancers in mouse xenograft models. This study provides a proof of concept for targeting Bcl-2, using small molecules that do not inhibit its function but rather alters it to therapeutic advantage.

It was demonstrated herein that BFC1108 induces apoptosis in cancer cells as long as they express Bcl-2. This induction of apoptosis is due to the interaction of BFC1108 with the loop domain of Bcl-2. This interaction resulted in exposure of the BH3 domain of Bcl-2, making it a pro-apoptotic protein. BFC1108 is also dependent on the presence of Bax and/or Bak for inducing the mitochondrial cell death pathway. More importantly, BFC1108 could suppress breast cancer in a mouse model of Bcl-2 high-expression. Where most cancer therapeutics would fail, due to Bcl-2 over-expression, BFC1108 was potent in significantly inducing apoptosis. BFC1108 also suppressed the growth of breast cancer lung metastasis, indicating its utility in comprehensively treating cancers prone to metastasis or metastatic cancer dependent on Bcl-2.

4. Small Molecule Bcl-2 Functional Converters for Breast Cancer Lung Metastasis Screening of Small Molecules Targeting Bcl-2

A library consisting of structurally diverse small molecules was used to screen for small molecules that induce death in cells with higher Bcl-2 expression. A viability assay was employed to screen the library compounds in triple negative breast cancer cell line, MDA-MB-231, with either high or low expression levels of Bcl-2. The lead compound BFC1103 (FIG. 20A) had a Bcl-2 dependent reduction in viability of MDA-MB-231 cells. MDA-MB-231 cells with high levels of Bcl-2 showed increased apoptosis upon treatment with BFC1103 (FIG. 20B). To demonstrate Bcl-2 dependent effects of BFC1103 on other cell types, the inventors tested the effect of BFC1103 in MCF-7 cells with high and low expression of Bcl-2. BFC1103 treatment reduced the viability of MCF-7 cells with high Bcl-2 levels, compared to Bcl-2 low expressing control cells (FIG. 20B). Similarly, BFC1103 reduced the viability of Jurkat human T cell leukemia cells with high Bcl-2 expression, compared to control cells (FIG. 20B). BFC1103 also reduced viability of MDA-MB-468 triple negative cells. Suppression of Bcl-2 expression reduced the effect of BFC1103 (FIG. 20C), suggesting BFC1103 requires Bcl-2 expression to induce cell death. The effects of BFC1103 in normal mammary epithelial cells and multiple cancer cell types were compared. BFC1103 had minimal effect on normal mammary epithelial cells (MCF-10A) but reduced the viability of a host of cancer cell types including breast cancer ZR-75-1, non-small cell lung cancer H460, melanoma A375, liver cancer HepG2, and prostate cancer LNCaP cells (FIG. 20D).

It was further tested if this Bcl-2 dependent induction of apoptosis by BFC1103 would occur under hypoxic conditions. A significant reduction in viability of MDA-MB-231 with increased Bcl-2 expression compared to the control cells was seen (FIG. 21B). The effect of BFC1103 on long term clonogenic survival of MDA-MB-231 cells was determined. MDA-MB-231 cells over-expressing Bcl-2 treated with 10 µM BFC1103, formed significantly fewer colonies, compared to control cells (FIG. 21C).

BFC1103 Interaction with Bcl-2

The inventors determined if the Bcl-2 dependent apoptotic induced by BFC1103 is due to change in conformation of Bcl-2, converting its function from an anti-apoptotic to a pro-apoptotic protein. A Bcl-2 BH3 domain antibody that specifically recognizes Bcl-2 with changed conformation was employed. Following treatment with BFC1103, changed conformation of Bcl-2 of was detected in MDA-MB-231/Bcl-2 cells (FIG. 22A). The inventors previously demonstrated that the loop domain in Bcl-2 plays an important role in conformational changes leading to the exposure of BH3 domain in Bcl-2. To test if BFC1103 interacts with the loop domain of Bcl-2, a limited proteolysis of loop domain of Bcl-2 with or without BFC1103 was conducted. BFC1103 delayed the proteolysis of the loop domain of Bcl-2 suggesting its affinity towards the loop domain (FIG. 22B).

BFC1103 Induces Mitochondrial Intrinsic Death Pathway

To determine if BFC1103 induced cell death is dependent on the presence of Bax or Bak, mouse embryonic fibroblast cells (MEFs) with or without the expression of Bax or Bak were used. Upon exposure to BFC1103, wild type MEF cells, MEF cells without Bax or Bak expression had significant reduction in their viability compared to the double knockout (DKO) MEFs (FIG. 23A). Thus, the apoptosis induced by BFC1103 requires the expression of Bax or Bak. BFC1103 treated H460 cells showed a decrease in their mitochondrial outer membrane potential when stained with JC-1 dye, demonstrating collapse of the mitochondrial outer membrane (FIG. 23B). Thus, BFC1103 induces a mitochondrial intrinsic apoptotic pathway.

Efficacy of BFC1103 in a Breast Cancer Lung Metastatic Model

The inventors next determined the efficacy of BFC1103 in suppressing breast cancer lung metastasis. LMD231 cells are metastatic cells derived from lung metastasis of MDA-MB-231 cells. LMD231 cells are pre-programmed to form only lung metastasis when introduced in mice. LMD231 cells were engineered to stably express luciferase (LMD231-Luc) for easy detection in nude mice. Approximately 200,000 LMD231-Luc cells were injected into the tail vein of 5 week old nude mice and lung metastasis could be detected in 2 weeks. BFC1103 was dosed at 50 mg/kg by the intraperitoneal route for 6 days per week. By the end of 7 weeks, BFC1103 significantly suppressed the growth of lung metastasis (FIG. 24A). Immunohistochemical analysis of lung tissue by H&E revealed potent suppression of tumor growth by BFC1103 when compared with vehicle treated mice (FIG. 24B). Further, lung tissues from vehicle treated mice had a significantly higher number of proliferating cells, as measured by Ki67 staining, than the BFC1103 treated mice (FIG. 24C). Thus, BFC1103 was effective in reducing breast cancer lung metastasis.

Thus, a new class of small molecule Bcl-2 functional converters, compound BFC1103 and its structural analogs, that can suppress breast cancer lung metastases was found. Current cancer therapies that target the Bcl-2 protein inhibit the anti-apoptotic function of Bcl-2. In this study, a novel way of targeting Bcl-2 using small molecules that functionally convert the function of Bcl-2 from an anti-apoptotic to a pro-apoptotic protein was shown. The inventors demonstrated that BFC1103 can successfully suppress triple negative breast cancer lung metastasis in a mouse model.

It was shown herein that BFC1103 induces apoptosis in multiple cancer cell types expressing Bcl-2. The potency of BFC1103 increases with the increase in levels of Bcl-2 expression. This Bcl-2 dependent action of BFC1103 could be a great tool for treating refractory and resistant cancers that rely on Bcl-2. BFC1103 induced a change in conformation of Bcl-2, which correlated with an induction of apoptosis. This induction of apoptosis follows the mitochondrial intrinsic death pathway. The data suggest that BFC1103 has an affinity towards the loop domain of Bcl-2. Thus, BFC1103 mimics Nur77 or NuBCP-9 in interacting with the loop domain of Bcl-2, resulting in a change in its conformation and an induction of apoptosis. BFC1103 and its structural analogs have potential for treating highly metastatic cancers expressing Bcl-2.

5. Bcl-2 Functional Converters (BFCs) as Therapeutics for Chemo-Resistant Lung and Breast Cancers In some embodiments, disclosed herein are methods of treating Bcl-2-expressing cancer in a subject, comprising administering to a subject in need of Bcl-2 expressing cancer treatment, a therapeutically effective amount of an agent that exposes the BH3 domain of Bcl-2 thereby converting Bcl-2 into a pro-apoptotic protein, wherein the cancer is chemotherapy-resistant cancer. In some embodiments, the cancer is chemotherapy-resistant breast or chemotherapy-resistant lung cancer. In other embodiments, the cancer is resistant to commonly used cancer chemotherapeutics such as paclitaxel or doxorubicin. In other embodiments, the cancer is resistant to more than one cancer chemotherapeutic agent.

To ascertain if Bcl-2 is implicated in paclitaxel resistance and determine if Bcl-2 functional converters can be used to selectively kill paclitaxel resistant cancer, the inventors developed paclitaxel resistant lines. Initially paclitaxel sensitive lines were identified (H460) (termed parental) through use of viability assay. The sensitive parental line was treated with paclitaxel once a week for 48 hours and allowed to recover for a period of 6 weeks. As a result, H460 parental and resistant lines were treated with paclitaxel 1-10 nM for 48 hours and imaging indicated that parental line was responsive and resistant line was not (FIG. 25A). H460 paclitaxel resistance was confirmed through use of viability assay as parental cells viability was reduced by 90% while the resistant line was unaffected (FIG. 25B). The derived resistant H460 cells had similar levels of resistance to paclitaxel as the multidrug resistant cell line H69AR (FIG. 25B). It was further shown 10 nM paclitaxel inhibited the parental cells ability to form colonies in 2D and 3D soft agar assays, while resistant lines tumorigenicity was unchanged (FIGS. 25C and 25D). In both viability assays and colony formation assays, the paclitaxel resistant line was also less susceptible to doxorubicin treatment, indicating cross resistance (FIGS. 25B-25C). There was minimal induction of apoptosis in the derived H460 resistant line compared to parental sensitive line after exposure to 10 nM paclitaxel for 48 hours, as shown by Annexin V staining (FIG. 25E). Co-culture experiments, to represent a heterogenous tumor, using a 50:50 mix of parental and resistant cells also showed similar levels of resistance as the resistant line. Further viability data and microscopy confirmed the derived line is resistant to paclitaxel compared with the parental line.

Changes in expression of Bcl-2 family members are a potential mechanism of resistance. Assessment of changes in the expression of Bcl-2 family of proteins identified an increase in expression of Bcl-2 in the paclitaxel resistant cell line (FIG. 26A). However, there was no increase in other anti-apoptotic Bcl-2 family members Bcl-xl and Mcl-1 (FIG. 26A). This increase in Bcl-2 expression in the resistant line was further confirmed in the presence of paclitaxel which also induced cleavage of caspase 3 in parental line but not in resistant line (FIG. 26B). Expression of Bcl-2 in H69AR cells was comparable to H460 parental cells (FIG. 26C). To determine if gene expression was contributing to elevated Bcl-2, RT-qPCR analysis was used. There was no significant change in Bcl-2, however Mcl-1 mRNA expression had decreased (FIG. 26D). To determine if expression of Bcl-2 confers resistance to paclitaxel, MDA-MB-231 cells with low basal levels of Bcl-2 were transfected with Bcl-2 and stable lines were derived (FIG. 26E). Paclitaxel treatment reduced viability of MDA-MB-231 cells transfected with pcDNA vector, while Bcl-2 transfected MDA-MB-231 cells were partially resistant (FIG. 26E).

To determine if H460 paclitaxel resistant cells with elevated Bcl-2 expression were susceptible to Bcl-2 targeting, cells were treated with Bcl-2 functional converters and viability assessed. Treatment with BFC1108, BFC1111, BFC1103 all reduced viability of resistant line preferentially (FIG. 27A). BFC1108 reduced colony formation ability of resistant line preferentially (FIG. 27B). Furthermore, combination of paclitaxel 1 nM and BFC1108 20 µM led to synergistic reduction in cell viability after 24 hours (FIG. 27C). BFC1108 treatment induced apoptosis in the resistant line preferentially after 48 hour treatment (FIG. 27D).

To determine if BFCs could target and preferentially kill other types of therapy resistant cancer, paclitaxel and doxorubicin resistant triple negative breast cancer cell lines were derived. MDA-MB-468 parental and resistant lines were treated with paclitaxel and viability was assessed after 72 hours, the derived resistant line viability was unaffected by 50 nM, however parental line was sensitive (FIG. 28A). Paclitaxel-resistant line also displayed greater colony forming ability than parental line (FIG. 28B). Paclitaxel-resistant line was cross-resistant to other commonly used chemotherapeutics such as doxorubicin and fluorouracil (FIG. 28C). Additionally a doxorubicin resistant line was derived, and viability was tested after 72 hour treatment (FIG. 28D).

To determine if paclitaxel and doxorubicin resistant triple negative breast cancer cells could be preferentially targeted by BFCs viability assays were performed. MDA-MB-468 paclitaxel resistant cells were preferentially killed by BFC1108 in a dose dependent manner (FIG. 29A). BFC1108 also reduced colony forming ability of the paclitaxel resistant cells (FIG. 29B). BFC1108 reduced viability of doxorubicin resistant cells after 72 hour treatment (FIG. 29C).

To determine if BFCs can target therapy resistant lung cancer cells in vivo, a zebrafish xenograft model was used. BFC 20A, B18 and MTX led to a reduction in paclitaxel resistant H460 growth in vivo. (FIGS. 30A and 30B)

6. Structural Basis of Methotrexate Binding to Bcl-2

In some embodiments, the small molecule Bcl-2 functional converter of the methods disclosed herein, for example, MTX or MTX analog, induces apoptosis and/or reduces viability of a cell by binding to a six amino acid-segment (SEQ ID NO 1) of the Bcl-2 loop domain (SEQ ID NO 2) thereby converting Bcl-2 into a pro-apoptotic protein and activating the intrinsic apoptosis pathway within the cell. In some instances, binding of the small molecule to the peptide sequence exposes the BH3 domain of Bcl-2 thereby the small molecule Bcl-2 converter is a small molecule mimic of NuBCP-9 peptide. In other embodiments, a small molecule mimic of NuBCP-9 peptide is a small molecule that binds to the six amino acid-segment (SEQ ID NO 1) of the Bcl-2 loop domain (SEQ ID NO 2).

```
SEQ ID NO 1:
EWDAGDVGAAPPGAAPAPGIFSSQPGHTPHPAASRDPVARTSPLQTPAAP

GAAAGPALSPVP

SEQ ID NO 2:
HTPHPA
```

In certain embodiments, screening for small molecule Bcl-2 functional converters that bind to the HTPHPA sequence, or amino acid residues number 55-60, of the Bcl-2 loop domain is accomplished by nuclear magnetic resonance (NMR). In some embodiments, the NMR screening is done by titrating a small molecule agent into solution of a 15N-13C uniformly labeled Bcl-2 loop domain and monitoring chemical shift perturbations by 15N-1H heteronuclear single quantum coherence (HSQC), analyzing of the chemical shift perturbations of His55 and His58 as a function of the molecule concentration, plotting hyperbolic binding curves, and determining the binding affinity of the small molecule.

In an exemplary experiment, NMR was used to identify the residues of the Bcl-2 loop that are involved in binding to methotrexate (MTX). Complete backbone assignments of the Bcl-2 loop domain were obtained using $^{13}$C-direct detect experiments due to an exceptionally high number of proline residues, which compose 20% of the 62 amino acid Bcl-2 loop domain (FIG. 31B).

Unlabeled MTX was titrated into $^{15}$N-$^{13}$C uniformly labeled Bcl-2 loop domain and chemical shift perturbations were monitored by $^{15}$N-$^{1}$H heteronuclear single quantum coherence (HSQC) (FIG. 31C). Six resonances corresponding to residues 55-60 in the middle of the Bcl-2 loop domain (FIG. 31C) show a significant perturbation with MTX and are thus inferred to be responsible for MTX binding. The increasing chemical shift perturbations as a function of MTX concentration indicates that the bound and free forms of the Bcl-2 loop domain are in fast exchange on the NMR timescale. The exception is Pro59, for which the resonance disappeared upon MTX addition, indicating that it is in intermediate exchange (FIG. 31B, box). The segment responsible for binding includes two histidines, suggesting a preference for interaction with the indole sidechain. Analysis of the chemical shift perturbations of His55 and His58 as a function of MTX concentration reveals hyperbolic binding curves that can be fit to a Hill model to determine binding affinity (FIG. 31D).

The $K_d$ values were determined to be 5.1 mM and 11.4 mM for His55 and His58, respectively. Both yield Hill coefficients close to 1.0, indicating a lack of cooperativity. Importantly, NMR titration of the Bcl-2 loop domain with the NuBCP-9 peptide shows the same Bcl-2 residues undergoing chemical shift perturbations as titration with MTX (FIG. 31E), suggesting that the two molecules have the same specificity for Bcl-2 binding. NuBCP-9 titration resulted in a lower magnitude chemical shift perturbation than MTX, indicating that it binds to the Bcl-2 loop domain more weakly. As shown in FIG. 31E, MTX and NuBCP-9 cause approximately the same magnitude of chemical shift perturbation when MTX concentration is 1.6 mM (grey bars) and NuBCP-9 concentration is 8.6 mM (blue bars). Titration with the functionally inactive form of the NuBCP-9 peptide resulted in even lower magnitude chemical shift perturbations (black bars), about half that of NuBCP-9 at the same concentration, suggesting that mutation of NuBCP-9 reduced it binding to the Bcl-2 loop domain.

Additionally, the NMR data provides insight into the structure and dynamics of the Bcl-2 loop domain in its free and bound forms. Limited $^1H$ chemical shift dispersion in the HSQC (FIG. 31C) and lack of secondary structure preference as determined by differences in Cα and Cβ chemical shifts from random coil chemical shifts (FIG. 31F) indicate that the Bcl-2 loop domain is primarily disordered. A plot of $R_2/R_1$ values vs. residue position suggests some motional heterogeneity (FIG. 31G). Values ranged from 1.5-4.8 with an average value of 2.2. Relatively higher $R_2/R_1$ values for residues 55-60 indicate motional restriction in this region, which is possibly important for MTX binding. However, heteronuclear NOE values measured at 10° C. did not show a change in dynamics on the ps-ns timescale in the presence of MTX (FIG. 31H).

These results demonstrate that methotrexate interacts with residues 55-60 in the loop domain of Bcl-2 and exposes its BH3 domain. The interaction was demonstrated by NMR as well as altered proteolysis of the loop domain of Bcl-2 in the presence of methotrexate. Although the loop domain is unstructured, residues 50-62 show some motional restriction. It is predicted that this restriction results in smaller change in entropy upon methotrexate binding and enhanced affinity.

Preferred embodiments of this invention are described herein, including the best mode known to the inventors for carrying out the invention. Variations, changes, modifications and substitution of equivalents on those preferred embodiments will become apparent to those of ordinary skill in the art upon reading the foregoing description. The inventors expect skilled artisans to employ such variations, changes, modifications and substitution of equivalents as appropriate, and the inventors intend for the invention to be practiced otherwise than specifically described herein. Those of skill in the art will readily recognize a variety of non-critical parameters that could be changed, altered or modified to yield essentially similar results. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

EXAMPLES

1. Screening for Small Molecule Functional Converters of Bcl-2

The aim of this study was to find safe targeted therapeutics for hard to treat cancers that utilize Bcl-2 for their survival, and resistance to conventional treatments. In this study, the inventors found small molecules that specifically induce cell death in triple negative breast cancer cells MDA-MB-231 over-expressing Bcl-2, compared to their Bcl-2 low expressing control cells. A viability assay was set up to screen small molecule library in MDA-MB-231 cells with high and low Bcl-2 expression. The inventors found methotrexate and iodoacetamide from the LOPAC library to selectively induce more cell death in high-Bcl-2 expressing MDA-MB-231 cells. The inventors also found six novel small molecules that induced Bcl-2 specific reduction in viability of MDA-MB-231 cells expressing high levels of Bcl-2. These small molecules can be further developed into novel therapeutics to treat cancers expressing Bcl-2 and as combination treatments with other therapeutics that induce Bcl-2 expression.

Screening Library

The LOPAC1280™ library of pharmacologically active compounds was obtained from Sigma, Inc. Master library plates were diluted in DMSO to a 1 mM concentration for a 1:100 addition to media and final DMSO concentration of 1% (v/v) for screening. ChemBridge library consisting of 50,000 active pharmacophores was purchased from ChemBridge (San Diego, CA). Master library plates were diluted to 1 mM concentration for a final DMSO concentration of 1% (v/v) in the screening assay. For validations 10 mg of each hit compound was ordered form respective supplier and 20 mM stocks in DMSO were made. All subsequent in vitro testing was done under 0.1% (v/v) DMSO concentration.

Cell Culture

MDA-MB-231 cells were cultured in Dulbecco's Modified Eagle Medium (DMEM) with L-glutamine (Mediatech Inc., VA) supplemented with 10% FBS (Tissue Culture Biologicals, CA), 100 IU/mL penicillin, and 100 µg/ml streptomycin (Mediatech Inc., VA) in a humidified 5% $CO_2$ incubator. Cells were cultured under 80% confluency and passaged once in 3 days.

Generation of Breast Cancer Cell Lines Stably Overexpressing Bcl-2

MDA-MB-231 and MCF-7 breast cancer cell lines stably overexpressing Bcl-2 were generated via electroporation and subsequent clonal expansion in G418-containing media. For MDA-MB-231 cells, $5 \times 10^6$ cells per transfection were suspended in 400 µL of DMEM and electroporation with a Gene Pulser Xcell (Biorad, Hercules, CA) using an exponential decay protocol set with the following parameters (Voltage=280 V, capacitance=500 µF, resistance ($\Omega$)=$\infty$) in a 2 mm electroporation cuvette (Biorad, Hercules, CA). Cells were electroporated in the presence of either 2.5 µg pcDNA (MDA-MB-231/Vector) or 2.5 µg BCL-2 (MDA-MB-231/Bcl-2). For MCF-7 cells (MCF-7/Vector and MCF-7/Bcl-2), the same conditions described above were used, except that the electroporation voltage was 250 V and capacitance was 950 µF. For all electroporations, the actual voltages delivered did not vary significantly from the initial voltage delivery setting. After electroporation, cells were seeded into 150 cm$^2$ cell culture dishes at a density of $3 \times 10^5$ cells/plate in a volume of 15 mL. The following day, 5 mL of 10% DMEM containing 4× G418 (Omega Scientific, Tarzana, CA) was added such that the final concentrations were 900 µg/mL and 750 µg/mL for transfected MDA-MB-231 and MCF-7 cells, respectively. For both MDA-MB-231 and MCF-7 cells, an additional transfection was performed with a GFP-expression vector to verify successful DNA uptake under the given electroporation conditions and were discarded after confirming GFP expression with an inverted Zeiss microscope with GFP-fluorescence monitoring capabilities. During formation of colonies (~2 weeks), dead cells were removed by aspiration and media was replaced with G418-containing every 4-5 days. Sufficiently sized single, isolated colonies (~15 per transfection) were selected by surrounding colonies with a hydrophobic barrier from a wax pen, light trypsinization, and transfer to 24 well platers. Individual colonies were expanded thereafter in G418 containing media to 6 well plates and then 100 cm$^2$ dishes, after which cells were harvested for freezer stocks and whole cell lysates, as well as continued propagation as needed. Levels of Bcl-2 overexpression present in the selected clones, several lines were chosen for use in small molecule screening and secondary validation of hits, during which time continued Bcl-2 overexpression was monitored by western blot from fresh whole cell lysates prepared every 1-2 weeks. Several pcDNA vector transfected cell lines were chosen as controls for screening and hit validation.

Compound Treatments

Library plates were spun down in a centrifuge and thawed in a desiccator before opening in the cell culture hood in dark. All treatments were done in cells plated in black opaque plates. Treatments were done in dark as a precaution for light sensitivity of novel small molecules. DMSO was used as solvent for dilution of compounds.

Screening Assays

To screen for Bcl-2 selective compounds, MDA-MB-231 cells (MDA-MB-231/Vector and MDA-MB-231/Bcl-2) were plated at 4000 cells per well in a 96 well black opaque plate. The day after plating the cells, treatment from the library plates was done so as to add 1 µL of the compound into the cells, resulting in 10 µM concentration. For nonspecific negative control, 25 nM of staurosporin was used. Treatments were done at 10% serum conditions for 24 h. Post treatment viability was assessed by CellTiter Glo Cell Viability assay (Promega Inc., Madison, WI) as per manufacturer instructions.

Data Analysis

Viability for test compounds in each cell line (MDA-MB-231/Vector and MDA-MB-231/Bcl-2) was normalized to their respective vehicle treatments. Compounds that had at least 20% less viability in the MDA-MB-231/Bcl-2 cell line than the MDA-MB-231/Vector cell line were selected as initial hits and shortlisted for revalidation. Revalidated compounds were reordered for further testing and characterization. All data analyses were performed using Microsoft Excel.

2. Demonstration That Methotrexate Functionally Converts Bcl-2 into A Pro-Apoptotic Protein Cell Culture MDA-MB-231, MCF-7, HepG2, ZR-75-1, A375, MEFs and H460 were cultured in DMEM with L-glutamine (Mediatech Inc., Manassas, VA) supplemented with 10% fetal bovine serum (Tissue Culture Biologicals, Tulare, CA) with 10,000 U/mL penicillin streptomycin (Mediatech Inc., Manassas, VA) in a humidified chamber with 5% $CO_2$. LNCaP cells were cultured in RPMI 1640 (Mediatech Inc., Manassas, VA). MCF10-A cells were cultured in DMEM/F-12 with appropriate supplements. All cells were passaged once in every 3 days.

Generation of Stable Cell Lines

MDA-MB-231 and MCF-7 breast cancer cell lines stably overexpressing Bcl-2 were generated via electroporation and subsequent clonal expansion in G418-containing media. MDA-MB-231 cell clones with sufficiently high expression of Bcl-2 (MDA-MB-231/Bcl-2) determined by western blotting was selected for screening along with their vector controls (MDA-MB-231/Vector). Similarly MCF-7 cells clones were selected for characterization of lead molecules.

Chemicals

The LOPAC1280™ library of pharmacologically active compounds was obtained from Sigma, Inc (St. Louis, MO). All subsequent dilutions were made in DMSO. Folate was obtained from VWR, all other chemotherapeutic drugs were obtained from Cayman chemicals.

Viability and Apoptotic Assays

Cell viability was determined using CellTiter Glo Luminescent Cell Viability Assay (Promega, Madison, WI) as per manufacturer instructions. DAPI stain was used to assess apoptosis. Colony forming assays were performed as described previously.

Antibodies and Stains

Bcl-2 BH3 antibody was obtained from Abgent, CA Bcl-2 antibody was obtained from Santa Cruz, CA Ki-67 and H&E was obtained from Cell signaling. JC-1 dye was obtained from Roche, CA Bcl-2 Knockdown For Bcl-2 knockdown experiments, MDA-MB-468 cells were seeded at 4,000 cells per well in a 96 well black plate.

The day after seeding, cells were subjected to Bcl-2 knockdown with 25 ng siRNAs (Dharmacon Research, Lafayette, CO) or 25 ng control siRNA against luciferase (Dharmacon Research, Lafayette, CO) using Dharmafect as transfecting reagent. After 72 h of transfection time, cells were treated with indicated compounds for 48 h and viability was assayed with CellTiter Glo Luminescent Cell Viability Assay (Promega, Madison, WI).

Invasion Assay

Invasion assay was performed using BD transwell invasion assay kit. MDA-MB-231 cells were treated for 16 h at 10 µM concentration and membrane was stained with prolong anti-fade DAPI stain and number of cells invaded were counted under a fluorescent microscope.

Limited Proteolysis Assay

GST-Bcl-2 and GST only fragments (60 µg) were incubated with 0.1% DMSO or BFC1103 (50 µM) for 1 h and proteolyzed by 3 µg/ml of trypsin for 1, 2, 4 and 8 min. Reactions were quenched by the addition of laemmli buffer. The resulting protease cleavage fragments were resolved on a 12% SDS-PAGE gel and visualized by coomassie blue staining.

Co-IP Experiments

For CoIP experiments, HEK293T cells were plated in a 6 well plate and transfected with indicated expression plasmids by lipofectamine. The total amount of DNA was maintained at 2.5 µg. After 12 h of transfection, cells were treated with DMSO or 10 µM MTX for 16 h. The cells were then lysed on ice using RIPA buffer with freshly added protease inhibitor cocktail (Complete, mini, EDTA-free protease inhibitor cocktail, Roche, Inc.). The lysis buffer contained either DMSO or 10 µM MTX. Cell lysates were incubated on ice for 30 min and then spun at 14,000 rpm for 30 min at 4° C. Cleared lysates were incubated with Bcl-2 antibody (sc-509, Santacruz) and incubated at 4° C. for 2-4 h end-over-end mixing. After incubation a volume of sepharose beads (sc-2003, Santacruz) were added to each sample and left end-over-end mixing overnight at 4° C. The beads were then washed four times with RIPA buffer containing either DMSO or 10 µM and then solubilized in laemmli buffer. Proteins were analyzed on 10-12% SDS-PAGE and immunoblotted with mouse polyclonal anti-Bcl-2 (sc-509, Santacruz), mouse polyclonal anti-GFP (33-2600, Thermofisher).

Xenograft Experiments

All animal experiments were performed as per approved protocols from the IACUC at Oregon State University. 5 week old NOD.SCID mice were procured from Jackson Labs. Treatments were started once palpable tumors were detected. MTX was treated twice a week at 100 mg/kg dose. Body weight was measured twice a week. Tumor burden was measured twice a week using digital calipers.

Statistical Analysis

The statistical significance of difference between groups was analyzed by two-sided unpaired non-parametric student t test with Mann-Whitney test. Results were considered significant at p<0.05.

3. Small Molecule Bcl-2 Functional Converter BFC1108 for Breast Cancer Therapy Cell Culture MDA-MB-231, MCF-7, HepG2, ZR-75-1, A375, MEFs and H460 were cultured in DMEM with L-glutamine (Mediatech) supplemented with 10% fetal bovine serum (tissue culture biologicals) with 10,000 U/mL penicillin streptomycin (Mediatech) in a humidified chamber with 5% $CO_2$. LNCaP cells were cultured in RPMI 1640 (Mediatech). MCF10-A cells were cultured in DMEM/F-12 with appropriate supplements. All cells were passaged once in every 3 days.

Generation of Stable Cell Lines

MDA-MB-231 and MCF-7 breast cancer cell lines stably overexpressing Bcl-2 were generated via electroporation and subsequent clonal expansion in G418-containing media. MDA-MB-231 cell clones with sufficiently high expression of Bcl-2 (MDA-MB-231/Bcl-2) determined by western blotting was selected for screening along with their vector controls (MDA-MB-231/Vector). Similarly MCF-7 cells clones were selected for characterization of lead molecules.

Chemicals

ChemBridge library was order from ChemBridge Corp, CA. All subsequent dilutions were made in DMSO.

Viability Assays

Cell titer glo assay (Promega, CA) was used for assessing viability as per manufacturer instructions. DAPI stain was used to assess apoptosis.

Antibodies

Bcl-2 BH3 antibody was obtained from Abgent, CA Bcl-2 antibody was obtained from Santa Cruz, CA Ki-67 and H& E was obtained from Cell signaling. JC-1 was obtained from Roche, CA Bcl-2 Knockdown For Bcl-2 knockdown experiments, MDA-MB-468 cells were seeded at 4,000 cells per well in a 96 well black plate. The day after seeding, cells were subjected to Bcl-2 knockdown with 25 ng siRNAs (Dharmacon Research, Lafayette, CO) or 25 ng control siRNA against luciferase (Dharmacon Research, Lafayette, CO) using Dharmafect as transfecting reagent. After 72 h of transfection time, cells were treated with indicated compounds for 48 h and viability was assayed with CellTiter Glo Luminescent Cell Viability Assay (Promega, Madison, WI).

Limited Proteolysis Assay

GST-Bcl-2 and GST only fragments (60 µg) were incubated with 0.1% DMSO or BFC1103 (50 µM) for 1 h and proteolyzed by 3 µg/ml of trypsin for 1, 2, 4 and 8 min. Reactions were quenched by the addition of laemmli buffer. The resulting protease cleavage fragments were resolved on a 12% SDS-PAGE gel and visualized by coomassie blue staining.

Animal Experiments

All animal experiments were performed as per approved protocols from the IACUC at Oregon State University. For the mammary fat pad xenograft study, 5 week old NOD-.SCID mice were procured form Jackson labs. About $10^6$ cells were injected into both the lower flanks of mammary fat pad in PBS. Palpable tumors were detected in 4 weeks after which treatment with BFC1108 at 100 mg/kg twice a week continued till end of the study. Tumor mass was measured using digital calipers twice a week along with body weight. At the end of the study mice were euthanized and tumors were collected for immunohistochemical analysis.

For the lung metastatic study, 5 week old Nude mice were procured from Jackson Labs. About 200,000 LMD231-Luc2 cells in PBS were injected into the tail vein. Lung metastasis could be detected in 2 weeks' time. Treatments with BFC1108 at 100 mg/kg, 4 times a week, were started a day after the cells were injected. Body weight was measured twice a week. Bioluminescence was measured once a week while the mice are under anesthesia. At the end of the study mice were euthanized and lung tissues were dissected and fixed for immunohistochemical analysis.

Statistical Analysis

The statistical significance of difference between groups was analyzed by two-sided unpaired non-parametric student t test with Mann-Whitney test. Results were considered significant at p<0.05.

4. Small Molecule Bcl-2 Functional Converters for Breast Cancer Lung Metastasis Cell Culture MDA-MB-231, MCF-7, HepG2, ZR-75-1, A375, MEFs, LMD231 and H460 were cultured in DMEM with L-glutamine (Mediatech Inc., Manassas, VA) supplemented with 10% fetal bovine serum (Tissue Culture Biologicals, Tulare, CA) with 10,000 U/mL penicillin streptomycin (Mediatech Inc., Manassas, VA) in a humidified chamber with 5% $CO_2$. LNCaP cells were cultured in RPMI 1640 (Mediatech Inc., Manassas, VA). MCF10-A cells were cultured in DMEM/F-12 with appropriate supplements as previously described 23 (Mediatech Inc., Manassas, VA). All cells were passaged once in every 3 days.

Generation of Bcl-2 Stable Cell Lines

MDA-MB-231 and MCF-7 breast cancer cell lines stably overexpressing Bcl-2 were generated via electroporation and subsequent clonal expansion in G418-containing media. MDA-MB-231 cell clones with sufficiently high expression of Bcl-2 (MDA-MB-231/Bcl-2) determined by western blotting was selected for screening along with their vector controls (MDA-MB-231/Vector). Similarly MCF-7 cells clones were selected for characterization of lead molecules.

Chemicals

ChemBridge library was ordered from ChemBridge Corp, San Diego, CA. Master library plates were diluted in DMSO to achieve 1 mM stocks for a final DMSO concentration of 1% (v/v). Validations were done with reordered compounds that were dissolved in DMSO to get master stocks of 20 mM. The final concentration of DMSO was always maintained under 0.1% (v/v) in all cell culture assays.

Viability and Apoptotic Assays

CellTiter Glo Luminescent Cell Viability Assay (Promega, Madison, WI) was used for assessing viability as per manufacturer instructions. DAPI stain was used to assess apoptosis. Colony forming assays were performed as described previously.

Antibodies

Bcl-2 BH3 antibody was obtained from Abgent (San Diego, CA). Bcl-2 antibody was obtained from Santa Cruz Biotechnology (Dallas, TX). Ki-67 and H&E was obtained from Cell Signaling Technology (Danvers, MA). JC-1 kit was obtained from Roche, USA.

Bcl-2 Knockdown

For Bcl-2 knockdown experiments, MDA-MB-468 cells were seeded at 4,000 cells per well in a 96 well black plate. The day after seeding, cells were subjected to Bcl-2 knockdown with 25 ng siRNAs (Dharmacon Research, Lafayette, CO) or 25 ng control siRNA against luciferase (Dharmacon Research, Lafayette, CO) using Dharmafect as transfecting reagent. After 72 h of transfection time, cells were treated with indicated compounds for 48 h and viability was assayed with CellTiter Glo Luminescent Cell Viability Assay (Promega, Madison, WI).

Limited Proteolysis Assay

GST-Bcl-2 loop71 and GST only fragments (60 μg) were incubated with 0.1% DMSO or BFC1103 (50 μM) for 1 h and proteolyzed by 3 μg/ml of trypsin for 1, 2, 4 and 8 min. Reactions were quenched by the addition of Laemmli buffer. The resulting protease cleavage fragments were resolved on a 12% SDS-PAGE gel and visualized by Coomassie blue staining.

Metastatic Model and Bioluminescence Analysis

For experimental lung metastases model, LMD-231 cells derived from MDA-MB-231 that repeatedly colonized lungs were used 23. Lenti viral particles with luciferase expression vector (GenTarget, San Diego, CA) was used to transduce LMD-231 cells to obtain high luciferase expressing clone after clonal expansion. The stable expression of luciferase was monitored for 7 weeks in vitro before using in animal experiments.

All animal experiments were performed as per approved protocols from the IACUC at Oregon State University. 5 week old nude mice were procured from Jackson Labs (Bar Harbor, ME). Treatments were started a day after the LMD-Luc cells (200,000 cells suspended in DPBS) were injected into the lateral tail vein. Body weight was measured twice a week. Bioluminescence was measured twice a week using IVIS Lumina II (PerkinElmer, Waltham, MA) as per manufacturer instructions, while the mice were under anesthesia.

Statistical Analysis

The statistical significance of difference between groups was analyzed by two-sided unpaired non-parametric student t test with Mann-Whitney test. Results were considered significant at p<0.05.

5. Bcl-2 Functional Converters (BFCs) as Therapeutics for Chemo-Resistant Lung and Breast Cancers Cell Culture Cell lines were obtained from ATCC and maintained according to manufacturer's instructions. The human lung cancer cell line NCI-H460, H69AR (ATCC) were cultured in RPMI medium (Corning) containing 10% FBS. The human breast cancer cell line MDA-MB-231 was cultured in DMEM medium (Corning) containing 10% FBS. All cell lines were maintained at 5% CO2 and 37° C. Paclitaxel resistant H460 cells were derived by treating cells once a week over 6 weeks, initially with 1 nM paclitaxel and then increasing dose incrementally up to 100 nM. Once resistance was confirmed, paclitaxel was withdrawn from the cells. Resistance to paclitaxel was maintained without presence of paclitaxel measured up to 2 months. A parental line was maintained for a similar number of passages as the resistant line. All experiments were performed using cells that had not been treated with paclitaxel in at least three passages.

Viability Assays

Cells of interest were plated at 2000 cells per well in 96-well black tissue culture plate and allowed to adhere to the plate overnight. Viability assays were performed using 10% serum medium unless otherwise stated. Drugs were diluted in supplemented tissue culture medium and added at increasing concentrations, with DMSO as a vehicle control. Cells were then incubated for either 48 hour or 72 hours in presence of the compound, Promega Titer Glo was added to the wells at the assay end point according to manufacturer's protocol. Luminescence was measured using Tropix TR717 Microplate luminometer. Percentage of viable cells is relative to vehicle (100%). As a complementary viability assay, eBioscience Fixable Viability Dye eFluor 660(65-0864) was used to stain dead cells and analyzed using flow cytometry.

Western Blotting

Analysis of protein abundance was performed by Western blot according to standard techniques. Briefly cell lysates were collected using RIPA buffer with protease inhibitor, and then quantified using BCA assay. Some cell lysates were collected using 2×Laemmli buffer directly. Samples were boiled for 5 min and ran on SDS PAGE 12% and transferred to PVDF membranes by semi-dry transfer. Blots were probed using following antibodies, Bcl-2(SantaCruz, sc-509), GAPDH (SantaCruz, sc-365062), Mcl-1(Invitrogen, PA5-27597), Bcl-XL(Biosource, AHO0222), Cleaved Capase 3 Asp175 (Cell Signaling, 9661).

Real Time-Quantitative PCR

Total RNA was prepared using total RNA kit (Omega BioTek, Norcross, GA). The first strand cDNA was synthesized using Transcriptor kit (Roche, Indianapolis, IN). Real-time qPCR was done using FastStart Universal SYBR Green master mix (Roche) in 7500 Fast PCR system (Applied Biosystems) according to the manufacturer's protocol. The human GAPDH was used as a target.

Annexin V for Apoptosis with Flow Cytometry

Cells were seeded into 6 well tissue culture plates to give approximately 50% confluence and allowed to attach overnight. The cells were then treated for a period of time indicated in figure legend with the appropriate compound at various concentrations (see figure legends). An Annexin V-conjugate PerCP-eFluor 710 apoptosis detection kit was used as described by the manufacturer's protocol (eBioscience 88-8008). Harvesting of cells included collection of floating and attached cells following trypsinization. Data were acquired using an CytoFLEX S flow cytometer (Beckman Coulter, Brea, CA) and 10,000 events on the PC5.5 channel were analyzed using CytExpert software (Beckman Coulter). For Nur77 GFP tagged annexin V analysis, GFP positive population were selected and then Annexin V+population was determined. For each sample, 10,000 GFP+ events were collected. Annexin V positive cell population was considered to be the apoptotic population, and the percent of annexin V positive cell population was used to determine the extent of apoptosis.

Xenograft Study

Zebrafish (*Danio rerio*) were housed at the Sinnhuber Aquatic Research Laboratory at Oregon State University in accordance with Institutional Animal Care and Use Committee protocols. Adult 5D Tropical zebrafish were maintained under standard laboratory conditions of 28±1° C. on a 14 hr light/10 hr dark photoperiod in fish water consisting of reverse osmosis water supplemented with a commercially available salt solution (0.6%, Instant Ocean, UnitedPet Group, Inc., Blacksburg, VA, USA). Collected eggs were staged according to Kimmel et al. At 24 hours post fertilization (hpf), zebrafish embryos were maintained in E3 media with phenylthiourea (0.003%, Sigma, USA).

For transplantations, H460 cells were labeled with a CM-DiI dye (Thermo Fisher Sci.) according to the manufacturer's protocol and suspended to a concentration of $2 \times 10^7$ cells/mL. Cell suspension was loaded into a borosilicate glass needle pulled from a pipette by a micropipette puller (Sutter Instrument, Novato, CA). Approximately 100-200 H460 cells were transplanted into the yolk of 48 hpf embryos by air-driven micro-pressure injector as described. After transplantation, embryos recovered overnight at 33° C. without light.

For imaging, zebrafish xenografts were anesthetized by emersion in 0.2 mg/mL Tricaine E3 media and imbedded in 0.8% (w/v) low melting point agarose on a glass bottom 96-well plate. A Zeiss LSM 780 confocal microscope with a 10× objective was used to capture fluorescent cells at 1 and 4 day post injection (dpi). Images were captured as z-stacks with wide-field settings. H460 cancer growth was analyzed using Fiji (Fiji is Just Imagej) software. Images were processed by making a maximum projection image of the z-stack and using a median filter. Cancer area was calculated by creating a binary mask from thresholds with the Otsu algorithm and calculating the total area of the resulting segmented objects. Increases in total area from 1 to 4 dpi were considered cancer growth.

While illustrative embodiments have been illustrated and described, it will be appreciated that various changes can be made therein without departing from the spirit and scope of the invention.

SEQUENCE LISTING

```
Sequence total quantity: 2
SEQ ID NO: 1            moltype = AA  length = 62
FEATURE                 Location/Qualifiers
source                  1..62
                        mol_type = protein
                        organism = Homo sapiens
SEQUENCE: 1
EWDAGDVGAA PPGAAPAPGI FSSQPGHTPH PAASRDPVAR TSPLQTPAAP GAAAGPALSP  60
VP                                                                62

SEQ ID NO: 2            moltype = AA  length = 6
FEATURE                 Location/Qualifiers
source                  1..6
                        mol_type = protein
                        organism = Homo sapiens
SEQUENCE: 2
HTPHPA                                                             6
```

The embodiments of the invention in which an exclusive property or privilege is claimed ae defined as follows:

1. A method of treating Bcl-2-expressing cancer, comprising targeting the Bcl-2 protein in a cancer cell of a subject by administering to the subject a therapeutically effective amount of a compound of formula (III):

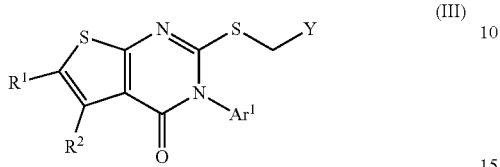

or a tautomer, hydrate, or salt thereof,
wherein:
$Ar^1$ is optionally substituted C6-C10 aryl or optionally substituted C5-C10 heteroaryl;
$R^1$ and $R^2$ are independently H, halogen, optionally substituted C1-C8 alkyl, optionally substituted C1-C8 alkenyl, optionally substituted C1-C8 alkynyl, O (C1-C8 alkyl), or C (O) NHR, wherein R is optionally substituted C1-C8 alkyl, optionally substituted C6-C10 aryl, or optionally substituted C5-C10 heteroaryl; or together with the carbon atoms to which each is attached, $R^1$ and $R^2$ form an optionally substituted 6-membered cycle;
Y is COOH, CONH$_2$, optionally substituted C6-C10 aryl, optionally substituted C5-C10 heteroaryl, or C (O) X; and
X is optionally substituted C6-C10 aryl, or optionally substituted C3-C10 heteroaryl.

2. The method of claim 1, wherein the compound is selected from the group consisting of:
2-[(2-methoxy-5-nitrobenzyl)thio]-3-phenyl-5,6,7,8-tetrahydro[1]benzothieno[2,3-d]pyrimidin-4 (3H)-one;
2-{[2-(4-chlorophenyl)-2-oxoethyl]thio}-5,6-dimethyl-3-phenylthieno[2,3-d]pyrimidin-4 (3H)-one;
5,6-dimethyl-2-{[2-(4-nitrophenyl)-2-oxoethyl]thio}-3-phenylthieno[2,3-d]pyrimidin-4 (3H)-one;
2-{[2-oxo-2-(2-thienyl)ethyl]thio}-3-phenyl-5,6,7,8-tetrahydro[1]benzothieno[2,3-d]pyrimidin-4 (3H)-one;
2-[(4-nitrobenzyl)thio]-3-phenyl-5,6,7,8-tetrahydro[1]benzothieno[2,3-d]pyrimidin-4 (3H)-one;
2-(benzylthio)-3-phenyl-5,6,7,8-tetrahydro[1]benzothieno[2,3-d]pyrimidin-4 (3H)-one;
2-[(4-methoxybenzyl)thio]-3-phenyl-5,6,7,8-tetrahydro[1]benzothieno[2,3-d]pyrimidin-4 (3H)-one;
{[3-(4-ethoxyphenyl)-4-oxo-3,4,5,6,7,8-hexahydro[1]benzothieno[2,3-d]pyrimidin-2-yl]thio}acetic acid;
2-{[3-(4-ethoxyphenyl)-4-oxo-3,4,5,6,7,8-hexahydro[1]benzothieno[2,3-d]pyrimidin-2-yl]thio}acetamide;
4-({[3-(4-methoxyphenyl)-4-oxo-3,4,5,6,7,8-hexahydro[1]benzothieno[2,3-d]pyrimidin-2-yl]thio}methyl)benzoic acid; and
7-tert-butyl-2-[(4-methoxybenzyl)thio]-3-phenyl-5,6,7,8-tetrahydro[1]benzothieno[2,3-d]pyrimidin-4 (3H)-one;
or a tautomer, hydrate, or salt thereof.

3. A method of treating Bcl-2-expressing cancer-in a subject, comprising administering to the subject in need of cancer treatment, a therapeutically effective amount of 2-[(2-methoxy-5-nitrobenzyl)thio]-3-phenyl-5,6,7,8-tetrahydro[1]benzothieno[2,3-d]pyrimidin-4 (3 H)-one, 2-{[2-(4-chlorophenyl)-2-oxoethyl]thio}-5,6-dimethyl-3-phenylthieno[2,3-d]pyrimidin-4 (3H)-one;
5,6-dimethyl-2-{[(2-methyl-1,3-thiazol-4-yl)methyl]thio}-3-phenylthieno[2,3-d]pyrimidin-4 (3H)-one;
5,6-dimethyl-2-{[2-(4-nitrophenyl)-2-oxoethyl]thio}-3-phenylthieno[2,3-d]pyrimidin-4 (3H)-one;
2-{[2-(4-fluorophenoxy)ethyl]thio}-5,6-dimethyl-3-phenylthieno[2,3-d]pyrimidin-4 (3H)-one;
2-{[2-oxo-2-(2-thienyl)ethyl]thio}-3-phenyl-5,6,7,8-tetrahydro[1]benzothieno[2,3-d]pyrimidin-4 (3H)-one;
2-[(4-nitrobenzyl)thio]-3-phenyl-5,6,7,8-tetrahydro[1]benzothieno[2,3-d]pyrimidin-4 (3H)-one;
2-(benzylthio)-3-phenyl-5,6,7,8-tetrahydro[1]benzothieno[2,3-d]pyrimidin-4 (3H)-one;
2-[(4-methoxybenzyl)thio]-3-phenyl-5,6,7,8-tetrahydro[1]benzothieno[2,3-d]pyrimidin-4 (3H)-one;
{[3-(4-ethoxyphenyl)-4-oxo-3,4,5,6,7,8-hexahydro[1]benzothieno[2,3-d]pyrimidin-2-yl]thio} acetic acid;
2-{[3-(4-ethoxyphenyl)-4-oxo-3,4,5,6,7,8-hexahydro[1]benzothieno[2,3-d]pyrimidin-2-yl]thio} acetamide;
4-({[3-(4-methoxyphenyl)-4-oxo-3,4,5,6,7,8-hexahydro[1]benzothieno[2,3-d]pyrimidin-2-yl]thio} methyl) benzoicacid; 7-tert-butyl-2-[(4-methoxybenzyl)thio]-3-phenyl-5,6,7,8-tetrahydro[1]benzothieno[2,3-d]pyrimidin-4 (3H)-one; or a tautomer, hydrate, or salt thereof.

* * * * *